US008536148B2

(12) United States Patent
Raben et al.

(10) Patent No.: US 8,536,148 B2
(45) Date of Patent: Sep. 17, 2013

(54) DISABLING AUTOPHAGY AS A TREATMENT FOR LYSOSOMAL STORAGE DISEASES

(75) Inventors: Nina N. Raben, N. Bethesda, MD (US); Cynthia Schreiner, Gowanda, NY (US); Rebecca Baum, Highland, UT (US); Shoichi Takikita, Rockville, MD (US); Tao Xie, Rockville, MD (US); Paul H. Plotz, Washington, DC (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/391,265

(22) PCT Filed: Sep. 2, 2010

(86) PCT No.: PCT/US2010/047730
§ 371 (c)(1),
(2), (4) Date: Feb. 17, 2012

(87) PCT Pub. No.: WO2011/028941
PCT Pub. Date: Mar. 10, 2011

(65) Prior Publication Data
US 2012/0149760 A1 Jun. 14, 2012

Related U.S. Application Data

(60) Provisional application No. 61/275,984, filed on Sep. 4, 2009.

(51) Int. Cl.
*A61K 48/00* (2006.01)

(52) U.S. Cl.
USPC ......... 514/44; 536/24.5; 536/24.31; 536/24.1

(58) Field of Classification Search
None
See application file for complete search history.

(56) References Cited

U.S. PATENT DOCUMENTS

| | | | |
|---|---|---|---|
| 6,066,626 | A | 5/2000 | Yew et al. |
| 6,537,785 | B1 | 3/2003 | Canfield et al. |
| 7,351,410 | B2 | 4/2008 | Bree et al. |
| 7,378,231 | B1 | 5/2008 | Meikle et al. |
| 7,563,591 | B2 | 7/2009 | Chamoles |
| 2006/0287358 | A1 | 12/2006 | Wustman |
| 2009/0029467 | A1 | 1/2009 | LeBowitz et al. |
| 2009/0117091 | A1 | 5/2009 | Lebowitz et al. |

FOREIGN PATENT DOCUMENTS

| | | |
|---|---|---|
| WO | WO 2007014323 | 2/2007 |
| WO | WO 2008112525 | 9/2008 |
| WO | WO2008112525 | 9/2008 |
| WO | WO2009049421 | 4/2009 |

OTHER PUBLICATIONS

Filimonenko et al. (J Cell Biology 2007. vol. 179: 485-500).*
Wei et al. (Human Mol. Genetics 2008, vol. 17: 469-477).*
Apel et al., Blocked autophagy sensitizes resistent carcinoma cells to radiation therapy, *Cancer Res.*, 68:1485-1494, 2008.
Bach et al., The defect in the Hunter syndrome: deficiency of sulfoiduronate sulfatase, *Proc. Natl. Acad. Sci. USA.*, 70:2134-2213, 1973.
Beutler, Enzyme replacement in Gaucher disease, 5 *PLoS Med.*, 1(2): e21, 118-121, 2004.
Bothe et al., Selective expression of *cre* recombinase in skeletal muscle fibers, *Genesis*, 26:165-166, 2000.
Breunig & Wanner, Update on Fabry disease: kidney involvement, renal progression and enzyme replacement therapy, *J. Nephrol.*, 21:32-37, 2008.
Cao & Klionsky, Physiological functions of Atg6/Beclin :1 a unique autophagy-related protein, *Cell Res* 17(10):839-849, 2007.
Cardone et al., Abnormal mannose-6-phosphate receptor trafficking impairs recombinant alpha-glucosidse uptake in Pompe disease fibroblasts, *Pathogenetics*, 1(6), 2008 (22 pages).
Carew et al., Modulating autophagy for therapeutic benefit, *Autophagy*, 3:464-467, 2007.
Cecconi & Levine, The role of autophagy in mammalian development: cell makeover rather than cell death, *Dev. Cell*, 15:344-357, 2008.
Charrow, Enzyme replacement therapy for Gaucher disease, *Expert Opin. Biol. Ther.*, 9:121-131, 2009.
Civallero et al., Twelve different enzyme assays on dried-blood filter paper samples for detection of patients with selected inherited lysosomal storage diseases. *Clin. Chim. Acta.*, 372:98-102, 2006.
Clarke, Narrative review: Fabry disease, *Ann. Intern Med.*, 20:425-433, 2007.
Clarke, The mucopolysaccharidoses: a success of molecular medicine. *Expert Rev. Mol. Med.*, 10:e1, 1-5, 2008.
Codogno & Meijer, Autophagy and signaling: their role in cell survival and cell death, *Cell death and differentiation*, 12:1509-1518, 2005.
Dean et al., Detection of Mucopolysaccharidosis Type II by Measurement of Iduronate-2-Sulfatase in Dried Blood Spots and Plasma Samples, *Clin. Chem.*, 52:643-649, 2006.
Desnick, Fabry disease, an under-recognized multisystemic disorder: expert recommendations for diagnosis, management, and enzyme replacement therapy, *Ann. Intern. Med.*, 138:338-346, 2003.
Dorfman et al., Occurrence of urinary acid mucopolysaccharides in the Hurler syndrome, *Proc. Natl Acad Sci USA*, 43:443-4462, 1957.
Dreyfus et al., White blood cells and the diagnosis of α-glucosidase deficiency, *Pediatr. Res.*, 14:342-344, 1980.
Fukuda et al., Dysfunction of endocytic and autophagic pathways in a lysosomal storage disease, *Ann. Neurol.*, 59:700-708, 2006.

(Continued)

*Primary Examiner* — Kimberly Chong
(74) *Attorney, Agent, or Firm* — Klarquist Sparkman, LLP

(57) ABSTRACT

Provided herein are methods of treating lysosomal storage disease, for instance Pompe disease, through inhibition of autophagy. Optionally, treatment is administered as an adjunct to enzyme replacement therapy (ERT).

16 Claims, 6 Drawing Sheets

(56) References Cited

OTHER PUBLICATIONS

Fukuda et al., Autophagy and mistargeting of therapeutic enzyme in skeletal muscle in Pompe disease, *Molecular Therapy*, 14, No. 6:831-839, 2006.

Fukuda et al., Acid alpha-glucosidase deficiency (Pompe disease), *Curr. Neurol. Neurosc. Rep.*, 7:71-77, 2007.

Hamacher-Brady et al., Enhancing macroautophagy protects against ischemia reperfusion injury in cardiac myocytes *J. Biol. Chem.*, 281:29776-29787, 2006.

Hay & Sonenberg, Upstream and downstream of mTOR, *Genes Dev* 18(16):1926-1945, 2004.

Kleijer et al., Prenatal diagnosis of glycogen storage disease type II: enzyme assay or mutation analysis? *Pediatr. Res.*, 38:103-106, 1995.

Kuma et al., The role of autophagy during the early neonatal starvation period., *Nature*, 432:1032-1036, 2004.

Lidove et al., Clinical results of enzyme replacement therapy in Fabry disease: a comprehensive review of literature, *Int. J. Clin. Pract.*, 61:293-302, 2007.

Mammucari et al., FoxO3 controls autophagy in skeletal muscle in vivo, *Cell Metab* 6(6):458-471, 2007.

Mizushima et al., Autophagosome formation in mammalian cells, *Cell structure and function*, 27:421-429, 2002.

Mizushima et al., In vivo analysis of autophagy in response to nutrient starvation using transgenic mice expressing a fluorescent autophagosome marker. *Mol Biol Cell* 15(3):1101-1111, 2004.

Morel & Clarke, The use of agalsidase alfa enzyme replacement therapy in the treatment of Fabry disease. *Expert Opin. Biol. Ther.*, 9:631-639, 2009.

Muenzer et al., A phase II/III clinical study of enzyme replacement therapy with idursulfase in mucopolysaccharidosis II (Hunter syndrome). *Genet. Med.*, 8:465-473, 2006.

Ninomiya et al., Demonstration of acid alpha-glucosidase in different types of Pompe disease by use of an immunochemical method. *J. Neurol. Sci.*, 66:129-139, 1984.

Petiot et al., Distinct classes of phosphatidylinositol 3'-kinases are involved in signaling pathways that control macroautophagy in HT-29 cells. *J. Biol. Chem.*, 275:992-998, 2000.

Raben et al., Targeted disruption of the acid alpha-glucosidase gene in mice causes an illness with critical features of both infantile and adult human glycogen storage disease type II. *J. Biol. Chem.*, 273:19086-19092, 1998.

Raben et al., Modulation of disease severity in mice with targeted disruption of the acid alpha-glucosidase gene. *Neuromuscular Disorders*, 10:283-291, 2000.

Raben et al., Conditional tissue-specific expression of the acid α-glucosidase (GAA) gene in the GAA knockout mice: implications for therapy, *Human Molecular Genetics*, 10(19):2039-2047, 2001.

Raben et al., Glycogen stored in skeletal but not in cardiac muscle in acid α-glucosidase mutant (Pompe) mice is highly resistant to transgene-encoded human enzyme, *Molecular Therapy*, 6(5):601-608, 2002.

Raben et al., Enzyme replacement therapy in the mouse model of Pompe disease, *Molecular Genetics and Metabolism*, 80(1-2):159-169, 2003.

Raben et al., Replacing acid α-glucosidase in Pompe disease: recombinant and transgenic enzymes are equipotent, but neither completely clears glycogen from type II muscle fibers, *Molecular Therapy*, 11(1):48-56, 2005.

Raben et al., Role of autophagy in the pathogenesis of Pompe disease, *Acta Myologica*, 26:45-48, 2007.

Raben et al., Suppression of autophagy in skeletal muscle uncovers the accumulation of ubiquitinated proteins and their potential role in muscle damage in Pompe disease, *Human Molecular Genetics*, 17, No. 24:3897-3908, 2008.

Raben et al., Suppression of autophagy permits successful enzyme replacement therapy in a lysosomal storage disorder—murine Pompe disease, Autophagy, 8:1078-89, 2010.

Raben et al., Differences in the predominance of lysosomal and autophagic pathologies between infants and adults with Pompe disease: implications for therapy. Mol Genet Metab;101(4):324-31, 2010.

Ralston et al., Detection and imaging of non-contractile inclusions and sarcomeric anomalies in skeletal muscle by second harmonic generation combined with two-photon excited fluorescence, *Journal of structural biology*, 162:500-508, 2008.

Rohrbach & Clarke, Treatment of lysosomal storage disorders: progress with enzyme replacement therapy. *Drugs*, 67:2697-2716, 2007.

Rubinsztein et al., Potential therapeutic applications of autophagy, *Nature Rev. Drug Disc.*, 6:304-312, 2007.

Seglen & Gordon, 3-Methyladenine: Specific inhibitor of autophagic/Lysosomal Protein Degradation in Isolated Rat Hepatocytes, *Proc. Natl. Acad. Sci. U.S.A.*, 79:1889-1892, 1982.

Schertzer, Optimizing plasmid-based gene transfer for investigating skeletal muscle structure and function. *Mol. Ther.*, 13:795-803, 2005.

Schlander & Beck, Expensive drugs for rare disorders: to treat or not to treat? The case of enzyme replacement therapy for mucopolysaccharidosis VI, *Curr. Med. Res. Opin.*, 25:1285-93, 2009.

Schoser et al., Therapeutic approaches in glycogen storage disease Type II/Pompe disease, *Neurotherapeutics: Journal of the American Society for Experimental Neurotherapeutics*, 5(4):569-578, 2008.

Raben, et al., "Suppression of autophagy in skeletal muscle uncovers the accumulation of ubiquitinated proteins and their potential role in muscle damage in Pompe disease," *Hum. Mol. Genet.*, 17:3897-3908, 2008.

Settembre et al., A block of autophagy in lysosomal storage disorders, *Human Mol. Genet.*, 17:119-129, 2008.

Shin et al., Diagnosis of Pompe's disease using leukocyte preparations. Kinetic and immunological studies of 1,4-α-glucosidase in human fetal and adult tissues and cultured cells. *Clin. Chim. Acta.*,148:9-19, 1985.

Strothotte et al., Enzyme replacement therapy with alglucosidase alfa in 44 patients with late-onset glycogen storage disease type 2: 12-month results of an observational clinical trial, *J. Neurol.*, 257(1)91-97, 2010; Epub Aug. 1, 2009.

Sun et al., Enhanced response to enzyme replacement therapy in Pompe disease after the induction of immune tolerance, *Am J. Hum. Genet.*, 81:1042-1049, 2007.

Takikita et al., Murine muscle cell models for Pompe disease and their use in studying therapeutic approaches, *Mol. Genet. Metab.*, 96:208-217, 2009.

Takikita et al., Fiber type conversion by PGC-1α activates lysosomal and autophagosomal biogenesis in both unaffected and Pompe skeletal muscle, PLoS One, 5(12):e15239, 2010.

Taniguchi et al., Alpha-glucosidase activity in human leukocytes: choice of lymphocytes for the diagnosis of Pompe's disease and the carrier state *Clin. Chim. Acta.*, 89:293-299, 1978.

Tolar & Orchard, alpha-L-iduronidase therapy for mucopolysaccharidosis type I. *Biologics*., 2:743-751, 2008.

Tomatsu et al., Enzyme replacement therapy in a murine model of Morquio A syndrome. *Hum. Mol. Genet.*, 17:815-824, 2007.

Umapathysivam et al., Determination of acid alpha-glucosidase activity in blood spots as a diagnostic test for Pompe disease. *Clin. Chem.*, 47:1378-1383, 2001.

Vergarajauregui & Puertollano, Mucolipidosis Type IV, *Autophagy*, 16:832-834, 2008.

Vergarajauregui et al., Autophagic dysfunction in mucolipidosis type IV Patients, *Human Mol. Genet.*, 17:2723-2737, 2008.

Wang and Klionsky, The molecular mechanism of autophagy, *Molecular Medicine*, 9(3/4):65-76, 2003.

Winslow & Rubinsztein, Autophagy in neurodegeneration and development, *Biochim. Biophys. Acta.*, 1782:723-729, 2008.

Yamamoto et al., Bafilomycin $A_1$ prevents maturation of autophagic vacuoles by inhibiting fusion between autophagosomes and lysosomes in rat hepatoma cell line, H-4-II-E cells, *Cell Struct. Funct.* 23:33-42, 1998.

Zhu et al., Carbohydrate-remodeled acid alpha-glycosidase with higher affinity for the caution-independent mannose 6-phosphate receptor demonstrates improved delivery to muscles of Pompe mice, *Biochem. J.*, 389(3): 619-628, 2005.

Jearawirlyapaisarn et al., "Sustained Dystrophin Expression Induced by Peptide-conjugated Morpholino Oligomers in the Muscles of *mdx* Mice," *Mol. Ther.*, 16(9):1624-1629, 2008.

\* cited by examiner

WT

MLCcre: Atg7F/F: GAA-/-

4m  5m  9m

FIG. 3A
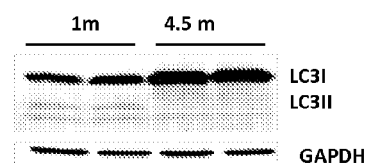
FIG. 3B
FIG. 4
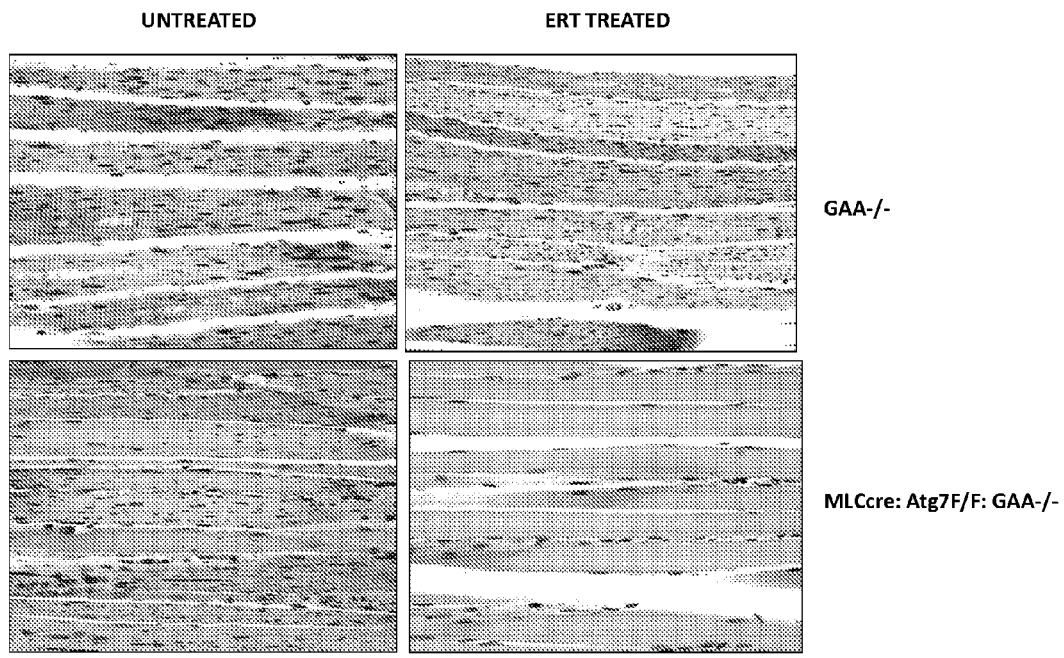

GAA-/-

MLCcre: Atg7F/F: GAA-/-

GAA-/-

HSAcre: Atg5F/F: GAA-/-

SEQUENCE LISTING

```
<160> NUMBER OF SEQ ID NOS: 22

<210> SEQ ID NO 1
<211> LENGTH: 3666
<212> TYPE: DNA
<213> ORGANISM: Mus musculus
<220> FEATURE:
<221> NAME/KEY: CDS
<222> LOCATION: (171)..(3032)

<400> SEQUENCE: 1
ggactccgcc gcctacgcag gaggtcgtgt gacgaggtcc gcgcggacga gccccgccca      60
cagaccacgt gacccacgct gcccgctgag cctgggggtc ttcggcctgg agggtgattg     120
cgcaggcctt cagaagtatt catgctgccc cgaaccaaca ggctttcacc atg aat       176
                                                          Met Asn
                                                          1 ata cgg aag ccc ctc tgt tcg aac tcc gtg gtt ggg gcc tgc acc ctt     224
Ile Arg Lys Pro Leu Cys Ser Asn Ser Val Val Gly Ala Cys Thr Leu
        5                  10                  15 atc tct ctg act aca gcg gtc atc ctg ggt cat ctc atg ctt cgg gag     272
Ile Ser Leu Thr Thr Ala Val Ile Leu Gly His Leu Met Leu Arg Glu
    20                  25                  30 tta atg ctg ctt ccc caa gac ctt cat gag tcc tct tca gga ctg tgg     320
Leu Met Leu Leu Pro Gln Asp Leu His Glu Ser Ser Ser Gly Leu Trp
35                  40                  45                  50 aag acg tac cga cct cac cac cag gaa ggt tac aag cca ggg cct ctg     368
Lys Thr Tyr Arg Pro His His Gln Glu Gly Tyr Lys Pro Gly Pro Leu
                55                  60                  65
```

```
cac atc cag gag cag act gaa cag ccc aaa gaa gca ccc aca cag tgt      416
His Ile Gln Glu Gln Thr Glu Gln Pro Lys Glu Ala Pro Thr Gln Cys
         70                  75                  80 gat gtg ccc ccc agc agc cgc ttt gac tgt gcc ccc gac aaa ggc atc      464
Asp Val Pro Pro Ser Ser Arg Phe Asp Cys Ala Pro Asp Lys Gly Ile
             85                  90                  95 tca cag gag caa tgc gag gcc cgc ggc tgc tgc tat gtc cca gca ggg      512
Ser Gln Glu Gln Cys Glu Ala Arg Gly Cys Cys Tyr Val Pro Ala Gly
        100                 105                 110 cag gtg ctg aag gag ccg cag ata ggg cag ccc tgg tgt ttc ttc cct      560
Gln Val Leu Lys Glu Pro Gln Ile Gly Gln Pro Trp Cys Phe Phe Pro
115                 120                 125                 130 ccc agc tac cca agc tac cgt cta gag aac ctg agc tct aca gag tcg      608
Pro Ser Tyr Pro Ser Tyr Arg Leu Glu Asn Leu Ser Ser Thr Glu Ser
                135                 140                 145 ggg tac aca gcc acc ctg acc cgt acc agc ccg acc ttc ttc cca aag      656
Gly Tyr Thr Ala Thr Leu Thr Arg Thr Ser Pro Thr Phe Phe Pro Lys
            150                 155                 160 gat gtg ctg acc tta cag ctg gag gtg ctg atg gag aca gac agc cgc      704
Asp Val Leu Thr Leu Gln Leu Glu Val Leu Met Glu Thr Asp Ser Arg
        165                 170                 175 ctc cac ttc aag atc aaa gat cct gct agt aag cgc tac gaa gtg ccc      752
Leu His Phe Lys Ile Lys Asp Pro Ala Ser Lys Arg Tyr Glu Val Pro
180                 185                 190 ctg gag acc cca cgt gtg ctg agc cag gca cca tcc cca ctt tac agc      800
Leu Glu Thr Pro Arg Val Leu Ser Gln Ala Pro Ser Pro Leu Tyr Ser
195                 200                 205                 210 gtg gaa ttc tca gag gaa ccc ttt gga gtg atc gtt cgt agg aag ctt      848
Val Glu Phe Ser Glu Glu Pro Phe Gly Val Ile Val Arg Arg Lys Leu
                215                 220                 225 ggt ggc cga gtg ttg ctg aac aca acc gtg gcc ccc ctg ttc ttc gct      896
Gly Gly Arg Val Leu Leu Asn Thr Thr Val Ala Pro Leu Phe Phe Ala
            230                 235                 240 gac cag ttc ctg cag ctg tcc act tcc ctg ccc tcc cag cac atc aca      944
Asp Gln Phe Leu Gln Leu Ser Thr Ser Leu Pro Ser Gln His Ile Thr
        245                 250                 255 ggc ctg ggg gaa cac ctc agc cca ctc atg ctc agc acc gac tgg gct      992
Gly Leu Gly Glu His Leu Ser Pro Leu Met Leu Ser Thr Asp Trp Ala
260                 265                 270 cgt atc acc ctc tgg aac cgg gac aca cca ccc tcg caa ggt acc aac     1040
Arg Ile Thr Leu Trp Asn Arg Asp Thr Pro Pro Ser Gln Gly Thr Asn
275                 280                 285                 290 ctc tac ggg tca cat cct ttc tac ctg gca ctg gag gac ggt ggc ttg     1088
Leu Tyr Gly Ser His Pro Phe Tyr Leu Ala Leu Glu Asp Gly Gly Leu
                295                 300                 305 gct cac ggt gtc ttc ttg cta aac agc aat gcc atg gat gtc atc ctg     1136
Ala His Gly Val Phe Leu Leu Asn Ser Asn Ala Met Asp Val Ile Leu
            310                 315                 320 caa ccc agc cca gcc cta acc tgg agg tca acg ggc ggg atc ctg gat     1184
Gln Pro Ser Pro Ala Leu Thr Trp Arg Ser Thr Gly Gly Ile Leu Asp
        325                 330                 335 gtg tat gtg ttc cta ggc cca gag ccc aag agc gtt gtg caa caa tac     1232
Val Tyr Val Phe Leu Gly Pro Glu Pro Lys Ser Val Val Gln Gln Tyr
340                 345                 350 ctg gat gtt gtg gga tac ccc ttc atg cct cca tac tgg ggc ctc ggc     1280
Leu Asp Val Val Gly Tyr Pro Phe Met Pro Pro Tyr Trp Gly Leu Gly
355                 360                 365                 370 ttc cac ctc tgc cgc tgg ggc tac tcc tcg acc gcc att gtc cgc cag     1328
Phe His Leu Cys Arg Trp Gly Tyr Ser Ser Thr Ala Ile Val Arg Gln
                375                 380                 385
```

```
gta gtg gag aac atg acc agg aca cac ttc ccg ctg gac gtg caa tgg        1376
Val Val Glu Asn Met Thr Arg Thr His Phe Pro Leu Asp Val Gln Trp
            390                 395                 400 aat gac ctg gac tac atg gac gcc cga aga gac ttc acc ttc aac cag        1424
Asn Asp Leu Asp Tyr Met Asp Ala Arg Arg Asp Phe Thr Phe Asn Gln
        405                 410                 415 gac agc ttt gcc gac ttc cca gac atg gtg cgg gag ctg cac cag gat        1472
Asp Ser Phe Ala Asp Phe Pro Asp Met Val Arg Glu Leu His Gln Asp
    420                 425                 430 ggc cgg cgc tac atg atg atc gtg gac cct gcc atc agc agc gca ggc        1520
Gly Arg Arg Tyr Met Met Ile Val Asp Pro Ala Ile Ser Ser Ala Gly
435                 440                 445                 450 cct gct ggg agt tac agg ccc tac gac gag ggt ctg cgg agg ggc gtg        1568
Pro Ala Gly Ser Tyr Arg Pro Tyr Asp Glu Gly Leu Arg Arg Gly Val
                455                 460                 465 ttc atc acc aac gag act ggg cag ccg ctg att ggg aag gtt tgg cct        1616
Phe Ile Thr Asn Glu Thr Gly Gln Pro Leu Ile Gly Lys Val Trp Pro
            470                 475                 480 gga acc acc gcc ttc cct gat ttc acc aac cct gag acc ctt gac tgg        1664
Gly Thr Thr Ala Phe Pro Asp Phe Thr Asn Pro Glu Thr Leu Asp Trp
        485                 490                 495 tgg cag gac atg gtg tct gag ttc cac gcc cag gtg ccc ttc gat ggc        1712
Trp Gln Asp Met Val Ser Glu Phe His Ala Gln Val Pro Phe Asp Gly
    500                 505                 510 atg tgg ctc gac atg aac gaa ccg tcc aac ttc gtt aga ggc tct cag        1760
Met Trp Leu Asp Met Asn Glu Pro Ser Asn Phe Val Arg Gly Ser Gln
515                 520                 525                 530 cag ggc tgc ccc aac aat gaa ctg gag aac ccc ccc tat gtg ccc ggg        1808
Gln Gly Cys Pro Asn Asn Glu Leu Glu Asn Pro Pro Tyr Val Pro Gly
                535                 540                 545 gtg gtt ggc ggg atc ttg cag gca gcc acc atc tgt gcc tcc agc cac        1856
Val Val Gly Gly Ile Leu Gln Ala Ala Thr Ile Cys Ala Ser Ser His
            550                 555                 560 caa ttc ctc tcc aca cac tac aac ctc cac aac ctg tac ggc ctc act        1904
Gln Phe Leu Ser Thr His Tyr Asn Leu His Asn Leu Tyr Gly Leu Thr
        565                 570                 575 gaa gct atc gcc tcc agc agg gcc ctg gtc aag act cgg gga aca cga        1952
Glu Ala Ile Ala Ser Ser Arg Ala Leu Val Lys Thr Arg Gly Thr Arg
    580                 585                 590 ccc ttt gtg atc tcc cgc tca acc ttc tcg ggc cac ggc cgg tac gct        2000
Pro Phe Val Ile Ser Arg Ser Thr Phe Ser Gly His Gly Arg Tyr Ala
595                 600                 605                 610 ggt cac tgg aca ggg gat gtg cgg agc tct tgg gag cat ctt gca tac        2048
Gly His Trp Thr Gly Asp Val Arg Ser Ser Trp Glu His Leu Ala Tyr
                615                 620                 625 tct gtg cca gac atc ctg cag ttc aac ctg ctg ggc gtg ccc ctg gtc        2096
Ser Val Pro Asp Ile Leu Gln Phe Asn Leu Leu Gly Val Pro Leu Val
            630                 635                 640 ggg gcg gac atc tgc ggc ttc ata gga gac acg tca gaa gag ctg tgt        2144
Gly Ala Asp Ile Cys Gly Phe Ile Gly Asp Thr Ser Glu Glu Leu Cys
        645                 650                 655 gtg cgc tgg acc cag ttg ggg gcc ttc tac ccc ttc atg cgg aac cac        2192
Val Arg Trp Thr Gln Leu Gly Ala Phe Tyr Pro Phe Met Arg Asn His
    660                 665                 670 aat gac ctg aat agc gtg cct cag gag ccg tac agg ttc agc gag acg        2240
Asn Asp Leu Asn Ser Val Pro Gln Glu Pro Tyr Arg Phe Ser Glu Thr
675                 680                 685                 690 gcg cag cag gcc atg agg aag gcc ttc gcc tta cgc tat gcc ctt ctg        2288
Ala Gln Gln Ala Met Arg Lys Ala Phe Ala Leu Arg Tyr Ala Leu Leu
                695                 700                 705
```

| | | |
|---|---|---|
| ccc tac ctg tac act ctc ttc cac cgc gcc cac gtc aga gga gac acg<br>Pro Tyr Leu Tyr Thr Leu Phe His Arg Ala His Val Arg Gly Asp Thr<br>710     715     720 | | 2336 |
| gtg gcc cgg ccc ctc ttc ctg gag ttc cct gag gat ccc agc acc tgg<br>Val Ala Arg Pro Leu Phe Leu Glu Phe Pro Glu Asp Pro Ser Thr Trp<br>  725     730     735 | | 2384 |
| tct gtg gac cgc cag ctc ttg tgg ggg ccg gcc ctg ctc atc aca cct<br>Ser Val Asp Arg Gln Leu Leu Trp Gly Pro Ala Leu Leu Ile Thr Pro<br>740     745     750 | | 2432 |
| gtg ctt gag cct ggg aaa act gaa gtg acg ggc tac ttc ccc aag ggc<br>Val Leu Glu Pro Gly Lys Thr Glu Val Thr Gly Tyr Phe Pro Lys Gly<br>755     760      765     770 | | 2480 |
| acg tgg tac aac atg cag atg gtg tca gtg gat ccc ctc ggt act ctc<br>Thr Trp Tyr Asn Met Gln Met Val Ser Val Asp Ser Leu Gly Thr Leu<br>    775     780     785 | | 2528 |
| cct tct cca tca tcg gct tca tcc ttc aga tct gct gtc cag agc aag<br>Pro Ser Pro Ser Ser Ala Ser Ser Phe Arg Ser Ala Val Gln Ser Lys<br>  790     795     800 | | 2576 |
| ggg cag tgg ctg aca ctg gaa gcc cca ctg gat acc atc aac gtg cac<br>Gly Gln Trp Leu Thr Leu Glu Ala Pro Leu Asp Thr Ile Asn Val His<br>805     810     815 | | 2624 |
| ctg agg gag ggg tac atc ata ccg ctg cag ggt ccc agc ctc aca acc<br>Leu Arg Glu Gly Tyr Ile Ile Pro Leu Gln Gly Pro Ser Leu Thr Thr<br>820     825     830 | | 2672 |
| acg gag tcc cga aag cag ccc atg gct ctg gct gtg gca tta aca gca<br>Thr Glu Ser Arg Lys Gln Pro Met Ala Leu Ala Val Ala Leu Thr Ala<br>835     840     845     850 | | 2720 |
| agc ggc gag gcc gat ggg gag ctg ttc tgg gac gac ggg gag agc ctc<br>Ser Gly Glu Ala Asp Gly Glu Leu Phe Trp Asp Asp Gly Glu Ser Leu<br>    855     860     865 | | 2768 |
| gcg gtt ctg gag cgt ggg gcc tac aca ctg gtc acc ttc tca gcc aag<br>Ala Val Leu Glu Arg Gly Ala Tyr Thr Leu Val Thr Phe Ser Ala Lys<br>870     875     880 | | 2816 |
| aac aat acc att gtg aac aag tta gtg cgt gtg acc aag gag gga gct<br>Asn Asn Thr Ile Val Asn Lys Leu Val Arg Val Thr Lys Glu Gly Ala<br>  885     890     895 | | 2864 |
| gag cta caa ctg agg gag gtg acc gtc ttg gga gtg gcc aca gct cct<br>Glu Leu Gln Leu Arg Glu Val Thr Val Leu Gly Val Ala Thr Ala Pro<br>900     905     910 | | 2912 |
| acc cag gtc ctt tcc aac ggc atc cct gtc tcc aat ttc acc tac agc<br>Thr Gln Val Leu Ser Asn Gly Ile Pro Val Ser Asn Phe Thr Tyr Ser<br>915     920     925     930 | | 2960 |
| cct gac aac aag agc ctg gcc atc cct gtc tca ctg ctg atg gga gag<br>Pro Asp Asn Lys Ser Leu Ala Ile Pro Val Ser Leu Leu Met Gly Glu<br>    935     940     945 | | 3008 |
| ctg ttt caa atc agc tgg tcc tag gagagtccgt cgtttacaga ggcctccagg<br>Leu Phe Gln Ile Ser Trp Ser<br>950 | | 3062 |
| gaggcagagg gagcttgagc tggctctggc tggtggctcc tgtaaggacc tgcgtcctgc | | 3122 |
| tctcctgaca catctttgag cttttcccac cgtgttactg catgcgcccc tgaagctctg | | 3182 |
| tgttcttagg agagtgaggc tcgcctcacc tgccccaccc cagctgtctg tccctcacct | | 3242 |
| ggcactagag aatgtggagc tcggcgtggg gacatcgtgt ctgcaccaac atcaggctgt | | 3302 |
| gcagccactg cagccgcaac cctgcagaga cagagctggt gccttcacca ggttcccaag | | 3362 |
| actcgagaaa cttactgtga agtgtactta cttttaataa aaaggatatt gtttggaagc | | 3422 |
| agttctcacg tcacctcatg tctatatatg acctttgtgt cacatctcta aacaccctca | | 3482 |
| ggtccccatg tcacctcagg tttgcttatt cccccccccc cttttttttt tgttttttcca | | 3542 |

```
gacagggttt ctctgtgtgg ccctggctgt cctggaactc acttgtagac caggctggcc    3602
tcgaactcag aaagctgcct gcctctgcct cccaagtgct ggaattaaag gtgtgtgcta    3662
ccac                                                                 3666

<210> SEQ ID NO 2
<211> LENGTH: 953
<212> TYPE: PRT
<213> ORGANISM: Mus musculus

<400> SEQUENCE: 2
```

| Met | Asn | Ile | Arg | Lys | Pro | Leu | Cys | Ser | Asn | Ser | Val | Val | Gly | Ala | Cys |
|---|---|---|---|---|---|---|---|---|---|---|---|---|---|---|---|
| 1 | | | | 5 | | | | | 10 | | | | | 15 | |

| Thr | Leu | Ile | Ser | Leu | Thr | Thr | Ala | Val | Ile | Leu | Gly | His | Leu | Met | Leu |
|---|---|---|---|---|---|---|---|---|---|---|---|---|---|---|---|
| | | | 20 | | | | | 25 | | | | | 30 | | |

| Arg | Glu | Leu | Met | Leu | Leu | Pro | Gln | Asp | Leu | His | Glu | Ser | Ser | Ser | Gly |
| | | | 35 | | | | | 40 | | | | | 45 | | |

| Leu | Trp | Lys | Thr | Tyr | Arg | Pro | His | His | Gln | Glu | Gly | Tyr | Lys | Pro | Gly |
| | 50 | | | | | 55 | | | | | 60 | | | | |

| Pro | Leu | His | Ile | Gln | Glu | Gln | Thr | Glu | Gln | Pro | Lys | Glu | Ala | Pro | Thr |
| 65 | | | | | 70 | | | | | 75 | | | | | 80 |

| Gln | Cys | Asp | Val | Pro | Pro | Ser | Ser | Arg | Phe | Asp | Cys | Ala | Pro | Asp | Lys |
| | | | | 85 | | | | | 90 | | | | | 95 | |

| Gly | Ile | Ser | Gln | Glu | Gln | Cys | Glu | Ala | Arg | Gly | Cys | Cys | Tyr | Val | Pro |
| | | | 100 | | | | | 105 | | | | | 110 | | |

| Ala | Gly | Gln | Val | Leu | Lys | Glu | Pro | Gln | Ile | Gly | Gln | Pro | Trp | Cys | Phe |
| | | | 115 | | | | | 120 | | | | | 125 | | |

| Phe | Pro | Pro | Ser | Tyr | Pro | Ser | Tyr | Arg | Leu | Glu | Asn | Leu | Ser | Ser | Thr |
| 130 | | | | | 135 | | | | | 140 | | | | | |

| Glu | Ser | Gly | Tyr | Thr | Ala | Thr | Leu | Thr | Arg | Thr | Ser | Pro | Thr | Phe | Phe |
| 145 | | | | | 150 | | | | | 155 | | | | | 160 |

| Pro | Lys | Asp | Val | Leu | Thr | Leu | Gln | Leu | Glu | Val | Leu | Met | Glu | Thr | Asp |
| | | | | 165 | | | | | 170 | | | | | 175 | |

| Ser | Arg | Leu | His | Phe | Lys | Ile | Lys | Asp | Pro | Ala | Ser | Lys | Arg | Tyr | Glu |
| | | | 180 | | | | | 185 | | | | | 190 | | |

| Val | Pro | Leu | Glu | Thr | Pro | Arg | Val | Leu | Ser | Gln | Ala | Pro | Ser | Pro | Leu |
| | | | 195 | | | | | 200 | | | | | 205 | | |

| Tyr | Ser | Val | Glu | Phe | Ser | Glu | Glu | Pro | Phe | Gly | Val | Ile | Val | Arg | Arg |
| 210 | | | | | 215 | | | | | 220 | | | | | |

| Lys | Leu | Gly | Gly | Arg | Val | Leu | Leu | Asn | Thr | Thr | Val | Ala | Pro | Leu | Phe |
| 225 | | | | | 230 | | | | | 235 | | | | | 240 |

| Phe | Ala | Asp | Gln | Phe | Leu | Gln | Leu | Ser | Thr | Ser | Leu | Pro | Ser | Gln | His |
| | | | | 245 | | | | | 250 | | | | | 255 | |

| Ile | Thr | Gly | Leu | Gly | Glu | His | Leu | Ser | Pro | Leu | Met | Leu | Ser | Thr | Asp |
| | | | 260 | | | | | 265 | | | | | 270 | | |

| Trp | Ala | Arg | Ile | Thr | Leu | Trp | Asn | Arg | Asp | Thr | Pro | Pro | Ser | Gln | Gly |
| | | | 275 | | | | | 280 | | | | | 285 | | |

| Thr | Asn | Leu | Tyr | Gly | Ser | His | Pro | Phe | Tyr | Leu | Ala | Leu | Glu | Asp | Gly |
| | | | 290 | | | | | 295 | | | | | 300 | | |

| Gly | Leu | Ala | His | Gly | Val | Phe | Leu | Leu | Asn | Ser | Asn | Ala | Met | Asp | Val |
| 305 | | | | | 310 | | | | | 315 | | | | | 320 |

| Ile | Leu | Gln | Pro | Ser | Pro | Ala | Leu | Thr | Trp | Arg | Ser | Thr | Gly | Gly | Ile |
| | | | | 325 | | | | | 330 | | | | | 335 | |

| Leu | Asp | Val | Tyr | Val | Phe | Leu | Gly | Pro | Glu | Pro | Lys | Ser | Val | Val | Gln |
| | | | 340 | | | | | 345 | | | | | 350 | | |

-continued

```
Gln Tyr Leu Asp Val Val Gly Tyr Pro Phe Met Pro Pro Tyr Trp Gly
            355                 360                 365
Leu Gly Phe His Leu Cys Arg Trp Gly Tyr Ser Ser Thr Ala Ile Val
        370                 375                 380
Arg Gln Val Val Glu Asn Met Thr Arg Thr His Phe Pro Leu Asp Val
385                 390                 395                 400
Gln Trp Asn Asp Leu Asp Tyr Met Asp Ala Arg Arg Asp Phe Thr Phe
                405                 410                 415
Asn Gln Asp Ser Phe Ala Asp Phe Pro Asp Met Val Arg Glu Leu His
            420                 425                 430
Gln Asp Gly Arg Arg Tyr Met Met Ile Val Asp Pro Ala Ile Ser Ser
        435                 440                 445
Ala Gly Pro Ala Gly Ser Tyr Arg Pro Tyr Asp Glu Gly Leu Arg Arg
450                 455                 460
Gly Val Phe Ile Thr Asn Glu Thr Gly Gln Pro Leu Ile Gly Lys Val
465                 470                 475                 480
Trp Pro Gly Thr Thr Ala Phe Pro Asp Phe Thr Asn Pro Glu Thr Leu
                485                 490                 495
Asp Trp Trp Gln Asp Met Val Ser Glu Phe His Ala Gln Val Pro Phe
            500                 505                 510
Asp Gly Met Trp Leu Asp Met Asn Glu Pro Ser Asn Phe Val Arg Gly
        515                 520                 525
Ser Gln Gln Gly Cys Pro Asn Asn Glu Leu Glu Asn Pro Pro Tyr Val
    530                 535                 540
Pro Gly Val Val Gly Gly Ile Leu Gln Ala Ala Thr Ile Cys Ala Ser
545                 550                 555                 560
Ser His Gln Phe Leu Ser Thr His Tyr Asn Leu His Asn Leu Tyr Gly
                565                 570                 575
Leu Thr Glu Ala Ile Ala Ser Ser Arg Ala Leu Val Lys Thr Arg Gly
            580                 585                 590
Thr Arg Pro Phe Val Ile Ser Arg Ser Thr Phe Ser Gly His Gly Arg
        595                 600                 605
Tyr Ala Gly His Trp Thr Gly Asp Val Arg Ser Ser Trp Glu His Leu
    610                 615                 620
Ala Tyr Ser Val Pro Asp Ile Leu Gln Phe Asn Leu Leu Gly Val Pro
625                 630                 635                 640
Leu Val Gly Ala Asp Ile Cys Gly Phe Ile Gly Asp Thr Ser Glu Glu
                645                 650                 655
Leu Cys Val Arg Trp Thr Gln Leu Gly Ala Phe Tyr Pro Phe Met Arg
            660                 665                 670
Asn His Asn Asp Leu Asn Ser Val Pro Gln Glu Pro Tyr Arg Phe Ser
        675                 680                 685
Glu Thr Ala Gln Gln Ala Met Arg Lys Ala Phe Ala Leu Arg Tyr Ala
    690                 695                 700
Leu Leu Pro Tyr Leu Tyr Thr Leu Phe His Arg Ala His Val Arg Gly
705                 710                 715                 720
Asp Thr Val Ala Arg Pro Leu Phe Leu Glu Phe Pro Glu Asp Pro Ser
                725                 730                 735
Thr Trp Ser Val Asp Arg Gln Leu Leu Trp Gly Pro Ala Leu Leu Ile
            740                 745                 750
Thr Pro Val Leu Glu Pro Gly Lys Thr Glu Val Thr Gly Tyr Phe Pro
        755                 760                 765
Lys Gly Thr Trp Tyr Asn Met Gln Met Val Ser Val Asp Ser Leu Gly
```

|  |  |  |  |  |  |  |  |  |  |  |  |  |  |
|---|---|---|---|---|---|---|---|---|---|---|---|---|---|
| | | | 770 | | | 775 | | | | 780 | | | |
| Thr | Leu | Pro | Ser | Pro | Ser | Ser | Ala | Ser | Ser | Phe | Arg | Ser | Ala | Val | Gln |
| 785 | | | | | 790 | | | | | 795 | | | | | 800 |

Ser Lys Gly Gln Trp Leu Thr Leu Glu Ala Pro Leu Asp Thr Ile Asn
                805                810              815

Val His Leu Arg Glu Gly Tyr Ile Ile Pro Leu Gln Gly Pro Ser Leu
         820              825                830

Thr Thr Thr Glu Ser Arg Lys Gln Pro Met Ala Leu Ala Val Ala Leu
        835              840               845

Thr Ala Ser Gly Glu Ala Asp Gly Glu Leu Phe Trp Asp Asp Gly Glu
    850               855               860

Ser Leu Ala Val Leu Glu Arg Gly Ala Tyr Thr Leu Val Thr Phe Ser
865                870              875              880

Ala Lys Asn Asn Thr Ile Val Asn Lys Leu Arg Val Thr Lys Glu
                885              890              895

Gly Ala Glu Leu Gln Leu Arg Glu Val Thr Val Leu Gly Val Ala Thr
            900                905              910

Ala Pro Thr Gln Val Leu Ser Asn Gly Ile Pro Val Ser Asn Phe Thr
        915              920               925

Tyr Ser Pro Asp Asn Lys Ser Leu Ala Ile Pro Val Ser Leu Leu Met
930                935              940

Gly Glu Leu Phe Gln Ile Ser Trp Ser
945                950

<210> SEQ ID NO 3
<211> LENGTH: 2352
<212> TYPE: DNA
<213> ORGANISM: Mus musculus
<220> FEATURE:
<221> NAME/KEY: CDS
<222> LOCATION: (286)..(1113)

<400> SEQUENCE: 3

| | |
|---|---|
| gagggtgact ggacctacgg tgggcgcccg gcgctgcggt tcactctggt tccgagggcg | 60 |
| gaagtgcccg tcgggctgtt ttctgacccg ggcggcagca ctgtgcggct gcgcgcgcac | 120 |
| tgggacttct gctcctgcgc ctctgcagga cagtgtgatc ccggcagaca gaacccgacc | 180 |
| gagcggcttt cgcgctgcgg gaagccggag cagagccggc acctcggttt ggctttggtt | 240 |
| gaaggaagaa cttagcctat atgtactgct tcatccactg gaaga atg aca gat gac | 297 |
|                                                             Met Thr Asp Asp<br>                                                               1 | |
| aaa gat gtg ctt cga gat gtg tgg ttt gga cga att cca act tgc ttt<br>Lys Asp Val Leu Arg Asp Val Trp Phe Gly Arg Ile Pro Thr Cys Phe<br>5                    10                  15                   20 | 345 |
| act ctc tat cag gat gag ata act gaa aga gaa gca gaa cca tac tat<br>Thr Leu Tyr Gln Asp Glu Ile Thr Glu Arg Glu Ala Glu Pro Tyr Tyr<br>                       25                   30                   35 | 393 |
| ttg ctt ttg cca aga gtc agc tat ttg acg ttg gta act gac aaa gtg<br>Leu Leu Leu Pro Arg Val Ser Tyr Leu Thr Leu Val Thr Asp Lys Val<br>        40                   45                   50 | 441 |
| aaa aag cac ttt cag aag gtt atg aga caa gaa gat gtt agt gag ata<br>Lys Lys His Phe Gln Lys Val Met Arg Gln Glu Asp Val Ser Glu Ile<br>55                    60                  65 | 489 |
| tgg ttt gaa tat gaa ggc aca ccc ctg aaa tgg cat tat cca att ggt<br>Trp Phe Glu Tyr Glu Gly Thr Pro Leu Lys Trp His Tyr Pro Ile Gly<br>      70                   75                   80 | 537 |
| tta cta ttt gat ctt ctt gca tca agt tca gct ctt cct tgg aac atc<br>Leu Leu Phe Asp Leu Leu Ala Ser Ser Ser Ala Leu Pro Trp Asn Ile | 585 |

```
                     85                  90                  95                 100
aca gta cat ttc aag agt ttt cca gaa aag gac ctt cta cac tgt cca             633
Thr Val His Phe Lys Ser Phe Pro Glu Lys Asp Leu Leu His Cys Pro
                    105                 110                 115 tcc aag gat gcg gtt gag gct cac ttt atg tcg tgt atg aaa gaa gct             681
Ser Lys Asp Ala Val Glu Ala His Phe Met Ser Cys Met Lys Glu Ala
            120                 125                 130 gat gct tta aag cat aaa agt caa gtg atc aac gaa atg cag aaa aaa             729
Asp Ala Leu Lys His Lys Ser Gln Val Ile Asn Glu Met Gln Lys Lys
        135                 140                 145 gac cac aag cag ctc tgg atg gga ctg cag aat gac aga ttt gac cag             777
Asp His Lys Gln Leu Trp Met Gly Leu Gln Asn Asp Arg Phe Asp Gln
    150                 155                 160 ttt tgg gcc atc aac cgg aaa ctc atg gaa tat cct cca gaa gaa aat             825
Phe Trp Ala Ile Asn Arg Lys Leu Met Glu Tyr Pro Pro Glu Glu Asn
165                 170                 175                 180 gga ttt cgt tat atc ccc ttt aga ata tat cag acc acg acg gag cgg             873
Gly Phe Arg Tyr Ile Pro Phe Arg Ile Tyr Gln Thr Thr Thr Glu Arg
                185                 190                 195 cct ttc atc cag aag ctg ttc cgg cct gtg gcc gca gat gga cag ctg             921
Pro Phe Ile Gln Lys Leu Phe Arg Pro Val Ala Ala Asp Gly Gln Leu
            200                 205                 210 cac aca ctt gga gat ctc ctc aga gaa gtc tgt cct tcc gca gtc gcc             969
His Thr Leu Gly Asp Leu Leu Arg Glu Val Cys Pro Ser Ala Val Ala
        215                 220                 225 cct gaa gat gga gag aag agg agc cag gtg atg att cac ggg ata gag            1017
Pro Glu Asp Gly Glu Lys Arg Ser Gln Val Met Ile His Gly Ile Glu
    230                 235                 240 cca atg ctg gaa acc cct ctg cag tgg ctg agc gag cat ctg agc tac            1065
Pro Met Leu Glu Thr Pro Leu Gln Trp Leu Ser Glu His Leu Ser Tyr
245                 250                 255                 260 cca gat aac ttt ctt cat att agc att gtc ccc cag cca aca gat tga            1113
Pro Asp Asn Phe Leu His Ile Ser Ile Val Pro Gln Pro Thr Asp
                265                 270                 275 aagagtgtgt cctcctcgct agatggaacc accttgagtc aggacaacga ggcgtgacac          1173
ccttgcttca gtcaagttca gtggaggcaa cagaaacccg ggctgctgca agccaaggag          1233
gagaagattc catgagagat agggcgcccg ggcagggctg agtgtgcacc actgcttcgc          1293
tgagacacac aggaccactg cagcctcctc ttctcgtgaa atgcaatgca gccgaagcct          1353
ttgctcaatg aaaaaaaaaa aaatggaaat gtgccacagt ttgtatttct gattaacaaa          1413
taagtggggt atttcctaag gtgaccatgg tggaacctta gcaggagaa tggaaacatt           1473
ggttgaattt tcaatagaat tagacttaag aaagtaaaag agaaattctg ttattaataa          1533
cttgcagtaa ttttttttgta aaagatcaaa ttacagtaaa cccatctttc cttaatgaga         1593
ctttcctgtt tacagtcagt ctattggtat gcaaacaatc ttgtaacttt gataatgaac          1653
agtgagagat ttttaaataa agcctctaac tatgttttgt catttaataa catacagttt         1713
gtcactttc aaagacctcc tgaatctcat agagtaagcc acttttttctt ctgtgttccc         1773
atttctcact ggcatagcaa gggtgcgggg cataaggcga cttgtctcag gagctgtcac         1833
aggatttatt actgtgactt gaaaaatctg tcttctatat actaaaggta taaataatcc        1893
tatctgtctt tgctgttacg ttggtcactg taaacctgtc aaatcatagt atgccaagta        1953
tctgtctatg ataattttttg aatattttga atctcccgtt cctttccagt gttttttgttt      2013
ggtttggttt tggtttttttg ttttacgttt ttgtttttttg gctcctggat tatgtcattg      2073
tggcccctgg cagccagtct ttaaagcctg caggtgacct gtctctagac tgcagtagct        2133
```

```
tttccttatc attaccaaaa acatccagag gttactggaa ctcctaccac agtaaggaaa   2193
gtttgctgca ctctctcgat ggctgcttgg agactcctgc tgttgatttg tgagctagct   2253
tgctgtccac attgaatgtc aacccatctg agtatgctaa agatgatat cataaaataa   2313 tggttctaga ttcaataata aagatgaatg ttttcttat                         2352
```

<210> SEQ ID NO 4
<211> LENGTH: 275
<212> TYPE: PRT
<213> ORGANISM: Mus musculus

<400> SEQUENCE: 4

```
Met Thr Asp Asp Lys Asp Val Leu Arg Asp Val Trp Phe Gly Arg Ile
1               5                   10                  15

Pro Thr Cys Phe Thr Leu Tyr Gln Asp Glu Ile Thr Glu Arg Glu Ala
            20                  25                  30

Glu Pro Tyr Tyr Leu Leu Pro Arg Val Ser Tyr Leu Thr Leu Val
        35                  40                  45

Thr Asp Lys Val Lys Lys His Phe Gln Lys Val Met Arg Gln Glu Asp
    50                  55                  60

Val Ser Glu Ile Trp Phe Glu Tyr Glu Gly Thr Pro Leu Lys Trp His
65                  70                  75                  80

Tyr Pro Ile Gly Leu Leu Phe Asp Leu Leu Ala Ser Ser Ala Leu
                85                  90                  95

Pro Trp Asn Ile Thr Val His Phe Lys Ser Phe Pro Glu Lys Asp Leu
            100                 105                 110

Leu His Cys Pro Ser Lys Asp Ala Val Glu Ala His Phe Met Ser Cys
        115                 120                 125

Met Lys Glu Ala Asp Ala Leu Lys His Lys Ser Gln Val Ile Asn Glu
    130                 135                 140

Met Gln Lys Lys Asp His Lys Gln Leu Trp Met Gly Leu Gln Asn Asp
145                 150                 155                 160

Arg Phe Asp Gln Phe Trp Ala Ile Asn Arg Lys Leu Met Glu Tyr Pro
                165                 170                 175

Pro Glu Glu Asn Gly Phe Arg Tyr Ile Pro Phe Arg Ile Tyr Gln Thr
            180                 185                 190

Thr Thr Glu Arg Pro Phe Ile Gln Lys Leu Phe Arg Pro Val Ala Ala
        195                 200                 205

Asp Gly Gln Leu His Thr Leu Gly Asp Leu Leu Arg Glu Val Cys Pro
    210                 215                 220

Ser Ala Val Ala Pro Glu Asp Gly Glu Lys Arg Ser Gln Val Met Ile
225                 230                 235                 240

His Gly Ile Glu Pro Met Leu Glu Thr Pro Leu Gln Trp Leu Ser Glu
                245                 250                 255

His Leu Ser Tyr Pro Asp Asn Phe Leu His Ile Ser Ile Val Pro Gln
            260                 265                 270

Pro Thr Asp
        275
```

<210> SEQ ID NO 5
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 5

| | | |
|---|---|---|
| atg gaa ggg tct aag acg tcc aac aac agc acc atg cag gtg agc ttc<br>Met Glu Gly Ser Lys Thr Ser Asn Asn Ser Thr Met Gln Val Ser Phe<br>1               5                   10                  15 | | 48 |
| gtg tgc cag cgc tgc agc cag ccc ctg aaa ctg gac acg agt ttc aag<br>Val Cys Gln Arg Cys Ser Gln Pro Leu Lys Leu Asp Thr Ser Phe Lys<br>            20                  25                  30 | | 96 |
| atc ctg gac cgt gtc acc atc cag gaa ctc aca gct cca tta ctt acc<br>Ile Leu Asp Arg Val Thr Ile Gln Glu Leu Thr Ala Pro Leu Leu Thr<br>        35                  40                  45 | | 144 |
| aca gcc cag gcg aaa cca gga gag acc cag gag gaa gag act aac tca<br>Thr Ala Gln Ala Lys Pro Gly Glu Thr Gln Glu Glu Glu Thr Asn Ser<br>    50                  55                  60 | | 192 |
| gga gag gag cca ttt att gaa act cct cgc cag gat ggt gtc tct cgc<br>Gly Glu Glu Pro Phe Ile Glu Thr Pro Arg Gln Asp Gly Val Ser Arg<br>65                  70                  75                  80 | | 240 |
| aga ttc atc ccc cca gcc agg atg atg tcc aca gaa agt gcc aac agc<br>Arg Phe Ile Pro Pro Ala Arg Met Met Ser Thr Glu Ser Ala Asn Ser<br>                85                  90                  95 | | 288 |
| ttc act ctg att ggg gag gca tct gat ggc ggc acc atg gag aac ctc<br>Phe Thr Leu Ile Gly Glu Ala Ser Asp Gly Gly Thr Met Glu Asn Leu<br>            100                 105                 110 | | 336 |
| agc cga aga ctg aag gtc act ggg gac ctt ttt gac atc atg tcg ggc<br>Ser Arg Arg Leu Lys Val Thr Gly Asp Leu Phe Asp Ile Met Ser Gly<br>        115                 120                 125 | | 384 |
| cag aca gat gtg gat cac cca ctc tgt gag gaa tgc aca gat act ctt<br>Gln Thr Asp Val Asp His Pro Leu Cys Glu Glu Cys Thr Asp Thr Leu<br>    130                 135                 140 | | 432 |
| tta gac cag ctg gac act cag ctc aac gtc act gaa aat gag tgt cag<br>Leu Asp Gln Leu Asp Thr Gln Leu Asn Val Thr Glu Asn Glu Cys Gln<br>145                 150                 155                 160 | | 480 |
| aac tac aaa cgc tgt ttg gag atc tta gag caa atg aat gag gat gac<br>Asn Tyr Lys Arg Cys Leu Glu Ile Leu Glu Gln Met Asn Glu Asp Asp<br>                165                 170                 175 | | 528 |
| agt gaa cag tta cag atg gag cta aag gag ctg gca cta gag gag gag<br>Ser Glu Gln Leu Gln Met Glu Leu Lys Glu Leu Ala Leu Glu Glu Glu<br>            180                 185                 190 | | 576 |
| agg ctg atc cag gag ctg gaa gac gtg gaa aag aac cgc aag ata gtg<br>Arg Leu Ile Gln Glu Leu Glu Asp Val Glu Lys Asn Arg Lys Ile Val<br>        195                 200                 205 | | 624 |
| gca gaa aat ctc gag aag gtc cag gct gag gct gag aga ctg gat cag<br>Ala Glu Asn Leu Glu Lys Val Gln Ala Glu Ala Glu Arg Leu Asp Gln<br>    210                 215                 220 | | 672 |
| gag gaa gct cag tat cag aga gaa tac agt gaa ttt aaa cga cag cag<br>Glu Glu Ala Gln Tyr Gln Arg Glu Tyr Ser Glu Phe Lys Arg Gln Gln<br>225                 230                 235                 240 | | 720 |
| ctg gag ctg gat gat gag ctg aag agt gtt gaa aac cag atg cgt tat<br>Leu Glu Leu Asp Asp Glu Leu Lys Ser Val Glu Asn Gln Met Arg Tyr<br>                245                 250                 255 | | 768 |
| gcc cag acg cag ctg gat aag ctg aag aaa acc aac gtc ttt aat gca<br>Ala Gln Thr Gln Leu Asp Lys Leu Lys Lys Thr Asn Val Phe Asn Ala<br>            260                 265                 270 | | 816 |
| acc ttc cac atc tgg cac agt gga cag ttt ggc aca atc aat aac ttc<br>Thr Phe His Ile Trp His Ser Gly Gln Phe Gly Thr Ile Asn Asn Phe<br>        275                 280                 285 | | 864 |
| agg ctg ggt cgc ctg ccc agt gtt ccc gtg gaa tgg aat gag att aat<br>Arg Leu Gly Arg Leu Pro Ser Val Pro Val Glu Trp Asn Glu Ile Asn<br>    290                 295                 300 | | 912 |
| gct gct tgg ggc cag act gtg ttg ctg ctc cat gct ctg gcc aat aag<br>Ala Ala Trp Gly Gln Thr Val Leu Leu Leu His Ala Leu Ala Asn Lys<br>305                 310                 315                 320 | | 960 |

```
atg ggt ctg aaa ttt cag aga tac cga ctt gtt cct tac gga aac cat    1008
Met Gly Leu Lys Phe Gln Arg Tyr Arg Leu Val Pro Tyr Gly Asn His
            325                 330                 335 tca tat ctg gag tct ctg aca gac aaa tct aag gag ctg ccg tta tac    1056
Ser Tyr Leu Glu Ser Leu Thr Asp Lys Ser Lys Glu Leu Pro Leu Tyr
        340                 345                 350 tgt tct ggg ggg ttg cgg ttt ttc tgg gac aac aag ttt gac cat gca    1104
Cys Ser Gly Gly Leu Arg Phe Phe Trp Asp Asn Lys Phe Asp His Ala
    355                 360                 365 atg gtg gct ttc ctg gac tgt gtg cag cag ttc aaa gaa gag gtt gag    1152
Met Val Ala Phe Leu Asp Cys Val Gln Gln Phe Lys Glu Glu Val Glu
370                 375                 380 aaa ggc gag aca cgt ttt tgt ctt ccc tac agg atg gat gtg gag aaa    1200
Lys Gly Glu Thr Arg Phe Cys Leu Pro Tyr Arg Met Asp Val Glu Lys
385                 390                 395                 400 ggc aag att gaa gac aca gga ggc agt ggc ggc tcc tat tcc atc aaa    1248
Gly Lys Ile Glu Asp Thr Gly Gly Ser Gly Gly Ser Tyr Ser Ile Lys
            405                 410                 415 acc cag ttt aac tct gag gag cag tgg aca aaa gct ctc aag ttc atg    1296
Thr Gln Phe Asn Ser Glu Glu Gln Trp Thr Lys Ala Leu Lys Phe Met
        420                 425                 430 ctg acg aat ctt aag tgg ggt ctt gct tgg gtg tcc tca caa ttt tat    1344
Leu Thr Asn Leu Lys Trp Gly Leu Ala Trp Val Ser Ser Gln Phe Tyr
    435                 440                 445 aac aaa tga                                                        1353
Asn Lys
    450

<210> SEQ ID NO 6
<211> LENGTH: 450
<212> TYPE: PRT
<213> ORGANISM: Homo sapiens

<400> SEQUENCE: 6

Met Glu Gly Ser Lys Thr Ser Asn Asn Ser Thr Met Gln Val Ser Phe
1               5                   10                  15

Val Cys Gln Arg Cys Ser Gln Pro Leu Lys Leu Asp Thr Ser Phe Lys
            20                  25                  30

Ile Leu Asp Arg Val Thr Ile Gln Glu Leu Thr Ala Pro Leu Leu Thr
        35                  40                  45

Thr Ala Gln Ala Lys Pro Gly Glu Thr Gln Glu Glu Thr Asn Ser
    50                  55                  60

Gly Glu Glu Pro Phe Ile Glu Thr Pro Arg Gln Asp Gly Val Ser Arg
65                  70                  75                  80

Arg Phe Ile Pro Pro Ala Arg Met Met Ser Thr Glu Ser Ala Asn Ser
                85                  90                  95

Phe Thr Leu Ile Gly Glu Ala Ser Asp Gly Gly Thr Met Glu Asn Leu
            100                 105                 110

Ser Arg Arg Leu Lys Val Thr Gly Asp Leu Phe Asp Ile Met Ser Gly
        115                 120                 125

Gln Thr Asp Val Asp His Pro Leu Cys Glu Glu Cys Thr Asp Thr Leu
    130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
                165                 170                 175

Ser Glu Gln Leu Gln Met Glu Leu Lys Glu Leu Ala Leu Glu Glu Glu
            180                 185                 190
```

```
Arg Leu Ile Gln Glu Leu Glu Asp Val Glu Lys Asn Arg Lys Ile Val
            195                 200                 205
Ala Glu Asn Leu Glu Lys Val Gln Ala Glu Ala Glu Arg Leu Asp Gln
    210                 215                 220
Glu Glu Ala Gln Tyr Gln Arg Glu Tyr Ser Glu Phe Lys Arg Gln Gln
225                 230                 235                 240
Leu Glu Leu Asp Asp Glu Leu Lys Ser Val Glu Asn Gln Met Arg Tyr
                245                 250                 255
Ala Gln Thr Gln Leu Asp Lys Leu Lys Lys Thr Asn Val Phe Asn Ala
            260                 265                 270
Thr Phe His Ile Trp His Ser Gly Gln Phe Gly Thr Ile Asn Asn Phe
        275                 280                 285
Arg Leu Gly Arg Leu Pro Ser Val Pro Val Glu Trp Asn Glu Ile Asn
    290                 295                 300
Ala Ala Trp Gly Gln Thr Val Leu Leu Leu His Ala Leu Ala Asn Lys
305                 310                 315                 320
Met Gly Leu Lys Phe Gln Arg Tyr Arg Leu Val Pro Tyr Gly Asn His
                325                 330                 335
Ser Tyr Leu Glu Ser Leu Thr Asp Lys Ser Lys Glu Leu Pro Leu Tyr
            340                 345                 350
Cys Ser Gly Gly Leu Arg Phe Phe Trp Asp Asn Lys Phe Asp His Ala
        355                 360                 365
Met Val Ala Phe Leu Asp Cys Val Gln Gln Phe Lys Glu Glu Val Glu
    370                 375                 380
Lys Gly Glu Thr Arg Phe Cys Leu Pro Tyr Arg Met Asp Val Glu Lys
385                 390                 395                 400
Gly Lys Ile Glu Asp Thr Gly Gly Ser Gly Ser Tyr Ser Ile Lys
                405                 410                 415
Thr Gln Phe Asn Ser Glu Glu Leu Trp Thr Lys Ala Leu Lys Phe Met
            420                 425                 430
Leu Thr Asn Leu Lys Trp Gly Leu Ala Trp Val Ser Ser Gln Phe Tyr
        435                 440                 445
Asn Lys
    450

<210> SEQ ID NO 7
<211> LENGTH: 3059
<212> TYPE: DNA
<213> ORGANISM: Mus musculus
<220> FEATURE:
<221> NAME/KEY: CDS
<222> LOCATION: (50)..(2146)

<400> SEQUENCE: 7 gggctgtgg ttgccggaag ttgagcggcg gctggtaaga acagtagcc atg ggg gac      58
                                                    Met Gly Asp
                                                      1 cct gga ctg gcc aag ttg cag ttc gcc ccc ttt aat agt gcc ctg gac     106
Pro Gly Leu Ala Lys Leu Gln Phe Ala Pro Phe Asn Ser Ala Leu Asp
  5                  10                  15 gtt ggc ttc tgg cac gaa ctg acc cag aag aag ttg aac gag tac cgc     154
Val Gly Phe Trp His Glu Leu Thr Gln Lys Lys Leu Asn Glu Tyr Arg
20                  25                  30                  35 ctg gac gag gca ccc aaa gac atc aag ggc tat tac tac aat ggt gac     202
Leu Asp Glu Ala Pro Lys Asp Ile Lys Gly Tyr Tyr Tyr Asn Gly Asp
                40                  45                  50 tct gct ggt ctg ccc acc cgc ttg acg ttg gag ttc agt gct ttt gac     250
```

```
Ser Ala Gly Leu Pro Thr Arg Leu Thr Leu Glu Phe Ser Ala Phe Asp
            55                  60                  65 atg agt gcc tcc acg cct gcc cac tgc tgc ccg gcc atg gga acc ctg        298
Met Ser Ala Ser Thr Pro Ala His Cys Cys Pro Ala Met Gly Thr Leu
            70                  75                  80 cac aac acc aac aca ctt gag gct ttt aag aca gca gac aag aag ctc        346
His Asn Thr Asn Thr Leu Glu Ala Phe Lys Thr Ala Asp Lys Lys Leu
            85                  90                  95 ctt ctg gag cag tca gca aat gag atc tgg gaa gcc ata aag tca ggt        394
Leu Leu Glu Gln Ser Ala Asn Glu Ile Trp Glu Ala Ile Lys Ser Gly
100             105                 110                 115 gct gct ctc gaa aac ccc atg ctc ctc aac aag ttt ctg ctc ctg acc        442
Ala Ala Leu Glu Asn Pro Met Leu Leu Asn Lys Phe Leu Leu Leu Thr
                120                 125                 130 ttc gcg gac cta aag aag tac cac ttc tac tac tgg ttt tgc tgc ccc        490
Phe Ala Asp Leu Lys Lys Tyr His Phe Tyr Tyr Trp Phe Cys Cys Pro
                135                 140                 145 gcc ctc tgt ctt cct gag agc atc cct cta atc cgg gga cct gtg agc        538
Ala Leu Cys Leu Pro Glu Ser Ile Pro Leu Ile Arg Gly Pro Val Ser
                150                 155                 160 ttg gat caa agg ctt tca cca aaa cag atc cag gcc ctg gag cat gcc        586
Leu Asp Gln Arg Leu Ser Pro Lys Gln Ile Gln Ala Leu Glu His Ala
165             170                 175 tat gat gat ctg tgt cga gcc gaa ggc gtc acg gcc ctg ccc tac ttc        634
Tyr Asp Asp Leu Cys Arg Ala Glu Gly Val Thr Ala Leu Pro Tyr Phe
180             185                 190                 195 tta ttc aag tac gat gac gac act gtt ctg gtc tcc ttg ctc aaa cac        682
Leu Phe Lys Tyr Asp Asp Asp Thr Val Leu Val Ser Leu Leu Lys His
                200                 205                 210 tac agt gat ttc ttc caa ggt caa agg aca aag ata aca gtt ggt gtg        730
Tyr Ser Asp Phe Phe Gln Gly Gln Arg Thr Lys Ile Thr Val Gly Val
                215                 220                 225 tac gat ccc tgt aac cta gcc cag tac cct gga tgg cct ttg agg aat        778
Tyr Asp Pro Cys Asn Leu Ala Gln Tyr Pro Gly Trp Pro Leu Arg Asn
                230                 235                 240 ttt ttg gtc ctg gca gcc cac aga tgg agc ggc agt ttc cag tcc gtt        826
Phe Leu Val Leu Ala Ala His Arg Trp Ser Gly Ser Phe Gln Ser Val
245                 250                 255 gaa gtc ctc tgc ttt cgg gac cgc acc atg cag gga gct aga gac gtg        874
Glu Val Leu Cys Phe Arg Asp Arg Thr Met Gln Gly Ala Arg Asp Val
260                 265                 270                 275 aca cat agc atc atc ttt gaa gtg aaa ctt cca gaa atg gca ttt agc        922
Thr His Ser Ile Ile Phe Glu Val Lys Leu Pro Glu Met Ala Phe Ser
                280                 285                 290 cca gat tgt cct aaa gct gtt ggc tgg gag aag aac cag aaa gga ggc        970
Pro Asp Cys Pro Lys Ala Val Gly Trp Glu Lys Asn Gln Lys Gly Gly
                295                 300                 305 atg ggt ccg agg atg gtg aac ctc agt gga tgt atg gac ccc aaa agg       1018
Met Gly Pro Arg Met Val Asn Leu Ser Gly Cys Met Asp Pro Lys Arg
                310                 315                 320 ctg gct gag tca tct gtg gat ctg aat ctc aag ctg atg tgc tgg cga       1066
Leu Ala Glu Ser Ser Val Asp Leu Asn Leu Lys Leu Met Cys Trp Arg
325                 330                 335 ttg gtc ccc acc ttg gac ttg gac aag gtc gtg tct gtc aag tgc ctg       1114
Leu Val Pro Thr Leu Asp Leu Asp Lys Val Val Ser Val Lys Cys Leu
340             345                 350                 355 ctg ctg gga gct ggt acc ttg ggg tgt aat gtg gct agg aca ctg atg       1162
Leu Leu Gly Ala Gly Thr Leu Gly Cys Asn Val Ala Arg Thr Leu Met
                360                 365                 370 ggc tgg ggc gtc aga cat gtc acc ttt gtg gat aac gcc aag atc tcc       1210
```

-continued

| | | |
|---|---|---|
| Gly Trp Gly Val Arg His Val Thr Phe Val Asp Asn Ala Lys Ile Ser<br>375                        380                    385 | | |
| tac tcc aat ccc gtg agg cag cct ctg tat gaa ttt gaa gat tgt cta<br>Tyr Ser Asn Pro Val Arg Gln Pro Leu Tyr Glu Phe Glu Asp Cys Leu<br>        390                    395                    400 | 1258 |
| ggg ggt ggc aag ccc aag gcc ctg gct gca gca gag cgg cta cag aaa<br>Gly Gly Gly Lys Pro Lys Ala Leu Ala Ala Ala Glu Arg Leu Gln Lys<br>405                        410                    415 | 1306 |
| ata ttt ccc gga gtg aat gcc aga ggg ttc aac atg agc atc ccc atg<br>Ile Phe Pro Gly Val Asn Ala Arg Gly Phe Asn Met Ser Ile Pro Met<br>420                        425                    430                    435 | 1354 |
| cca gga cac cct gtg aac ttc tct gac gtc acg atg gag cag gcc cgc<br>Pro Gly His Pro Val Asn Phe Ser Asp Val Thr Met Glu Gln Ala Arg<br>                440                    445                    450 | 1402 |
| aga gat gtg gag cag ctg gag cag ctc att gat aac cat gat gtc atc<br>Arg Asp Val Glu Gln Leu Glu Gln Leu Ile Asp Asn His Asp Val Ile<br>                    455                    460                    465 | 1450 |
| ttc ctg cta atg gac acc agg gag agc cgg tgg ctt cct act gtt att<br>Phe Leu Leu Met Asp Thr Arg Glu Ser Arg Trp Leu Pro Thr Val Ile<br>            470                    475                    480 | 1498 |
| gca gcc agc aag cga aag ctg gtc atc aac gct gcc ttg ggg ttt gat<br>Ala Ala Ser Lys Arg Lys Leu Val Ile Asn Ala Ala Leu Gly Phe Asp<br>485                        490                    495 | 1546 |
| acc ttt gtt gtc atg aga cat ggc ctg aag aaa ccc aag cag cag gga<br>Thr Phe Val Val Met Arg His Gly Leu Lys Lys Pro Lys Gln Gln Gly<br>500                        505                    510                    515 | 1594 |
| gcc gga gac ctc tgc cca agc cat ctt gta gca cct gct gac ctg ggc<br>Ala Gly Asp Leu Cys Pro Ser His Leu Val Ala Pro Ala Asp Leu Gly<br>                520                    525                    530 | 1642 |
| tcc tca ctt ttt gcc aac atc cct gga tac aag ctt ggc tgc tac ttc<br>Ser Ser Leu Phe Ala Asn Ile Pro Gly Tyr Lys Leu Gly Cys Tyr Phe<br>            535                    540                    545 | 1690 |
| tgc aat gat gtg gtg gct cca gga gat tca acc aga gac cgg act ctg<br>Cys Asn Asp Val Val Ala Pro Gly Asp Ser Thr Arg Asp Arg Thr Leu<br>550                        555                    560 | 1738 |
| gac cag cag tgc aca gtg agc cgc cca ggc ctg gcc gtg att gca ggt<br>Asp Gln Gln Cys Thr Val Ser Arg Pro Gly Leu Ala Val Ile Ala Gly<br>            565                    570                    575 | 1786 |
| gcc ctg gct gtg gag ctg atg gtc tct gtc ctg cag cat cct gag ggg<br>Ala Leu Ala Val Glu Leu Met Val Ser Val Leu Gln His Pro Glu Gly<br>580                        585                    590                    595 | 1834 |
| ggc tac gcc atc gcc agc agc agt gat gac cgc atg aat gag cct ccc<br>Gly Tyr Ala Ile Ala Ser Ser Ser Asp Asp Arg Met Asn Glu Pro Pro<br>                600                    605                    610 | 1882 |
| acc tcg ctg gga ctt gtg cct cac cag atc cgg ggt ttt ctg tca cgg<br>Thr Ser Leu Gly Leu Val Pro His Gln Ile Arg Gly Phe Leu Ser Arg<br>            615                    620                    625 | 1930 |
| ttc gat aat gtt ctt cct gtc agc ctg gca ttt gat aaa tgt aca gcc<br>Phe Asp Asn Val Leu Pro Val Ser Leu Ala Phe Asp Lys Cys Thr Ala<br>            630                    635                    640 | 1978 |
| tgt tca ccc aaa gtt ctt gat cag tac gag cga gaa gga ttc acc ttc<br>Cys Ser Pro Lys Val Leu Asp Gln Tyr Glu Arg Glu Gly Phe Thr Phe<br>645                        650                    655 | 2026 |
| cta gcg aag gtt ttt aac tcc tca cat tcc ttc tta gaa gac ttg acc<br>Leu Ala Lys Val Phe Asn Ser Ser His Ser Phe Leu Glu Asp Leu Thr<br>660                        665                    670                    675 | 2074 |
| ggt ctt acc ctg ctc cat caa gag acc caa gct gct gag atc tgg gac<br>Gly Leu Thr Leu Leu His Gln Glu Thr Gln Ala Ala Glu Ile Trp Asp<br>                680                    685                    690 | 2122 |
| atg agt gac gag gag act gtc tga agcaagcaac cacagctcag gagtacctgg<br>Met Ser Asp Glu Glu Thr Val | 2176 |

Met Ser Asp Glu Glu Thr Val
        695

| | |
|---|---|
| ccctcagcgc aggactggac cgcaggactg gtgatctggg ccctgccacc tccctggtcc | 2236 |
| tgatctccac atctccaagg acgagggtgt accctctgcc acccagttgc acccttttcct | 2296 |
| gtgccatctc accagctctg aactcaataa taaccttggc attgccactg atctggggct | 2356 |
| caggtccttc catgtgcact aatctccccc cccccacaca cacactgttg ctgaaggaca | 2416 |
| ccccaggacc caacatagat cagacaaggc tgtgctagga gcctcaccgg tagggcacct | 2476 |
| gctctgggcc ctgggtagca gtgagtgctg agtttgtagc ctcaagtgtt caagtggcac | 2536 |
| accaagccac cctcccccag ctgtgggcat gctgtgtgcc accctgttcc agggatggga | 2596 |
| gaagctcctg ccacagccct gtactgaaaa gcagggaaga gctctgtagg atgggtgtgt | 2656 |
| ccagctgggc ctagtcaggt gccctcactc acggggttgc tcctggggca aggcttgtct | 2716 |
| tcctcttcac tctgggtggg cccttggcag ctgtggccac ccatcctaaa tagatgagct | 2776 |
| gctcccctcc cacacctgtg caccttcact ggggtctcag gtccgaaaca gaagcccatg | 2836 |
| cacggctggc ttagcaggtc tcaggaaggg agactagaga ggaccttggc ctaacacaga | 2896 |
| tgctgcaaca gcggcccta ccatctgtgc aaggctcccc acaagtagcc aggcctacct | 2956 |
| gggcacaggg ccccacagcc cacatgccac cctaggagtc aagagccaca cagcctcggt | 3016 |
| ttaagagcac tttattattg ttcttaaggc tacttttaag tac | 3059 |

<210> SEQ ID NO 8
<211> LENGTH: 698
<212> TYPE: PRT
<213> ORGANISM: Mus musculus

<400> SEQUENCE: 8

Met Gly Asp Pro Gly Leu Ala Lys Leu Gln Phe Ala Pro Phe Asn Ser
1               5                   10                  15

Ala Leu Asp Val Gly Phe Trp His Glu Leu Thr Gln Lys Lys Leu Asn
            20                  25                  30

Glu Tyr Arg Leu Asp Glu Ala Pro Lys Asp Ile Lys Gly Tyr Tyr Tyr
        35                  40                  45

Asn Gly Asp Ser Ala Gly Leu Pro Thr Arg Leu Thr Leu Glu Phe Ser
    50                  55                  60

Ala Phe Asp Met Ser Ala Ser Thr Pro Ala His Cys Cys Pro Ala Met
65                  70                  75                  80

Gly Thr Leu His Asn Thr Asn Thr Leu Glu Ala Phe Lys Thr Ala Asp
                85                  90                  95

Lys Lys Leu Leu Leu Glu Gln Ser Ala Asn Glu Ile Trp Glu Ala Ile
            100                 105                 110

Lys Ser Gly Ala Ala Leu Glu Asn Pro Met Leu Leu Asn Lys Phe Leu
        115                 120                 125

Leu Leu Thr Phe Ala Asp Leu Lys Lys Tyr His Phe Tyr Tyr Trp Phe
    130                 135                 140

Cys Cys Pro Ala Leu Cys Leu Pro Glu Ser Ile Pro Leu Ile Arg Gly
145                 150                 155                 160

Pro Val Ser Leu Asp Gln Arg Leu Ser Pro Lys Gln Ile Gln Ala Leu
                165                 170                 175

Glu His Ala Tyr Asp Asp Leu Cys Arg Ala Gly Val Thr Ala Leu
            180                 185                 190

Pro Tyr Phe Leu Phe Lys Tyr Asp Asp Asp Thr Val Leu Val Ser Leu
        195                 200                 205

-continued

```
Leu Lys His Tyr Ser Asp Phe Phe Gln Gly Gln Arg Thr Lys Ile Thr
    210                 215                 220
Val Gly Val Tyr Asp Pro Cys Asn Leu Ala Gln Tyr Pro Gly Trp Pro
225                 230                 235                 240
Leu Arg Asn Phe Leu Val Leu Ala Ala His Arg Trp Ser Gly Ser Phe
                245                 250                 255
Gln Ser Val Glu Val Leu Cys Phe Arg Asp Arg Thr Met Gln Gly Ala
            260                 265                 270
Arg Asp Val Thr His Ser Ile Ile Phe Glu Val Lys Leu Pro Glu Met
        275                 280                 285
Ala Phe Ser Pro Asp Cys Pro Lys Ala Val Gly Trp Glu Lys Asn Gln
290                 295                 300
Lys Gly Gly Met Gly Pro Arg Met Val Asn Leu Ser Gly Cys Met Asp
305                 310                 315                 320
Pro Lys Arg Leu Ala Glu Ser Ser Val Asp Leu Asn Leu Lys Leu Met
                325                 330                 335
Cys Trp Arg Leu Val Pro Thr Leu Asp Leu Asp Lys Val Val Ser Val
                340                 345                 350
Lys Cys Leu Leu Leu Gly Ala Gly Thr Leu Gly Cys Asn Val Ala Arg
            355                 360                 365
Thr Leu Met Gly Trp Gly Val Arg His Val Thr Phe Val Asp Asn Ala
    370                 375                 380
Lys Ile Ser Tyr Ser Asn Pro Val Arg Gln Pro Leu Tyr Glu Phe Glu
385                 390                 395                 400
Asp Cys Leu Gly Gly Lys Pro Lys Ala Leu Ala Ala Ala Glu Arg
                405                 410                 415
Leu Gln Lys Ile Phe Pro Gly Val Asn Ala Arg Gly Phe Asn Met Ser
                420                 425                 430
Ile Pro Met Pro Gly His Pro Val Asn Phe Ser Asp Val Thr Met Glu
    435                 440                 445
Gln Ala Arg Arg Asp Val Glu Gln Leu Glu Gln Leu Ile Asp Asn His
    450                 455                 460
Asp Val Ile Phe Leu Leu Met Asp Thr Arg Glu Ser Arg Trp Leu Pro
465                 470                 475                 480
Thr Val Ile Ala Ala Ser Lys Arg Lys Leu Val Ile Asn Ala Ala Leu
                485                 490                 495
Gly Phe Asp Thr Phe Val Val Met Arg His Gly Leu Lys Lys Pro Lys
                500                 505                 510
Gln Gln Gly Ala Gly Asp Leu Cys Pro Ser His Leu Val Ala Pro Ala
            515                 520                 525
Asp Leu Gly Ser Ser Leu Phe Ala Asn Ile Pro Gly Tyr Lys Leu Gly
530                 535                 540
Cys Tyr Phe Cys Asn Asp Val Val Ala Pro Gly Asp Ser Thr Arg Asp
545                 550                 555                 560
Arg Thr Leu Asp Gln Gln Cys Thr Val Ser Arg Pro Gly Leu Ala Val
                565                 570                 575
Ile Ala Gly Ala Leu Ala Val Glu Leu Met Val Ser Val Leu Gln His
                580                 585                 590
Pro Glu Gly Gly Tyr Ala Ile Ala Ser Ser Asp Asp Arg Met Asn
            595                 600                 605
Glu Pro Pro Thr Ser Leu Gly Leu Val Pro His Gln Ile Arg Gly Phe
    610                 615                 620
Leu Ser Arg Phe Asp Asn Val Leu Pro Val Ser Leu Ala Phe Asp Lys
625                 630                 635                 640
```

```
Cys Thr Ala Cys Ser Pro Lys Val Leu Asp Gln Tyr Glu Arg Glu Gly
            645                 650                 655

Phe Thr Phe Leu Ala Lys Val Phe Asn Ser His Ser Phe Leu Glu
            660                 665                 670

Asp Leu Thr Gly Leu Thr Leu Leu His Gln Glu Thr Gln Ala Ala Glu
            675                 680                 685

Ile Trp Asp Met Ser Asp Glu Glu Thr Val
            690                 695

<210> SEQ ID NO 9
<211> LENGTH: 2775
<212> TYPE: DNA
<213> ORGANISM: Homo sapiens
<220> FEATURE:
<221> NAME/KEY: CDS
<222> LOCATION: (1)..(2775)

<400> SEQUENCE: 9 atg gtg agc cga atg ggc tgg ggg ggg aga aga agg cgg ctg ggg cgg      48
Met Val Ser Arg Met Gly Trp Gly Gly Arg Arg Arg Arg Leu Gly Arg
1               5                   10                  15 tgg gga gat ctg ggg ccc gga tcg gtg ccc ctc ctc ccc atg cca ctg      96
Trp Gly Asp Leu Gly Pro Gly Ser Val Pro Leu Leu Pro Met Pro Leu
                20                  25                  30 cca cct cct cct cct cct tca tgc cgg gga cct ggg gga ggg agg atc     144
Pro Pro Pro Pro Pro Pro Ser Cys Arg Gly Pro Gly Gly Gly Arg Ile
            35                  40                  45 tcc atc ttc tct ctg tcc cct gcc cct cat aca aga agc tcc ccc tcc     192
Ser Ile Phe Ser Leu Ser Pro Ala Pro His Thr Arg Ser Ser Pro Ser
        50                  55                  60 tca ttt tcc cct ccc acc gca ggg ccc cct tgc tca gtg cta cag ggg     240
Ser Phe Ser Pro Pro Thr Ala Gly Pro Pro Cys Ser Val Leu Gln Gly
65                  70                  75                  80 aca ggg gct tct cag tct tgc cac agt gct ctc cct atc cca gcc acc     288
Thr Gly Ala Ser Gln Ser Cys His Ser Ala Leu Pro Ile Pro Ala Thr
                85                  90                  95 ccc cca aca cag gct caa cct gca atg aca cct gcc tct gca tct ccc     336
Pro Pro Thr Gln Ala Gln Pro Ala Met Thr Pro Ala Ser Ala Ser Pro
            100                 105                 110 tcc tgg gga tcc cac tcc acc cca ccc ctg gcc ccg gca acc ccc act     384
Ser Trp Gly Ser His Ser Thr Pro Pro Leu Ala Pro Ala Thr Pro Thr
        115                 120                 125 ccc tca cag cag tgc ccc cag gac tct cct ggg ctg cgg gta ggc cct     432
Pro Ser Gln Gln Cys Pro Gln Asp Ser Pro Gly Leu Arg Val Gly Pro
    130                 135                 140 ttg atc cct gaa cag gat tat gag cgg ctg gag gac tgt gac cct gag     480
Leu Ile Pro Glu Gln Asp Tyr Glu Arg Leu Glu Asp Cys Asp Pro Glu
145                 150                 155                 160 ggg tcc caa gac tca ccc atc cac ggg gag gag cag caa ccc ctg ctt     528
Gly Ser Gln Asp Ser Pro Ile His Gly Glu Glu Gln Gln Pro Leu Leu
                165                 170                 175 cat gtc cct gaa ggg ctc cga ggc tcc tgg cat cac atc cag aac ctg     576
His Val Pro Glu Gly Leu Arg Gly Ser Trp His His Ile Gln Asn Leu
            180                 185                 190 gac agt ttc ttc acc aag atc tac agc tac cac cag cgg aat ggc ttt     624
Asp Ser Phe Phe Thr Lys Ile Tyr Ser Tyr His Gln Arg Asn Gly Phe
        195                 200                 205 gcc tgc atc ttg ctg gag gat gtc ttc cag ctg gga caa ttt att ttc     672
Ala Cys Ile Leu Leu Glu Asp Val Phe Gln Leu Gly Gln Phe Ile Phe
    210                 215                 220
```

```
att gtc acc ttc aca acc ttc ctc ctt cga tgc gtg gat tac aat gtt      720
Ile Val Thr Phe Thr Thr Phe Leu Leu Arg Cys Val Asp Tyr Asn Val
225                 230                 235                 240 ctc ttt gcc aac caa cca agt aac cat acc aga cct ggg ccg ttc cac      768
Leu Phe Ala Asn Gln Pro Ser Asn His Thr Arg Pro Gly Pro Phe His
                245                 250                 255 agc aaa gtg acc ctg tca gat gcc atc cta ccc tca gcc cag tgt gct      816
Ser Lys Val Thr Leu Ser Asp Ala Ile Leu Pro Ser Ala Gln Cys Ala
            260                 265                 270 gag agg atc cgc tcc agc ccg ctg ctg gtc ctc ctg gtc ctg gct          864
Glu Arg Ile Arg Ser Ser Pro Leu Leu Val Leu Leu Val Leu Ala
        275                 280                 285 gcc ggc ttc tgg ctg gtc caa ctg ctt cgc tca gtc tgc aac ctc ttc      912
Ala Gly Phe Trp Leu Val Gln Leu Leu Arg Ser Val Cys Asn Leu Phe
290                 295                 300 agc tac tgg gac atc cag gtg ttt tac agg gag gcc ctg cac atc ccc      960
Ser Tyr Trp Asp Ile Gln Val Phe Tyr Arg Glu Ala Leu His Ile Pro
305                 310                 315                 320 ccg gag gag ctg agc tcg gtt ccc tgg gca gag gtg cag tcc cgc ctc     1008
Pro Glu Glu Leu Ser Ser Val Pro Trp Ala Glu Val Gln Ser Arg Leu
                325                 330                 335 ttg gca ctg cag cgg agc ggg ggc ctg tgc gtg cag ccg cgg ccc ctg     1056
Leu Ala Leu Gln Arg Ser Gly Gly Leu Cys Val Gln Pro Arg Pro Leu
            340                 345                 350 acg gag ctg gac atc cac cac cgc atc ctg cgc tac acc aac tac cag     1104
Thr Glu Leu Asp Ile His His Arg Ile Leu Arg Tyr Thr Asn Tyr Gln
        355                 360                 365 gtg gcg ctg gcc aac aaa ggc ctg ctg ccg gcc cgc tgc ccg ctg ccc     1152
Val Ala Leu Ala Asn Lys Gly Leu Leu Pro Ala Arg Cys Pro Leu Pro
    370                 375                 380 tgg gga ggc agt gcg gct ttc ctc agc cgc ggc ctg gcg ctc aat gtc     1200
Trp Gly Gly Ser Ala Ala Phe Leu Ser Arg Gly Leu Ala Leu Asn Val
385                 390                 395                 400 gac ctg ctg ctc ttc cgc ggt ccc ttc tcg ctc ttc cgc ggg ggc tgg     1248
Asp Leu Leu Leu Phe Arg Gly Pro Phe Ser Leu Phe Arg Gly Gly Trp
                405                 410                 415 gag ctg ccg cac gcc tac aag cgc agc gac cag cgg ggc gcc cta gca     1296
Glu Leu Pro His Ala Tyr Lys Arg Ser Asp Gln Arg Gly Ala Leu Ala
            420                 425                 430 gcg cgc tgg ggg cgc aca gtg ctg ctg ctg gcc gcc ctg aac ctg gcg     1344
Ala Arg Trp Gly Arg Thr Val Leu Leu Leu Ala Ala Leu Asn Leu Ala
        435                 440                 445 ctg agc ccg ctg gtg ctg gcc tgg cag gtt ctg cac gtc ttc tat agc     1392
Leu Ser Pro Leu Val Leu Ala Trp Gln Val Leu His Val Phe Tyr Ser
    450                 455                 460 cac gtg gag ctg ctg cgg cgc gag cct ggc gcg ctg ggg gcg cgc ggc     1440
His Val Glu Leu Leu Arg Arg Glu Pro Gly Ala Leu Gly Ala Arg Gly
465                 470                 475                 480 tgg tcc cgc ctg gcg cgc ttg cag ctg cgc cac ttc aac gag ctg ccg     1488
Trp Ser Arg Leu Ala Arg Leu Gln Leu Arg His Phe Asn Glu Leu Pro
                485                 490                 495 cac gag ctg cgc gcg cgc ctg gcc cgc gcc tac cgc ccc gcc gcc gcc     1536
His Glu Leu Arg Ala Arg Leu Ala Arg Ala Tyr Arg Pro Ala Ala Ala
            500                 505                 510 ttc ctg cgc acc gct gcg ccc ccc gcg ccc ctg cgc acg ctg ctg gcc     1584
Phe Leu Arg Thr Ala Ala Pro Pro Ala Pro Leu Arg Thr Leu Leu Ala
        515                 520                 525 cgc cag ctc gtt ttc ttc gcg ggt gca ctc ttc gcc gcg ctg ctt gtg     1632
Arg Gln Leu Val Phe Phe Ala Gly Ala Leu Phe Ala Ala Leu Leu Val
    530                 535                 540
```

```
ctc acc gtc tac gac gag gac gtg cta gcc gtg gag cac gtg ctc acc    1680
Leu Thr Val Tyr Asp Glu Asp Val Leu Ala Val Glu His Val Leu Thr
545                 550                 555                 560 gcc atg acc gcg ctc ggg gtc acc gcc acc gtc gcc agg tct ttc att    1728
Ala Met Thr Ala Leu Gly Val Thr Ala Thr Val Ala Arg Ser Phe Ile
                565                 570                 575 ccg gaa gag cag tgc cag ggt cgt gcg ccg cag ctc ctg ctg cag aca    1776
Pro Glu Glu Gln Cys Gln Gly Arg Ala Pro Gln Leu Leu Leu Gln Thr
        580                 585                 590 gcc ctg gcc cac atg cac tac ctc ccg gag gag ccc ggc ccc ggc ggc    1824
Ala Leu Ala His Met His Tyr Leu Pro Glu Glu Pro Gly Pro Gly Gly
    595                 600                 605 agg gac cgc gcc tac cgg cag atg gcg cag ctg ctg cag tac cga gcg    1872
Arg Asp Arg Ala Tyr Arg Gln Met Ala Gln Leu Leu Gln Tyr Arg Ala
610                 615                 620 gtc tcc ctc ctg gag gag ctc ctg tcc ccg ctc ctc acc ccg ctg ttt    1920
Val Ser Leu Leu Glu Glu Leu Leu Ser Pro Leu Leu Thr Pro Leu Phe
625                 630                 635                 640 ctg ctt ttc tgg ttc cgc cct cgt gcc ctg gag att atc gac ttt ttt    1968
Leu Leu Phe Trp Phe Arg Pro Arg Ala Leu Glu Ile Ile Asp Phe Phe
                645                 650                 655 cat cac ttc act gtg gat gtg gct ggg gtt ggg gac atc tgt tcc ttt    2016
His His Phe Thr Val Asp Val Ala Gly Val Gly Asp Ile Cys Ser Phe
        660                 665                 670 gcc ctt atg gat gtg aag cgc cac gga cac cct cag tgg ctc tcg gcg    2064
Ala Leu Met Asp Val Lys Arg His Gly His Pro Gln Trp Leu Ser Ala
    675                 680                 685 gga cag act gag gcc tcg ctg tct cag cgt gcg gag gac ggc aag act    2112
Gly Gln Thr Glu Ala Ser Leu Ser Gln Arg Ala Glu Asp Gly Lys Thr
690                 695                 700 gag ctt tct ttg atg cgg ttc tcc ctg gcg cat cca ctc tgg cgc ccc    2160
Glu Leu Ser Leu Met Arg Phe Ser Leu Ala His Pro Leu Trp Arg Pro
705                 710                 715                 720 cca ggg cac agc tct aag ttt ctt ggg cac ctc tgg ggc cga gta caa    2208
Pro Gly His Ser Ser Lys Phe Leu Gly His Leu Trp Gly Arg Val Gln
                725                 730                 735 caa gat gca gct gcc tgg ggt gcc acc tcg gct cgc ggc ccc tcc acc    2256
Gln Asp Ala Ala Ala Trp Gly Ala Thr Ser Ala Arg Gly Pro Ser Thr
        740                 745                 750 ccg ggg gtg ctc agc aac tgc acc tcg ccc ctg cct gag gcc ttc ctg    2304
Pro Gly Val Leu Ser Asn Cys Thr Ser Pro Leu Pro Glu Ala Phe Leu
    755                 760                 765 gcc aac ctc ttc gtg cac cct ctc ctg cct ccg aga gat ctg agc ccg    2352
Ala Asn Leu Phe Val His Pro Leu Leu Pro Pro Arg Asp Leu Ser Pro
770                 775                 780 aca gcc ccc tgt cca gct gcg gcc aca gcc agc ctc ctt gcc tcc att    2400
Thr Ala Pro Cys Pro Ala Ala Ala Thr Ala Ser Leu Leu Ala Ser Ile
785                 790                 795                 800 tcc cga att gcc cag gac ccc agc tct gtg tcc cca gga ggc act ggg    2448
Ser Arg Ile Ala Gln Asp Pro Ser Ser Val Ser Pro Gly Gly Thr Gly
                805                 810                 815 ggc cag aag ctg gcc cag ctc cca gaa ctt gct tct gcc gag atg agt    2496
Gly Gln Lys Leu Ala Gln Leu Pro Glu Leu Ala Ser Ala Glu Met Ser
        820                 825                 830 ctc cat gtc atc tac ctg cac cag ctt cac cag cag cag cag cag cag    2544
Leu His Val Ile Tyr Leu His Gln Leu His Gln Gln Gln Gln Gln Gln
    835                 840                 845 gag ccg tgg ggt gag gct gca gcc tcc atc ctg tcc agg ccc tgc tcc    2592
Glu Pro Trp Gly Glu Ala Ala Ala Ser Ile Leu Ser Arg Pro Cys Ser
850                 855                 860
```

```
agc ccc tca cag cca ccc tcg cct gat gag gag aag cca tcc tgg tca    2640
Ser Pro Ser Gln Pro Pro Ser Pro Asp Glu Glu Lys Pro Ser Trp Ser
865                 870                 875                 880 agt gac ggc tcc agt cct gcc tct agc ccc aga caa cag tgg gga acc    2688
Ser Asp Gly Ser Ser Pro Ala Ser Ser Pro Arg Gln Gln Trp Gly Thr
            885                 890                 895 cag aag gcc cgg aat ctg ttc ccc gga ggg ttt cag gtg acc aca gac    2736
Gln Lys Ala Arg Asn Leu Phe Pro Gly Gly Phe Gln Val Thr Thr Asp
900                 905                 910 acc cag aag gag cct gac cgg gcc tct tgc act gac tga                2775
Thr Gln Lys Glu Pro Asp Arg Ala Ser Cys Thr Asp
        915                 920

<210> SEQ ID NO 10
<211> LENGTH: 924
<212> TYPE: PRT
<213> ORGANISM: Homo sapiens

<400> SEQUENCE: 10

Met Val Ser Arg Met Gly Trp Gly Gly Arg Arg Arg Leu Gly Arg
1               5                   10                  15

Trp Gly Asp Leu Gly Pro Gly Ser Val Pro Leu Leu Pro Met Pro Leu
                20                  25                  30

Pro Pro Pro Pro Pro Pro Ser Cys Arg Gly Pro Gly Gly Gly Arg Ile
            35                  40                  45

Ser Ile Phe Ser Leu Ser Pro Ala Pro His Thr Arg Ser Ser Pro Ser
        50                  55                  60

Ser Phe Ser Pro Pro Thr Ala Gly Pro Pro Cys Ser Val Leu Gln Gly
65                  70                  75                  80

Thr Gly Ala Ser Gln Ser Cys His Ser Ala Leu Pro Ile Pro Ala Thr
                85                  90                  95

Pro Pro Thr Gln Ala Gln Pro Ala Met Thr Pro Ala Ser Ala Ser Pro
            100                 105                 110

Ser Trp Gly Ser His Ser Thr Pro Pro Leu Ala Pro Ala Thr Pro Thr
        115                 120                 125

Pro Ser Gln Gln Cys Pro Gln Asp Ser Pro Gly Leu Arg Val Gly Pro
    130                 135                 140

Leu Ile Pro Glu Gln Asp Tyr Glu Arg Leu Glu Asp Cys Asp Pro Glu
145                 150                 155                 160

Gly Ser Gln Asp Ser Pro Ile His Gly Glu Glu Gln Pro Leu Leu
                165                 170                 175

His Val Pro Glu Gly Leu Arg Gly Ser Trp His His Ile Gln Asn Leu
            180                 185                 190

Asp Ser Phe Phe Thr Lys Ile Tyr Ser Tyr His Gln Arg Asn Gly Phe
        195                 200                 205

Ala Cys Ile Leu Leu Glu Asp Val Phe Gln Leu Gly Gln Phe Ile Phe
    210                 215                 220

Ile Val Thr Phe Thr Thr Phe Leu Leu Arg Cys Val Asp Tyr Asn Val
225                 230                 235                 240

Leu Phe Ala Asn Gln Pro Ser Asn His Thr Arg Pro Gly Pro Phe His
                245                 250                 255

Ser Lys Val Thr Leu Ser Asp Ala Ile Leu Pro Ser Ala Gln Cys Ala
            260                 265                 270

Glu Arg Ile Arg Ser Ser Pro Leu Leu Val Leu Leu Val Leu Ala
        275                 280                 285

Ala Gly Phe Trp Leu Val Gln Leu Leu Arg Ser Val Cys Asn Leu Phe
    290                 295                 300
```

```
Ser Tyr Trp Asp Ile Gln Val Phe Tyr Arg Glu Ala Leu His Ile Pro
305                 310                 315                 320

Pro Glu Glu Leu Ser Ser Val Pro Trp Ala Glu Val Gln Ser Arg Leu
            325                 330                 335

Leu Ala Leu Gln Arg Ser Gly Gly Leu Cys Val Gln Pro Arg Pro Leu
                340                 345                 350

Thr Glu Leu Asp Ile His His Arg Ile Leu Arg Tyr Thr Asn Tyr Gln
            355                 360                 365

Val Ala Leu Ala Asn Lys Gly Leu Leu Pro Ala Arg Cys Pro Leu Pro
370                 375                 380

Trp Gly Gly Ser Ala Ala Phe Leu Ser Arg Gly Leu Ala Leu Asn Val
385                 390                 395                 400

Asp Leu Leu Leu Phe Arg Gly Pro Phe Ser Leu Phe Arg Gly Gly Trp
                405                 410                 415

Glu Leu Pro His Ala Tyr Lys Arg Ser Asp Gln Arg Gly Ala Leu Ala
            420                 425                 430

Ala Arg Trp Gly Arg Thr Val Leu Leu Leu Ala Leu Asn Leu Ala
                435                 440                 445

Leu Ser Pro Leu Val Leu Ala Trp Gln Val Leu His Val Phe Tyr Ser
450                 455                 460

His Val Glu Leu Arg Arg Glu Pro Gly Ala Leu Gly Ala Arg Gly
465                 470                 475                 480

Trp Ser Arg Leu Ala Arg Leu Gln Leu Arg His Phe Asn Glu Leu Pro
                485                 490                 495

His Glu Leu Arg Ala Arg Leu Ala Arg Ala Tyr Arg Pro Ala Ala Ala
            500                 505                 510

Phe Leu Arg Thr Ala Ala Pro Pro Ala Pro Leu Arg Thr Leu Leu Ala
            515                 520                 525

Arg Gln Leu Val Phe Phe Ala Gly Ala Leu Phe Ala Ala Leu Leu Val
530                 535                 540

Leu Thr Val Tyr Asp Glu Asp Val Leu Ala Val Glu His Val Leu Thr
545                 550                 555                 560

Ala Met Thr Ala Leu Gly Val Thr Ala Thr Val Ala Arg Ser Phe Ile
                565                 570                 575

Pro Glu Glu Gln Cys Gln Gly Arg Ala Pro Gln Leu Leu Leu Gln Thr
            580                 585                 590

Ala Leu Ala His Met His Tyr Leu Pro Glu Glu Pro Gly Pro Gly Gly
            595                 600                 605

Arg Asp Arg Ala Tyr Arg Gln Met Ala Gln Leu Leu Gln Tyr Arg Ala
610                 615                 620

Val Ser Leu Leu Glu Glu Leu Leu Ser Pro Leu Leu Thr Pro Leu Phe
625                 630                 635                 640

Leu Leu Phe Trp Phe Arg Pro Arg Ala Leu Glu Ile Ile Asp Phe Phe
                645                 650                 655

His His Phe Thr Val Asp Val Ala Gly Val Gly Asp Ile Cys Ser Phe
            660                 665                 670

Ala Leu Met Asp Val Lys Arg His Gly His Pro Gln Trp Leu Ser Ala
            675                 680                 685

Gly Gln Thr Glu Ala Ser Leu Ser Gln Arg Ala Glu Asp Gly Lys Thr
            690                 695                 700

Glu Leu Ser Leu Met Arg Phe Ser Leu Ala His Pro Leu Trp Arg Pro
705                 710                 715                 720

Pro Gly His Ser Ser Lys Phe Leu Gly His Leu Trp Gly Arg Val Gln
```

```
                              725                 730                 735
Gln Asp Ala Ala Ala Trp Gly Ala Thr Ser Ala Arg Gly Pro Ser Thr
            740                 745                 750

Pro Gly Val Leu Ser Asn Cys Thr Ser Pro Leu Pro Glu Ala Phe Leu
        755                 760                 765

Ala Asn Leu Phe Val His Pro Leu Leu Pro Arg Asp Leu Ser Pro
770                 775                 780

Thr Ala Pro Cys Pro Ala Ala Thr Ala Ser Leu Leu Ala Ser Ile
785                 790                 795                 800

Ser Arg Ile Ala Gln Asp Pro Ser Val Ser Pro Gly Gly Thr Gly
                805                 810                 815

Gly Gln Lys Leu Ala Gln Leu Pro Glu Leu Ala Ser Ala Glu Met Ser
            820                 825                 830

Leu His Val Ile Tyr Leu His Gln Leu His Gln Gln Gln Gln Gln Gln
                835                 840                 845

Glu Pro Trp Gly Glu Ala Ala Ser Ile Leu Ser Arg Pro Cys Ser
            850                 855                 860

Ser Pro Ser Gln Pro Pro Ser Pro Asp Glu Glu Lys Pro Ser Trp Ser
865                 870                 875                 880

Ser Asp Gly Ser Ser Pro Ala Ser Ser Pro Arg Gln Trp Gly Thr
                885                 890                 895

Gln Lys Ala Arg Asn Leu Phe Pro Gly Gly Phe Gln Val Thr Thr Asp
            900                 905                 910

Thr Gln Lys Glu Pro Asp Arg Ala Ser Cys Thr Asp
            915                 920

<210> SEQ ID NO 11
<211> LENGTH: 564
<212> TYPE: DNA
<213> ORGANISM: Homo sapiens
<220> FEATURE:
<221> NAME/KEY: CDS
<222> LOCATION: (1)..(564)

<400> SEQUENCE: 11 atg act agc cgg gaa cac caa gtt tca ctg tgt aat tgc gtc ccc cta    48
Met Thr Ser Arg Glu His Gln Val Ser Leu Cys Asn Cys Val Pro Leu
1               5                   10                  15 ctc cgg cgc ctc ctt tgc gac gct ccc tgg aga aaa gca cgc cca ctg    96
Leu Arg Arg Leu Leu Cys Asp Ala Pro Trp Arg Lys Ala Arg Pro Leu
                20                  25                  30 cac gcg ctc agt cgc tac ttc cgc tct cga gtg tct cca agc aag atg   144
His Ala Leu Ser Arg Tyr Phe Arg Ser Arg Val Ser Pro Ser Lys Met
            35                  40                  45 gcg gag gag ccg cag tct gtg ttg cag ctt cct act tca att gct gct   192
Ala Glu Glu Pro Gln Ser Val Leu Gln Leu Pro Thr Ser Ile Ala Ala
    50                  55                  60 gga ggg gaa gga ctt acg gat gtc tcc cca gaa aca acc acc ccg gag   240
Gly Gly Glu Gly Leu Thr Asp Val Ser Pro Glu Thr Thr Thr Pro Glu
65                  70                  75                  80 ccc ccg tct tcc gct gca gtt tcc ccg gga aca gag gaa cct gct ggc   288
Pro Pro Ser Ser Ala Ala Val Ser Pro Gly Thr Glu Glu Pro Ala Gly
                85                  90                  95 gac acc aag aaa aaa att gac att ttg cta aag gct gtg gga gac act   336
Asp Thr Lys Lys Lys Ile Asp Ile Leu Leu Lys Ala Val Gly Asp Thr
            100                 105                 110 cct att atg aaa aca aag aag tgg gca gta gag cga aca cga acc atc   384
Pro Ile Met Lys Thr Lys Lys Trp Ala Val Glu Arg Thr Arg Thr Ile
        115                 120                 125
```

```
caa gga ctc att gac ttc atc aaa aag ttt ctt aaa ctt gtg gcc tca      432
Gln Gly Leu Ile Asp Phe Ile Lys Lys Phe Leu Lys Leu Val Ala Ser
        130                 135                 140 gaa cag ttg ttt att tat gtg aat cag tcc ttt gct cct tcc cca gac      480
Glu Gln Leu Phe Ile Tyr Val Asn Gln Ser Phe Ala Pro Ser Pro Asp
145                 150                 155                 160 caa gaa gtt gga act ctc tat gag tgt ttt ggc agt gat ggt aaa ctg      528
Gln Glu Val Gly Thr Leu Tyr Glu Cys Phe Gly Ser Asp Gly Lys Leu
                165                 170                 175 gtt tta cat tac tgc aag tct cag gcg tgg gga tga                      564
Val Leu His Tyr Cys Lys Ser Gln Ala Trp Gly
            180                 185

<210> SEQ ID NO 12
<211> LENGTH: 187
<212> TYPE: PRT
<213> ORGANISM: Homo sapiens

<400> SEQUENCE: 12

Met Thr Ser Arg Glu His Gln Val Ser Leu Cys Asn Cys Val Pro Leu
1               5                   10                  15

Leu Arg Arg Leu Leu Cys Asp Ala Pro Trp Arg Lys Ala Arg Pro Leu
            20                  25                  30

His Ala Leu Ser Arg Tyr Phe Arg Ser Arg Val Ser Pro Ser Lys Met
        35                  40                  45

Ala Glu Glu Pro Gln Ser Val Leu Gln Leu Pro Thr Ser Ile Ala Ala
    50                  55                  60

Gly Gly Glu Gly Leu Thr Asp Val Ser Pro Glu Thr Thr Pro Glu
65                  70                  75                  80

Pro Pro Ser Ser Ala Ala Val Ser Pro Gly Thr Glu Glu Pro Ala Gly
                85                  90                  95

Asp Thr Lys Lys Lys Ile Asp Ile Leu Leu Lys Ala Val Gly Asp Thr
            100                 105                 110

Pro Ile Met Lys Thr Lys Lys Trp Ala Val Glu Arg Thr Arg Thr Ile
        115                 120                 125

Gln Gly Leu Ile Asp Phe Ile Lys Lys Phe Leu Lys Leu Val Ala Ser
    130                 135                 140

Glu Gln Leu Phe Ile Tyr Val Asn Gln Ser Phe Ala Pro Ser Pro Asp
145                 150                 155                 160

Gln Glu Val Gly Thr Leu Tyr Glu Cys Phe Gly Ser Asp Gly Lys Leu
                165                 170                 175

Val Leu His Tyr Cys Lys Ser Gln Ala Trp Gly
            180                 185

<210> SEQ ID NO 13
<211> LENGTH: 1824
<212> TYPE: DNA
<213> ORGANISM: Homo sapiens
<220> FEATURE:
<221> NAME/KEY: CDS
<222> LOCATION: (1)..(1824)

<400> SEQUENCE: 13 atg tcg tcg ggc ctc cgc gcc gct gac ttc ccc cgc tgg aag cgc cac      48
Met Ser Ser Gly Leu Arg Ala Ala Asp Phe Pro Arg Trp Lys Arg His
1               5                   10                  15 atc tcg gag caa ctg agg cgc cgg gac cgg ctg cag aga cag gcg ttc      96
Ile Ser Glu Gln Leu Arg Arg Arg Asp Arg Leu Gln Arg Gln Ala Phe
            20                  25                  30
```

```
gag gag atc atc ctg cag tat aac aaa ttg ctg gaa aag tca gat ctt      144
Glu Glu Ile Ile Leu Gln Tyr Asn Lys Leu Leu Glu Lys Ser Asp Leu
            35                  40                  45 cat tca gtg ttg gcc cag aaa cta cag gct gaa aag cat gac gta cca      192
His Ser Val Leu Ala Gln Lys Leu Gln Ala Glu Lys His Asp Val Pro
        50                  55                  60 aac agg cac gag ata agt ccc gga cat gat ggc aca tgg aat gac aat      240
Asn Arg His Glu Ile Ser Pro Gly His Asp Gly Thr Trp Asn Asp Asn
 65                 70                  75                  80 cag cta caa gaa atg gcc caa ctg agg att aag cac caa gag gaa ctg      288
Gln Leu Gln Glu Met Ala Gln Leu Arg Ile Lys His Gln Glu Glu Leu
                85                  90                  95 act gaa tta cac aag aaa cgt ggg gag tta gct caa ctg gtg att gac      336
Thr Glu Leu His Lys Lys Arg Gly Glu Leu Ala Gln Leu Val Ile Asp
           100                 105                 110 ctg aat aac caa atg cag cgg aag gac agg gag atg cag atg aat gaa      384
Leu Asn Asn Gln Met Gln Arg Lys Asp Arg Glu Met Gln Met Asn Glu
       115                 120                 125 gca aaa att gca gaa tgt ttg cag act atc tct gac ctg gag acg gag      432
Ala Lys Ile Ala Glu Cys Leu Gln Thr Ile Ser Asp Leu Glu Thr Glu
   130                 135                 140 tgc cta gac ctg cgc act aag ctt tgt gac ctt gaa aga gcc aac cag      480
Cys Leu Asp Leu Arg Thr Lys Leu Cys Asp Leu Glu Arg Ala Asn Gln
145                 150                 155                 160 acc ctg aag gat gaa tat gat gcc ctg cag atc act ttt act gcc ttg      528
Thr Leu Lys Asp Glu Tyr Asp Ala Leu Gln Ile Thr Phe Thr Ala Leu
                165                 170                 175 gag gga aaa ctg agg aaa act acg gaa gag aac cag gag ctg gtc acc      576
Glu Gly Lys Leu Arg Lys Thr Thr Glu Glu Asn Gln Glu Leu Val Thr
            180                 185                 190 aga tgg atg gct gag aaa gcc cag gaa gcc aat cgg ctt aat gca gag      624
Arg Trp Met Ala Glu Lys Ala Gln Glu Ala Asn Arg Leu Asn Ala Glu
        195                 200                 205 aat gaa aaa gac tcc agg agg cgg caa gcc cgg ctg cag aaa gag ctt      672
Asn Glu Lys Asp Ser Arg Arg Arg Gln Ala Arg Leu Gln Lys Glu Leu
210                 215                 220 gca gaa gca gca aag gaa cct cta cca gtc gaa cag gat gat gac att      720
Ala Glu Ala Ala Lys Glu Pro Leu Pro Val Glu Gln Asp Asp Asp Ile
225                 230                 235                 240 gag gtc att gtg gat gaa act tct gat cac aca gaa gag acc tct cct      768
Glu Val Ile Val Asp Glu Thr Ser Asp His Thr Glu Glu Thr Ser Pro
                245                 250                 255 gtg cga gcc atc agc aga gca gcc act aag cga ctc tcg cag cct gct      816
Val Arg Ala Ile Ser Arg Ala Ala Thr Lys Arg Leu Ser Gln Pro Ala
            260                 265                 270 gga ggc ctt ctg gat tct atc act aat atc ttt ggg aga cgc tct gtc      864
Gly Gly Leu Leu Asp Ser Ile Thr Asn Ile Phe Gly Arg Arg Ser Val
        275                 280                 285 tct tcc ttc cca gtc ccc cag gac aat gtg gat act cat cct ggt tct      912
Ser Ser Phe Pro Val Pro Gln Asp Asn Val Asp Thr His Pro Gly Ser
    290                 295                 300 ggt aaa gaa gtg agg gta cca gct act gcc ttg tgt gtc ttc gat gca      960
Gly Lys Glu Val Arg Val Pro Ala Thr Ala Leu Cys Val Phe Asp Ala
305                 310                 315                 320 cat gat ggg gaa gtc aac gct gtg cag ttc agt cca ggt tcc cgg tta     1008
His Asp Gly Glu Val Asn Ala Val Gln Phe Ser Pro Gly Ser Arg Leu
                325                 330                 335 ctg gcc act gga ggc atg gac cgc agg gtt aag ctt tgg gaa gta ttt     1056
Leu Ala Thr Gly Gly Met Asp Arg Arg Val Lys Leu Trp Glu Val Phe
            340                 345                 350
```

```
gga gaa aaa tgt gag ttc aag ggt tcc cta tct ggc agt aat gca gga    1104
Gly Glu Lys Cys Glu Phe Lys Gly Ser Leu Ser Gly Ser Asn Ala Gly
        355                 360                 365 att aca agc att gaa ttt gat agt gct gga tct tac ctc tta gca gct    1152
Ile Thr Ser Ile Glu Phe Asp Ser Ala Gly Ser Tyr Leu Leu Ala Ala
    370                 375                 380 tca aat gat ttt gca agc cga atc tgg act gtg gat gat tat cga tta    1200
Ser Asn Asp Phe Ala Ser Arg Ile Trp Thr Val Asp Asp Tyr Arg Leu
385                 390                 395                 400 cgg cac aca ctc acg gga cac agt ggg aaa gtg ctg tct gct aag ttc    1248
Arg His Thr Leu Thr Gly His Ser Gly Lys Val Leu Ser Ala Lys Phe
            405                 410                 415 ctg ctg gac aat gcg cgg att gtc tca gga agt cac gac cgg act ctc    1296
Leu Leu Asp Asn Ala Arg Ile Val Ser Gly Ser His Asp Arg Thr Leu
        420                 425                 430 aaa ctc tgg gat cta cgc agc aaa gtc tgc ata aag aca gtg ttt gca    1344
Lys Leu Trp Asp Leu Arg Ser Lys Val Cys Ile Lys Thr Val Phe Ala
    435                 440                 445 gga tcc agt tgc aat gat att gtc tgc aca gag caa tgt gta atg agt    1392
Gly Ser Ser Cys Asn Asp Ile Val Cys Thr Glu Gln Cys Val Met Ser
450                 455                 460 gga cat ttt gac aag aaa att cgt ttc tgg gac att cga tca gag agc    1440
Gly His Phe Asp Lys Lys Ile Arg Phe Trp Asp Ile Arg Ser Glu Ser
465                 470                 475                 480 ata gtt cga gag atg gag ctg ttg gga aag att act gcc ctg gac tta    1488
Ile Val Arg Glu Met Glu Leu Leu Gly Lys Ile Thr Ala Leu Asp Leu
            485                 490                 495 aac cca gaa agg act gag ctc ctg agc tgc tcc cgt gat gac ttg cta    1536
Asn Pro Glu Arg Thr Glu Leu Leu Ser Cys Ser Arg Asp Asp Leu Leu
        500                 505                 510 aaa gtt att gat ctc cga aca aat gct atc aag cag aca ttc agt gca    1584
Lys Val Ile Asp Leu Arg Thr Asn Ala Ile Lys Gln Thr Phe Ser Ala
    515                 520                 525 cct ggg ttc aag tgc ggc tct gac tgg acc aga gtt gtc ttc agc cct    1632
Pro Gly Phe Lys Cys Gly Ser Asp Trp Thr Arg Val Val Phe Ser Pro
530                 535                 540 gat ggc agt tac gtg gcg gca ggc tct gct gag ggc tct ctg tat atc    1680
Asp Gly Ser Tyr Val Ala Ala Gly Ser Ala Glu Gly Ser Leu Tyr Ile
545                 550                 555                 560 tgg agt gtg ctc aca ggg aaa gtg gaa aag gtt ctt tca aag cag cac    1728
Trp Ser Val Leu Thr Gly Lys Val Glu Lys Val Leu Ser Lys Gln His
            565                 570                 575 agc tca tcc atc aat gcg gtg gcg tgg tcg ccc tct ggc tcg cac gtt    1776
Ser Ser Ser Ile Asn Ala Val Ala Trp Ser Pro Ser Gly Ser His Val
        580                 585                 590 gtc agt gtg gac aaa gga tgc aaa gct gtg ctg tgg gca cag tac tga    1824
Val Ser Val Asp Lys Gly Cys Lys Ala Val Leu Trp Ala Gln Tyr
    595                 600                 605

<210> SEQ ID NO 14
<211> LENGTH: 607
<212> TYPE: PRT
<213> ORGANISM: Homo sapiens

<400> SEQUENCE: 14

Met Ser Ser Gly Leu Arg Ala Ala Asp Phe Pro Arg Trp Lys Arg His
1               5                   10                  15

Ile Ser Glu Gln Leu Arg Arg Arg Asp Arg Leu Gln Arg Gln Ala Phe
            20                  25                  30

Glu Glu Ile Ile Leu Gln Tyr Asn Lys Leu Leu Glu Lys Ser Asp Leu
        35                  40                  45
```

```
His Ser Val Leu Ala Gln Lys Leu Gln Ala Glu Lys His Asp Val Pro
    50                  55                  60
Asn Arg His Glu Ile Ser Pro Gly His Asp Gly Thr Trp Asn Asp Asn
 65                  70                  75                  80
Gln Leu Gln Glu Met Ala Gln Leu Arg Ile Lys His Gln Glu Glu Leu
                85                  90                  95
Thr Glu Leu His Lys Lys Arg Gly Glu Leu Ala Gln Leu Val Ile Asp
               100                 105                 110
Leu Asn Asn Gln Met Gln Arg Lys Asp Arg Glu Met Gln Met Asn Glu
           115                 120                 125
Ala Lys Ile Ala Glu Cys Leu Gln Thr Ile Ser Asp Leu Glu Thr Glu
       130                 135                 140
Cys Leu Asp Leu Arg Thr Lys Leu Cys Asp Leu Glu Arg Ala Asn Gln
145                 150                 155                 160
Thr Leu Lys Asp Glu Tyr Asp Ala Leu Gln Ile Thr Phe Thr Ala Leu
               165                 170                 175
Glu Gly Lys Leu Arg Lys Thr Thr Glu Glu Asn Gln Glu Leu Val Thr
           180                 185                 190
Arg Trp Met Ala Glu Lys Ala Gln Glu Ala Asn Arg Leu Asn Ala Glu
       195                 200                 205
Asn Glu Lys Asp Ser Arg Arg Arg Gln Ala Arg Leu Gln Lys Glu Leu
210                 215                 220
Ala Glu Ala Ala Lys Glu Pro Leu Pro Val Glu Gln Asp Asp Asp Ile
225                 230                 235                 240
Glu Val Ile Val Asp Glu Thr Ser Asp His Thr Glu Thr Ser Pro
               245                 250                 255
Val Arg Ala Ile Ser Arg Ala Ala Thr Lys Arg Leu Ser Gln Pro Ala
               260                 265                 270
Gly Gly Leu Leu Asp Ser Ile Thr Asn Ile Phe Gly Arg Arg Ser Val
           275                 280                 285
Ser Ser Phe Pro Val Pro Gln Asp Asn Val Asp Thr His Pro Gly Ser
       290                 295                 300
Gly Lys Glu Val Arg Val Pro Ala Thr Ala Leu Cys Val Phe Asp Ala
305                 310                 315                 320
His Asp Gly Glu Val Asn Ala Val Gln Phe Ser Pro Gly Ser Arg Leu
               325                 330                 335
Leu Ala Thr Gly Gly Met Asp Arg Arg Val Lys Leu Trp Glu Val Phe
           340                 345                 350
Gly Glu Lys Cys Glu Phe Lys Gly Ser Leu Ser Gly Ser Asn Ala Gly
       355                 360                 365
Ile Thr Ser Ile Glu Phe Asp Ser Ala Gly Ser Tyr Leu Leu Ala Ala
   370                 375                 380
Ser Asn Asp Phe Ala Ser Arg Ile Trp Thr Val Asp Asp Tyr Arg Leu
385                 390                 395                 400
Arg His Thr Leu Thr Gly His Ser Gly Lys Val Leu Ser Ala Lys Phe
               405                 410                 415
Leu Leu Asp Asn Ala Arg Ile Val Ser Gly Ser His Asp Arg Thr Leu
           420                 425                 430
Lys Leu Trp Asp Leu Arg Ser Lys Val Cys Ile Lys Thr Val Phe Ala
       435                 440                 445
Gly Ser Ser Cys Asn Asp Ile Val Cys Thr Glu Gln Cys Val Met Ser
450                 455                 460
Gly His Phe Asp Lys Lys Ile Arg Phe Trp Asp Ile Arg Ser Glu Ser
```

```
                465                 470                 475                 480
Ile Val Arg Glu Met Glu Leu Leu Gly Lys Ile Thr Ala Leu Asp Leu
                    485                 490                 495

Asn Pro Glu Arg Thr Glu Leu Leu Ser Cys Ser Arg Asp Asp Leu Leu
                500                 505                 510

Lys Val Ile Asp Leu Arg Thr Asn Ala Ile Lys Gln Thr Phe Ser Ala
            515                 520                 525

Pro Gly Phe Lys Cys Gly Ser Asp Trp Thr Arg Val Val Phe Ser Pro
        530                 535                 540

Asp Gly Ser Tyr Val Ala Ala Gly Ser Ala Glu Gly Ser Leu Tyr Ile
545                 550                 555                 560

Trp Ser Val Leu Thr Gly Lys Val Glu Lys Val Leu Ser Lys Gln His
                565                 570                 575

Ser Ser Ser Ile Asn Ala Val Ala Trp Ser Pro Ser Gly Ser His Val
            580                 585                 590

Val Ser Val Asp Lys Gly Cys Lys Ala Val Leu Trp Ala Gln Tyr
        595                 600                 605

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
gaagaggagc caggtgatga t                                           21

<210> SEQ ID NO 16
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 16
gaagaggagc caggugauga u                                           21

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
ggaatctcat tcgatgcata c                                           21

<210> SEQ ID NO 18
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 18
ggaaucucau ucgaugcaua c                                           21

<210> SEQ ID NO 19
<211> LENGTH: 24
<212> TYPE: DNA
<213> ORGANISM: Artificial Sequence
<220> FEATURE:
```

```
<223> OTHER INFORMATION: Synthetic oligonucleotide

<400> SEQUENCE: 19
tggctgctac ttctgcaatg atgt                                          24

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 20
gaatattcta attcaaccag atctaggt                                      28

<210> SEQ ID NO 21
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 21
ccggtgaacg tgcaaaacag cctcta                                        26

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 22
cttccagggc gcgagtggat agc                                           23
```

DISABLING AUTOPHAGY AS A TREATMENT FOR LYSOSOMAL STORAGE DISEASES

CROSS REFERENCE TO RELATED APPLICATIONS

This is the U.S. National Stage of International Application No. PCT/US2010/047730, filed Sep. 2, 2010, which was published in English under PCT Article 21(2), which in turn claims the benefit of U.S. Provisional Application No. 61/275,984, filed Sep. 4, 2009. The provisional application is, incorporated by reference in its entirety.

FIELD

This disclosure relates to methods of treating a subject with a lysosomal storage disorder, based on inhibition of autophagy in the subject. Further, methods of enhancing enzyme replacement therapy (ERT) for a subject with a lysosomal storage disorder are described, based on inhibition of autophagy in the subject.

BACKGROUND

Lysosomal storage disorders are a type of disease involving partial or complete deficiency of a lysosomal hydrolase. This deficiency results in incomplete lysosomal digestion of substrates specific to the hydrolase. Over time, the accumulation of undigested substrate can lead to various abnormalities, including progressive and severe neuro- and muscular-degeneration (see e.g., Settembre et al., *Human Mol. Genet.* 17:119-129, 2008; Fukuda et al., *Curr. Neurol. Neurosci. Rep.* 7:71-77, 2007). Pompe disease (a.k.a. Glycogenosis type II (GSDII)) is a type of lysosomal storage disorder caused by partial or complete deficiency of lysosomal acid α-glucosidase (GAA). The disease has been separated into two broad categories: infantile onset and late-onset. Patients with the infantile form generally die within the first year of life, due to cardiorespiratory failure. The late-onset form presents any time after infancy with generally no cardiac involvement but progressive skeletal muscle myopathy, leading to eventual respiratory failure. For a review, see Fukuda et al., *Curr. Neurol. Neurosci. Rep.* 7:71-77, 2007.

Enzyme replacement therapy (ERT) is used to treat several lysosomal storage disorders. In Pompe disease, ERT involves intravenous injections of a recombinant human GAA (rhGAA) precursor protein, which is internalized into cells where it rescues the GAA deficiency. ERT for Pompe disease is effective for glycogen clearance in cardiac muscle, but less effective for glycogen clearance from skeletal muscle (Raben et al., *Acta Myologica* 26:45-48, 2007). See also Fukuda et al., *Curr. Neurol. Neurosci. Rep.* 7:71-77, 2007.

Autophagy is a conserved mechanism of degradation whereby long-lived cytosolic proteins and damaged organelles (and other cytosolic content) are enveloped in double-membrane-bound vesicles called autophagosomes, which fuse with late endosomes to deliver their contents to the lysosome (Baehrecke, *Nat. Rev. Mol. Cell Biol.*, 6:505-510, 2005). Autophagy is involved in the cellular response to starvation, cellular differentiation, cell death, aging, cancer, and neurodegenerative disorders Inhibition of autophagy is suggested for the treatment of certain cancers (Apel et al., *Cancer Res.* 68:1485-1494, 2008; Seglen and Gordon, *Proc. Natl. Acad. Sci. U.S.A.* 79: 1889-1892, 1982; Carew et al., *Autophagy* 3:464-467, 2007). In several diseases, most strikingly in the neurodegenerative Huntington's Disease, up-regulation of autophagy to remove toxic aggregates appears to be a promising therapy (Winslow and Rubinsztein, *Biochim. Biophys. Acta.* 1782:723-729, 2008).

SUMMARY

Described herein is the unexpected discovery that inhibition of autophagy is an effective therapy and adjunctive therapy for Pompe disease and other lysosomal storage diseases.

Thus, there is provided herein a method of treating a lysosomal storage disorder in a subject, which method involves selecting or identifying a subject with a lysosomal storage disorder; and administering to the subject a therapeutically effective amount of an agent that inhibits autophagy, thereby treating the lysosomal storage disorder in the subject. In some examples, the lysosomal storage disorder is Pompe disease. In various embodiments, the agent that inhibits autophagy is an oligonucleotide comprising at least 15 bases and that hybridizes under high stringency conditions to an mRNA encoding an essential autophagy gene; a morpholino oligonucleotide comprising at least 15 bases and that hybridizes under high stringency conditions to an mRNA encoding an essential autophagy gene; a short hairpin RNA (shRNA) comprising at least 15 bases and that hybridizes under high stringency conditions to an mRNA encoding an essential autophagy gene (e.g., Atg5 or Atg7); an agent that decreases expression of an essential autophagy gene; an agent that inhibits an activity of an essential autophagy gene; an agent that inhibits activity of class III PI3 kinase; or a mixture or combination of two or more thereof. Optionally, the agent which inhibits autophagy is administered intramuscularly.

For instance, in one particular embodiment of the provided treatment method, the lysosomal storage disorder is Pompe disease and the autophagy inhibitor inhibits autophagy in skeletal muscle.

In particular embodiments, the method of treatment of a lysosomal storage disorder by inhibiting autophagy is combined with conventional treatment for the disorder, such as ERT. Thus, there is also provided herein a method of enhancing ERT in a subject by inhibiting autophagy in that subject. When used in conjunction with ERT, autophagy inhibitors, methods of administration, and so forth are substantially similar to those in the absence of treatment with ERT.

Also provided is an Atg7/GAA double knockout mouse, which is useful for instance as a model in which autophagy is suppressed only later in life. By way of example, this mouse model would be a useful model in which to observe effects of autophagy suppression in established disease, for instance in order to test or examine therapeutic drug application.

Further provided is a Pompe mouse model in which an autophagosomal marker (LC3) is tagged with a fluorescent protein (GFP) to monitor autophagy. These mice (GFP-LC3-GAA−/− mice) can be used, for example, to monitor autophagy in vivo to facilitate the screening and development of pharmaceuticals that block autophagy.

It will be further understood that the methods of inhibiting autophagy provided herein are useful beyond the specific circumstances that are described in detail herein, and for instance are expected to be useful for any number of conditions wherein autophagy is upregulated or functioning in a disturbed manner.

BRIEF DESCRIPTION OF THE FIGURES

FIG. 1A. Top panel: Western blot analysis of protein lysates from fast (gastrocnemius)

and slow (soleus) muscle with LC3 antibody. The absence of LC3II (an autophagosomal membrane-bound form of LC3) in the gastrocnemius, but not in soleus muscle indicates that, as expected, autophagy was successfully suppressed in fast but not in slow muscle from MLCcre:Atg7F/F:GAA−/− mice. Five month-old mice were used for the experiment. Data shown are representative of at least three experiments. Bottom panel: GAPDH was used as a loading control. FIGS. 1B and 1C. Immunostaining of single fast fibers (psoas) with lysosomal-associated membrane protein 1 (LAMP-1; a lysosomal marker) shows variability in the lysosomal size (B) and disposition (C) of the lysosomes.

FIG. 2A. Single muscle fibers isolated from fast (psoas) muscle of WT and MLCcre:Atg7F/F:GAA−/− mice were immunostained with the LAMP-1 antibody (lysosomal marker) and the FK2 antibody (a marker for mono- and poly-ubiquitinated proteins). No accumulation of the Ub proteins is observed in the WT myofibers, whereas in MLCcre:Atg7F/F:GAA−/− muscle Ub-positive inclusions are clearly present in the vicinity of the expanded lysosomes. Bar=20 µm. FIG. 2B. Western blot analysis of protein lysates with FK2 antibody showing a progressive increase in the amount of Ub-proteins. Fast (gastrocnemius) muscles were derived from 4-, 5- or 9-month-old MLCcre:Atg7F/F:GAA−/− mice.

FIGS. 3A and 3B: Autophagy is suppressed in adult, but not in young MLCcre:Atg7F/F mice on either GAA−/− or GAA+/+ background. FIG. 3A. Western blot analysis of protein lysates from fast (gastrocnemius) muscle from 1 month-old WT, GAA−/−, and MLCcre:Atg7F/F:GAA−/− mice with LC3 antibody. The presence of LC3II indicates that at this age autophagy is not suppressed in MLCcre:Atg7F/F:GAA−/− mice. FIG. 3B. Western blot analysis of protein lysates from fast (gastrocnemius) muscle from 1 month-old (lanes 1 and 2) and 4.5 month-old MLCcre:Atg7F/F:GAA+/+ mice (lanes 3 and 4) with LC3 antibody. Young mice are autophagy-competent, whereas, adult animals are autophagy-deficient.

FIG. 4: Suppression of autophagy in MLCcre:Atg7F/F:GAA−/− permits fully effective enzyme replacement therapy. Periodic acid-Schiff (PAS)-stained sections of fast (gastrocnemius) muscle from 4 month-old untreated and ERT-treated GAA−/− and MLCcre:Atg7F/F:GAA−/− showing a near complete glycogen clearance in MLCcre:Atg7F/F:GAA−/−, but not in GAA−/− mice. PAS-positive material (small dots) represents glycogen.

SEQUENCE LISTING

Figure 1A:
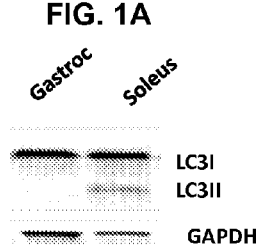
FIGS. 1A-1C: Characteristics of skeletal muscle from MLCcre:Atg7F/F:GAA−/− mice.

The nucleic acid and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

The Sequence Listing is submitted as an ASCII text file named "Sequence.txt" (~100 kb), created on Feb. 11, 2012, which is incorporated by reference herein.

In the accompanying sequence listing:

SEQ ID NOs: 1 and 2 are the nucleotide sequence and amino acid sequence, respectively, of murine acid α-glucosidase (GAA), deposited under GenBank Accession No. NM_001159324.

SEQ ID NOs: 3 and 4 are the nucleotide sequence and amino acid sequence, respectively, of murine Atg5, deposited under GenBank Accession No. NM_053069.

SEQ ID NOs: 5 and 6 are the nucleotide (cDNA) sequence and amino acid sequence, respectively, of human Beclin1 (Atg6), deposited under GenBank Accession No. NM_003766.

SEQ ID NOs: 7 and 8 are the nucleotide sequence and amino acid sequence, respectively, of murine Atg7, deposited under GenBank Accession No. NM_028835.

SEQ ID NOs: 9 and 10 are the nucleotide (cDNA) sequence and amino acid sequence, respectively, of human Atg9, deposited under GenBank Accession No. NM_173681.

SEQ ID NOs: 11 and 12 are the nucleotide (cDNA) sequence and amino acid sequence, respectively, of human Atg12, deposited under GenBank Accession No. NM_004707.

SEQ ID NOs: 13 and 14 are the nucleotide (cDNA) sequence and amino acid sequence, respectively, of human Atg16, deposited under GenBank Accession No. NM_030803.

SEQ ID NO: 15 is a nucleotide sequence encoding a shRNA specific for Atg5 mRNA.

SEQ ID NO: 16 is nucleotide sequence of a shRNA oligonucleotide specific for Atg5 mRNA.

SEQ ID NO: 17 is a nucleotide sequence encoding a control shRNA.

SEQ ID NO: 18 is the nucleotide sequence of a control shRNA.

SEQ ID NO: 19 is the nucleotide sequence of an Atg7 oligonucleotide.

SEQ ID NO: 20 is the nucleotide sequence of an Atg7 oligonucleotide.

SEQ ID NO: 21 is the nucleotide sequence of a Cre oligonucleotide.

SEQ ID NO: 22 is the nucleotide sequence of a Cre oligonucleotide.

DETAILED DESCRIPTION

I. Abbreviations

3-MA 3-Methyladenine
Atg autophagy-related gene
cDNA complementary DNA
CI-MPR cation-independent mannose-6-phosphate receptor
DKO double knockout
DNA deoxyribonucleic acid
dsDNA double-stranded DNA
dsRNA double-stranded RNA
ERT enzyme replacement therapy
GAA acid α-glucosidase
Gb3 globotriaosylceramide
GAG glycosaminoglycan
GFP green florescent protein
GSDII glycogenosis type II
LAMP-1 lysosomal-associated membrane protein 1
M6P mannose-6-phosphate
miRNA microRNA
MPS mucopolysaccharidoses
mRNA messenger RNA
PAS periodic acid-Schiff
PCR polymerase chain reaction
PI3K phosphoinositide 3-kinase
rhGAA recombinant human acid α-glucosidase
RNA ribonucleic acid
RNAi RNA interference
RT-PCR reverse transcriptase polymerase chain reaction
shRNA short hairpin RNA
siRNA small interfering RNA
ssDNA single-stranded DNA
TA tibialis anterior
TLR toll-like receptor
Ub ubiquitinated
UTR untranslated region II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

3-Methyladenine (3-MA; 6-Amino-3-methylpurine): 3-MA has the linear formula $C_6H_7N_5$. This molecule is available commercially (Sigma Catalog Number M9281). 3-MA inhibits the activity of class III PI3 kinases Inhibiting the activity of class III PI3 kinases inhibits autophagy; 3-MA is widely used to inhibit autophagy in tissue culture (see Seglen and Gordon, *Proc. Natl. Acad. Sci. U.S.A.*, 79:1889-1892, 1982 and Hamacher-Brady et al., *J. Biol. Chem.*, 281: 29776-29787, 2006).

Administration: Administration of an active compound ("agent") or composition can be by any route known to one of skill in the art. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body via the circulatory system.

Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Agent: Any substance or any combination of substances that is useful for achieving an end or result; for example, a substance or combination of substances useful for modulating gene expression or protein activity, or inhibiting autophagy. In some embodiments, the agent is a therapeutic agent, such as a therapeutic agent for the treatment of a lysosomal storage disease or disorder.

Altered expression: Expression of a biological molecule (for example, mRNA or protein) in a subject or biological sample from a subject that deviates from expression of the same biological molecule in a subject or biological sample from a subject having normal or unaltered characteristics for the biological condition being examined, for instance a biological condition associated with the expressed molecule. Normal expression can be found in a control, a standard for a population, etc.

Altered expression of a biological molecule may be associated with a disease or condition. Used in this context, the term "associated with" includes an increased risk of developing the disease, the disease itself, severity or extent of disease, and so forth. The directed alteration in expression of mRNA or protein may be associated with therapeutic benefits, for instance with regard to a disease or condition with which the biological molecule is associated.

Expression may be altered in such a manner as to be increased or decreased, depending on the embodiment or specific use. A decrease in expression of a biological molecule in a subject or in a biological sample from a subject means that there is less of the biological molecule in the subject or in the sample from the subject compared to a control. An increase in expression of a biological molecule in a subject or in a biological sample from a subject means that there is more of the biological molecule in the subject or in the sample from the subject compared to a control.

Altered protein expression refers to expression of a protein that is in some manner different from expression of the protein in a normal (wild type or unaltered) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that a protein domain or sub-domain is removed or added; (4) expression of an increased amount of the protein, compared to a control or standard amount; (5) expression of an decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); and (8) alteration of the localized (for example, organ or tissue specific) expression of the protein (such that the protein is not expressed where it would normally be expressed or is expressed where it normally would not be expressed), each compared to a control or standard.

Controls or standards appropriate for comparison to a sample, for the determination of altered expression, include samples believed to express normally as well as laboratory values, even though possibly arbitrarily set, keeping in mind that such values may vary from laboratory to laboratory. Laboratory standards and values may be set based on a known or determined population value and may be supplied in the format of a graph or table that permits easy comparison of measured, experimentally determined values. Appropriate controls are well known to or can readily be developed by those of ordinary skill in the art, though specific examples are provided herein for specific embodiments.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in *Remington* (*The Science and Practice of Pharmacology,* 19*th Edition* (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound. It will be recognized that these terms may overlap in some circumstances.

Antisense and Sense: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense compound/molecule: Oligomeric compounds that are at least partially complementary to the region of a target nucleic acid molecule to which it hybridizes. Thus, antisense molecules are molecules that are specifically hybridizable or specifically complementary to either RNA or plus strand DNA (while sense molecules are molecules that are specifically hybridizable or specifically complementary to the minus strand of DNA). As used herein, an antisense compound that is "specific for" a target nucleic acid molecule is one which specifically hybridizes with and modulates expression of the target nucleic acid molecule. As used herein, a "target" nucleic acid is a nucleic acid molecule the expression of which an antisense compound is designed to modulate (e.g., inhibit or reduce) through specific hybridization.

In some embodiments, the antisense compounds is 15-30 bases in length, such as 15, 16, 17, 18, 19, 20, 21, 22, 23, 24, 25, 26, 27, 28, 29 or 30 bases in length. In other embodiments, the antisense compound is 15-50 nucleotides in length. In some embodiments, the antisense compound is at least 80%, at least 85%, at least 90%, at least 95%, at least 99% or 100% complementary to a target mRNA (such as an mRNA of an essential autophagy gene).

Non-limiting examples of antisense compounds include primers, probes, antisense oligonucleotides, small interfering RNAs (siRNAs), microRNAs (miRNAs), shRNAs and ribozymes. Antisense compounds can be introduced (e.g., to a subject or a system) as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound (e.g., hairpins).

An "antisense oligonucleotide" is a single-stranded antisense compound that is a nucleic acid-based oligomer. An antisense oligonucleotide can include one or more chemical modifications to the sugar, base, and/or inter-nucleoside linkages. Generally, antisense oligonucleotides are "DNA-like" such that when the antisense oligonucleotide hybridizes to a target mRNA, the duplex is recognized by RNase H (an enzyme that recognizes DNA:RNA duplexes), resulting in cleavage of the mRNA.

Autophagy: Autophagy is a conserved cellular mechanism of degradation whereby long-lived cytosolic proteins and damaged organelles (and other things contained in the cytosol) are enveloped in double-membrane-bound vesicles called autophagosomes, which fuse with late endosomes to deliver their contents to the lysosome. Autophagy is involved in the cellular response to starvation, cellular differentiation, cell death, aging, cancer and neurodegenerative disorders.

Autophagosomes form from the elongation of small membrane structures known as autophagosome precursors. The formation of autophagosomes is initiated by class III phosphoinositide 3-kinase and autophagy-related gene (Atg) 6 (also known as Beclin-1). In addition, two further systems are involved, composed of the ubiquitin-like protein Atg8 (known as LC3 in mammalian cells) and the Atg4 protease on the one hand and the Atg12-Atg5-Atg16 complex on the other. Atg7 is also required. The outer membrane of the autophagosome fuses in the cytoplasm with a lysosome to form an autolysosome or autophagolysosome, where their contents are degraded via acidic lysosomal hydrolases.

An autophagy inhibitor is a compound/agent that inhibits autophagy. A compound that inhibits the protein activity of a protein encoded by an essential autophagy gene presumptively will be an autophagy inhibitor. A compound that decreases expression of a protein encoded by an essential autophagy gene presumptively will be an autophagy inhibitor. A compound that disrupts the autophagy pathway presumptively will be an autophagy inhibitor. Non-limiting examples of autophagy inhibitors include 3-Methyladenine (3-MA) and siRNA that results in a decrease in expression of the essential autophagy genes Atg5 or Atg7.

cDNA (complementary DNA): A piece of DNA lacking internal, non-coding segments (introns) and transcriptional regulatory sequences. cDNA may also contain untranslated regions (UTRs) that are involved in translational control in the corresponding RNA molecule. cDNA is usually synthesized in the laboratory by reverse transcription from messenger RNA extracted from cells.

Deletion: The removal of a sequence of DNA (which may be as short as a single nucleotide), the regions on either side being joined together.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached.

Unless otherwise specified, any reference to a DNA molecule is intended to include the reverse complement of that DNA molecule. Except where single-strandedness is required by context, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Effective amount of an agent/compound: A quantity of agent/compound sufficient to achieve a desired effect in a subject (or system) being treated with the agent/compound. An effective amount of a compound can be administered in a single dose, or in several doses, for example daily or at other intervals, during a course of treatment. However, the effective amount of the compound will be influenced by the compound applied, the subject being treated, the severity and type of the affliction, the manner of administration of the compound, and other factors that will be recognized by one of ordinary skill in the relevant field.

Enzyme replacement therapy (ERT): A therapeutic system used to treat several lysosomal storage disorders, in which an enzyme that is missing or defective (usually through genetic disease) is replaced therapeutically. The replacing enzyme is usually provided through intravenous infusion. See, for instance, Schlander and Beck, *Curr. Med. Res. Opin.*, 25:1285-93, 2009; Morel and Clarke, *Expert Opin. Biol. Ther.*, 9:631-9. 2009; Rohrbach and Clarke, *Drugs*, 67:2697-716, 2007; Schoser et al., *Neurotherapeutics*, 5:569-78, 2008; Breunig and Wanner, *J. Nephrol.*, 21:32-37, 2008; and Lidove et al., *Int. J. Clin. Pract.*, 61:293-302, 2007.

ERT for Pompe disease involves intravenous injections of a recombinant human GAA (rhGAA) precursor containing mannose-6-phosphate (M6P) groups. The M6P groups bind to cation-independent mannose-6-phosphate receptor (CI-MPR) on the cell surface. The CI-MPR/rhGAA complex internalizes from the cell surface in transport vesicles that fuse with endosomes. In the acidic pH of late endosomes, the rhGAA dissociates from CI-MPR and is transported to the lysosomes, where it rescues the GAA deficiency (see Fukuda et al., *Curr. Neurol. Neurosci. Rep.*, Vol. 7:71-77, 2007). ERT for Pompe disease is effective for glycogen clearance in cardiac muscle, but less effective for glycogen clearance from skeletal muscle (Raben et al., *Acta Myologica*, 26: 45-48, 2007). Similarly, in genetically engineered mice that lack expression of GAA (a mouse model of Pompe disease), ERT is effective in clearing glycogen from type I muscle fibers, but not type II muscle fibers, which predominate in skeletal muscle (Raben et al., *Molecular Therapy*, 11: 48-56, 2005).

Essential autophagy gene: a gene that encodes a protein that is required for autophagy. Example essential autophagy genes include, but are not necessarily limited to, Atg5, Atg6 (Beclin 1), Atg7, Atg9, Atg12, Atg16 and any gene encoding a class III PI3K or modulator of a class III PI3K.

Fluorescent protein: A protein that either directly (through its primary, secondary, or tertiary structure) or indirectly (through a co-factor, non-protein chromophore, or a substrate, or due to the addition of a fluor) produces or emits fluorescent light. Non-limiting examples of fluorescent proteins are the green fluorescent protein (GFP; see, for instance, GenBank Accession Number M62654) from the Pacific Northwest jellyfish, *Aequorea victoria* and natural and engineered variants thereof (see, for instance, U.S. Pat. Nos. 5,804,387; 6,090,919; 6,096,865; 6,054,321; 5,625,048; 5,874,304; 5,777,079; 5,968,750; 6,020,192; and 6,146,826; and published international patent application WO 99/64592).

Fluorophore: A chemical compound, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ.

Examples of fluorophores that may be used are provided in U.S. Pat. No. 5,866,366 to Nazarenko et al., and include for instance: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other contemplated fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a subject to an agent that inhibits gene expression. Expression of a gene also may be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression may be measured at the RNA level or the protein level and by any method known in the art, including Northern blot, reverse transcriptase polymerase chain reaction (RT-PCR), Western blot, or in vitro, in situ, or in vivo protein activity assay(s).

The expression of a nucleic acid may be modulated compared to a control state, such as at a control time (for example, prior to administration of a substance or agent that affects regulation of the nucleic acid under observation) or in a control cell or subject, or as compared to another nucleic acid. Such modulation includes but is not necessarily limited to overexpression, underexpression, or suppression of expression. In addition, it is understood that modulation of nucleic acid expression may be associated with, and in fact may result in, a modulation in the expression of an encoded protein or even a protein that is not encoded by that nucleic acid.

Interfering with or inhibiting gene expression refers to the ability of an agent to measurably reduce the expression of a target gene. Expression of a target gene may be measured by any method known to those of skill in the art, including for example measuring mRNA or protein levels. It is understood that interfering with or inhibiting gene expression is relative, and does not require absolute suppression of the gene. Thus, in certain embodiments, interfering with or inhibiting gene expression of a target gene requires that, following application of an agent, the gene is expressed at least 5% less than prior to application, at least 10% less, at least 15% less, at least 20% less, at least 25% less, or even more reduced. Thus, in some particular embodiments, application of an agent reduces expression of the target gene by about 30%, about 40%, about 50%, about 60%, or more. In specific examples, where the agent is particularly effective, expression is reduced by 70%, 80%, 85%, 90%, 95%, or even more. Gene expression is substantially eliminated when expression of the gene is reduced by 90%, 95%, 98%, 99% or even 100%.

Heterologous: A type of sequence that is not normally (for example, in the wild-type sequence or organism) found adjacent to a second sequence. In one embodiment, the sequence is from a different genetic source, such as a virus or other organism, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between two distinct nucleic acid sequences or two distinct regions of the same nucleic acid sequence.

In vitro amplification: Techniques that increase the number of copies of a nucleic acid molecule in a sample or specimen. An example of in vitro amplification is the polymerase chain reaction (PCR), in which a pair of oligonucleotide primers is added to a sample under conditions that allow for the hybridization of the primers to a nucleic acid template in the sample. The primers are extended under suitable conditions, dissociated from the template, and then re-annealed, extended, and dissociated to amplify the number of copies of the nucleic acid. In vitro amplification includes, but is not limited to, RT-PCR, quantitative real time PCR, DNA replication, RNA transcription, and primer extension. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Inhibiting/Inhibit/Inhibition: To decrease, reduce, limit, or block something such as some activity, action or function, directly or indirectly. The term is not intended to be absolute—in that inhibition can occur where some of the activity, action or function still occurs. Instead, the term is intended to convey a range of degrees of the reduction of activity, action, or function, such as at least 10%, at least 20%, at least 30%, at least 50%, at least 80%, at least 90%, at least 95%, or even 100% as compared to control measurements of the same activity, action or function without the inhibitory factor.

Inhibiting protein activity: To decrease, limit, or block an action, function or expression of a protein. The phrase inhibit protein activity is not intended to be an absolute term—in that it does not preclude that some activity may remain. Instead, the phrase is intended to convey a wide-range of inhibitory effects that various agents may have on the normal (for example, uninhibited or control) protein activity. Thus, protein activity may be inhibited when the level or activity of any direct or indirect indicator of the protein's activity is changed (e.g., decreased) by at least 10%, at least 20%, at least 30%, at least 50%, at least 80%, at least 90%, at least 95%, or even 100% as compared to control measurements of the same indicator.

Inhibition of protein activity may also be effected, for example, by inhibiting expression of the gene encoding the protein or by decreasing the half-life of the mRNA encoding the protein, or the half-life of the protein itself. In various embodiments, each of these will result in a reduction of apparent protein activity in the subject, cell, or system.

Injectable composition: A pharmaceutically acceptable fluid composition comprising at least one active ingredient (e.g., compound/agent), for example, a protein, peptide, antibody, oligonucleotide, morpholino, or small molecule inhibitor of autophagy. The active ingredient is usually dissolved or suspended in a physiologically acceptable carrier, and the composition can additionally comprise usually minor amounts of one or more non-toxic auxiliary substances, such as emulsifying agents, preservatives, pH buffering agents and the like. Injectable compositions that are useful for use with the compositions of this disclosure are conventional; appropriate formulations are well known in the art.

Gene knockout: Also referred to as "knock-out" or "knockout," this is a genetic modification resulting from the disruption of the genetic information (e.g., encoding sequence) at a chromosomal locus. "Knockin," "knock-in" or "gene knockin" as used herein indicates a genetic modification that includes replacement of genetic information encoded at a chromosomal locus with a different DNA sequence or insertion of foreign genetic information at a chromosomal locus (e.g., the substitution in the genome of a wild type encoding sequence for an engineered modified version, or the insertion of a wild type encoding sequence in place of a mutant or variant sequence in the genome).

A knockout animal is an animal in which all (or a significant proportion) of the animal's cells harbor a gene knockout. A knockin animal is an animal in which a significant proportion of the animal's cells harbor a genetic knockin. Thus, for instance a knockout mouse is a mouse in which all (or a significant proportion) of the mouse's cells harbor a gene knockout. Knocking out two genes simultaneously in an organism is known as a double knockout (DKO). Methods and techniques for generating knockout, knockin, double knockout and conditional knockout animals are known to those of skill in the art. See, for instance, Nagy et al., Manipulating the Mouse Embryo: A Laboratory Manual, Cold Spring Harbor Laboratory Press; 3rd edition, 2002; and Tymms and Kola (eds), Gene Knockout Protocols, Humana Press; 1st edition, 2001.

A conditional knockout allows gene deletion in a spatial (e.g., cell, organ, or tissue) or time specific manner. This is done, for example, by introducing short sequences called loxP sites around the gene. These sequences will be introduced into the germ-line via the same mechanism as a knockin. This germ-line can then be crossed to another germline containing Cre-recombinase which is a bacterial enzyme that can recognize these sequences, recombines them and deletes the gene flanked by these sites. Methods and techniques for making knockout, knockin, double knockout and conditional knockout animals are well known to those of skill in the art.

Label: A composition detectable by (for instance) spectroscopic, photochemical, biochemical, immunochemical, or chemical means. Typical labels include fluorescent proteins or protein tags, fluorophores, radioactive isotopes (including for instance $^{32}$P), ligands, biotin, digoxigenin, chemiluminescent agents, electron-dense reagents (such as metal sols and colloids), and enzymes (e.g., for use in an ELISA), haptens, and proteins or peptides (such as epitope tags) for which antisera or monoclonal antibodies are available. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, John Wiley & Sons, New York (1998). A label often provides or generates a measurable signal, such as radioactivity, fluorescent light or enzyme activity, which can be used to detect and/or quantitate the amount of labeled molecule.

Lysosomal storage disease/disorder: Lysosomal storage diseases/disorders are a type of disease involving partial or complete deficiency of a lysosomal hydrolase. This deficiency results in incomplete lysosomal digestion of substrates specific to the hydrolase. Over time, the accumulation of undigested substrate can lead to various abnormalities, including progressive and severe neuro- and muscular-degeneration. (See Settembre et al., *Human Mol. Genet.*, 17:119-129, 2008; Fukuda et al., *Curr. Neurol. Neurosci. Rep.*, 7:71-77, 2007.) The phrase lysosomal storage disorder is synonymous with lysosomal storage disease.

Lysosomal storage disorders include but are not limited to GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease, Neuronal Ceroid Lipofuscinoses (CLN6 disease, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pycnodysostosis, Sandhoff disease, Schindler disease, Salla disease/ Sialic Acid Storage Disease, Tay-Sachs/GM2 gangliosidosis, and Wolman disease.

Mammal: This term includes both human and non-human mammals. Similarly, the term subject includes both human and veterinary subjects, for example, humans, non-human primates, mice, rats, dogs, cats, horses, and cows.

MicroRNA (miRNA): Single-stranded RNA molecules that regulate gene expression. miRNAs are generally 21-23 nucleotides in length, and are processed from primary transcripts known as pre-miRNA to short stem-loop structures called pre-miRNA and finally to functional miRNA. Mature miRNA molecules are partially complementary to one or more messenger RNA molecules, and their primary function is to down-regulate gene expression. MicroRNAs regulate gene expression through the RNA interference (RNAi) pathway.

Modulator: An agent that increases or decreases (modulates) the activity of a protein or other bio-active compound, as measured by the change in an experimental biological parameter. A modulator can be any compound or mixture of compounds, such as organic or inorganic (small) molecule(s), polypeptide(s), hormone(s), nucleic acid molecule(s), sugar(s), lipid(s) and so forth.

Morpholino: A morpholino (morpholino oligonucleotide) is structurally different from natural nucleic acid oligonucleotides, with morpholino rings replacing the ribose or deoxyribose sugar moieties and non-ionic phosphorodiamidate linkages replacing the anionic phosphates of DNA and RNA. Each morpholino ring suitably positions one of the standard bases (A, G, C, T/U), so that, for example, a 25-base morpholino oligonucleotide strongly and specifically binds to its complementary 25-base target site in a strand of RNA via Watson-Crick pairing. Because the backbone of the morpholino oligonucleotide is not recognized by cellular enzymes of signaling proteins, it is stable to nucleases and does not trigger an innate immune response through the toll-like receptors (TLRs). This avoids loss of the morpholino oligonucleotide, inflammation or interferon induction. Morpholinos can be delivered by a number of techniques, including direct injection to tissues or via infusion pump and intravenous bolus, topical application, or intraperitoneal injection. The terms "oligonucleotide" and "oligo" encompass morpholino oligonucleotides (in spite of the structural differences recognized above). In some embodiments, the morpholino oligonucleotide is 15-30 bases in length, such as 15, 16, 17, 18, 19, 20, 21, 22, 23, 24, 25, 26, 27, 28, 29 or 30 bases in length.

Mutation: Any change of DNA sequence, for instance within a gene or a chromosome. In some instances, a mutation will alter a characteristic or trait (phenotype), but this is not always the case. Types of mutations include base substitution point mutations (for example, transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of lysosomal storage disorders. This term also encompasses DNA alterations that are present constitutionally, that alter the function of the encoded protein in a readily demonstrable manner, and that can be inherited by the children of an affected individual. In this respect, the term overlaps with polymorphism, but generally refers to the subset of constitutional alterations that have arisen within the past few generations in kindred and that are not widely disseminated in a population group. In particular embodiments, the term is directed to those constitutional alterations that have major impact on the health of affected individuals.

Nucleic acid molecule: A polymeric form of nucleotides, which may include both sense and anti-sense strands of RNA, cDNA, genomic DNA, and synthetic forms and mixed polymers thereof. A nucleotide refers to a ribonucleotide, deoxynucleotide or a modified form of either type of nucleotide. The phrase nucleic acid molecule as used herein is synonymous with nucleic acid and polynucleotide. A nucleic acid molecule is usually at least six bases in length, unless otherwise specified. The term includes single- and double-stranded forms. The term includes both linear and circular (plasmid) forms. A polynucleotide may include either or both naturally occurring and modified nucleotides linked together by naturally occurring nucleotide linkages and/or non-naturally occurring chemical bonds and/or linkers.

Nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term nucleic acid molecule also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless specified otherwise, the left hand end of a polynucleotide sequence written in the sense orientation is the 5'-end and the right hand end of the sequence is the 3'-end. In addition, the left hand direction of a polynucleotide sequence written in the sense orientation is referred to as the 5'-direction, while the right hand direction of the polynucleotide sequence is referred to as the 3'-direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

Oligonucleotide: A plurality of joined nucleotides joined by native phosphodiester bonds, between about six and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules and morpholinos.

Particular oligonucleotides and oligonucleotide analogs include linear sequences up to about 200 nucleotides in length, for example a sequence (such as DNA or RNA or morpholino) that is at least six bases, for example at least 8, 10, 15, 20, 25, 30, 35, 40, 45, 50, 100 or even 200 bases long, or from about six to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: Pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell.

Phosphoinositide 3-kinase (PI3 kinase; PI3K): A family of related intracellular enzymes capable of phosphorylating the 3 position hydroxyl group of the inositol ring of phosphatidylinositol (PtdIns or PI). They are also known as phosphatidylinositol-3-kinases. The phosphoinositol-3-kinase family of proteins is divided into three different classes: Class I, Class II and Class III, based on primary structure, regulation, and in vitro lipid substrate specificity. Class I PI3Ks are responsible for the production of phosphatidylinositol 3-phosphate (PI(3)P), phosphatidylinositol (3,4)-bisphosphate (PI(3,4)$P_2$) and phosphatidylinositol (3,4,5)-trisphosphate (PI(3,4,5)$P_3$).

Class II PI3Ks catalyze the production of PI(3)P and PI(3, 4)$P_2$ from PI. Class III PI3K produces only PI(3)P from PI, and exists as a heterodimer of catalytic (Vps34) and regulatory (p150) subunits. Class III PI3K is primarily involved in the trafficking of proteins and vesicles, including formation of the autophagosome. PI3Ks exert opposing actions on the autophagy pathway, with class I PI3K inhibiting and class III PI3K stimulating autophagy. Class III PI3K production of PI(3)P from PI stimulates autophagy (Petiot et al., *J. Biol. Chem.*, 275:992-998, 2000). The class III PI3K inhibitor 3-methyladenine (3-MA) is used as an inhibitor of autophagy. 3-MA inhibits autophagosome formation and the sequestration of molecules into autophagosomes (Hamacher-Brady et al., *J. Biol. Chem.*, 281: 29776-29787, 2006).

Pompe disease: Pompe disease (a.k.a. Glycogenosis type II (GSDII)) is a type of lysosomal storage disorder caused by partial or complete deficiency of lysosomal acid α-glucosidase (GAA). GAA is responsible for the breakdown of glycogen within lysosomes, and enzyme deficiency results in accumulation of glycogen, primarily in skeletal and cardiac muscle. The disease has been separated into two broad categories: infantile onset and late-onset. Patients with the infantile form generally die within the first year of life due to cardiorespiratory failure. The late-onset form presents any time after infancy with generally no cardiac involvement but progressive skeletal muscle myopathy, leading to eventual respiratory failure. It is estimated that 1 in 40,000 individuals have some form of Pompe disease (for a review, see Fukuda et al., *Curr. Neurol. Neurosci. Rep.*, 7:71-77, 2007).

The cells of humans with Pompe disease exhibit autophagic debris, fragmented mitochondria, remnants of lysosomal membranes and a large number of autophagosomes in the core of muscle fibers. In GAA knockout mice, Type II muscle fibers exhibit extensive autophagic buildup and a large number of autophagosomes, which ERT does not alleviate. It has been proposed that over time this accumulation of autophagic debris and autophagosomes leads to a deficiency of muscle function (Fukuda et al., *Ann. Neurol.*, 59:700-708, 2006). Additionally, the increased formation of autophagosomes in Pompe disease disrupts trafficking of CI-MPR. In fibroblasts isolated from patients with Pompe disease, trafficking of CI-MPR through endosomes is impaired, as indicated by disrupted CI-MPR localization and function (Cardone et al., *Pathogenetics*, 1 (22 pages), 2008; doi:10.1186/1755-8417-1-6). Based on this finding, it was suggested that CI-MPR is sequestered in autophagosomes in the cells of Pompe disease patients, which depletes the amount of functionally available CI-MPR at the plasma membrane.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease, or a lessening of its duration.

Recombinant: A nucleic acid (or protein) that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

Ribozyme: RNA molecules with enzyme-like properties, which can be designed to cleave specific RNA sequences. Ribozymes are also known as RNA enzymes or catalytic RNAs.

RNA interference (RNAi; RNA silencing): A cellular gene-silencing mechanism whereby specific double-stranded RNA (dsRNA) molecule(s) trigger the degradation of homologous mRNA (also called target RNA). Double-stranded RNA is processed into small interfering RNAs (siRNA), which serve as a guide for cleavage of the homologous mRNA in the RNA-induced silencing complex (RISC). The remnants of the target RNA may then also act as siRNA; thus resulting in a cascade effect.

Sequence identity: The primary sequence similarity between two nucleic acid molecules, or two amino acid molecules, is expressed in terms of the similarity between the sequences, otherwise referred to as sequence identity. Sequence identity is frequently measured in terms of percentage identity (or similarity or homology); the higher the percentage, the more similar are the two sequences.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS USA* 85: 2444, 1988); Higgins and Sharp (*Gene*, 73: 237-244, 1988); Higgins and Sharp (*CABIOS* 5: 151-153, 1989); Corpet et al. (*Nuc. Acids Res.* 16: 10881-10890, 1988); Huang et al. (*Comp. Appls Biosci.* 8: 155-165, 1992); and Pearson et al. (*Meth. Mol. Biol.* 24: 307-31, 1994). Altschul et al. (*Nature Genet.*, 6: 119-129, 1994) presents a detailed consideration of sequence alignment methods and homology calculations.

By way of example, the alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., *J. Mol. Biol.* 215:403-410, 1990; Gish. & States, *Nature Genet.* 3:266-272, 1993; Madden et al. *Meth.*  *Enzymol.* 266:131-141, 1996; Altschul et al., *Nucleic Acids Res.* 25:3389-3402, 1997; and Zhang & Madden, *Genome Res.* 7:649-656, 1997.

Proteins orthologs are typically characterized by possession of greater than 75% sequence identity counted over the full-length alignment with the amino acid sequence of a specific reference protein, using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of particular domains of the disclosed peptides.

When significantly less than the entire sequence is being compared for sequence identity, homologous sequences will typically possess at least 80% sequence identity over short windows of 10-20 amino acids, and may possess sequence identities of at least 85%, at least 90%, at least 95%, or at least 99%. Sequence identity over such short windows can be determined using LFASTA; methods are described at the NCSA Website; also, direct manual comparison of such sequences is a viable if somewhat tedious option.

One of skill in the art will appreciate that the sequence identity ranges provided herein are provided for guidance only; it is entirely possible that strongly significant homologs could be obtained that fall outside of the ranges provided.

The similarity/identity between two nucleic acid sequences can be determined essentially as described above for amino acid sequences. An alternative indication that two nucleic acid molecules are closely related is that the two molecules hybridize to each other (or both hybridize to the same third sequence) under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ of a hybrid molecule can be estimated from the following equation:

$$T_m = 81.5\ C - 16.6(\log_{10}[Na^+]) + 0.41(\%\ G+C) - 0.63 (\%\ \text{formamide}) - (600/l)$$

Where l=the length of the hybrid in base pairs.

This equation is valid for concentrations of $Na^+$ in the range of 0.01 m to 0.4 M, and it is less accurate for calculations of $T_m$ in solutions of higher $[Na^+]$. The equation is also primarily valid for DNAs whose G+C content is in the range of 30% to 75%, and it applies to hybrids greater than 100 nucleotides in length.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though wash times also influence stringency. Calculations regarding hybridization conditions required for attaining particular degrees of stringency are discussed by Sambrook et al. (ed.) (*Molecular Cloning: A Laboratory Manual*, 2nd ed., vol. 1-3, Cold Spring Harbor Laboratory Press, Cold Spring Harbor, N.Y., 1989, chapters 9 and 11), and Tijssen (*Laboratory Techniques in Biochemistry and Molecular Biology Part I, Ch. 2*, Elsevier, N.Y., 1993), herein incorporated by reference. The following are exemplary hybridization conditions:

Very High Stringency (detects sequences that share 90% identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (detects sequences that share 80% identity or greater)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (detects sequences that share greater than 50% identity)
  Hybridization: 6×SSC at RT to 55° C. for 16-20 hours
  Wash at least twice: 2×-3×SSC at RT to 55° C. for 20-30 minutes each.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specifically hybridizable and specifically complementary are terms that indicate a sufficient degree of complementarity such that stable and specific binding occurs between the oligonucleotide (or it's analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

In some embodiments, an oligonucleotide, morpholino oligonucleotide or shRNA (or other type of antisense compound) is at least 80%, at least 85%, at least 90%, at least 95%, at least 99% or 100% complementary to the target mRNA.

Short hairpin RNA (shRNA): A singled stranded sequence of RNA that makes a tight hairpin turn and can be used to silence gene expression via RNA interference (RNAi). The shRNA hairpin structure is cleaved by the cellular machinery into siRNA. Small hairpin RNA (shRNA) is synonymous with short hairpin RNA. DNA encoding a shRNA is can be included on a plasmid and operably linked to a promoter. This plasmid can be introduced into cells in which inhibition of expression a target sequence is desired. This plasmid is usually passed on to daughter cells, enabling inheritance of the gene silencing. Once produced or present in a cell, the hairpin structure of shRNA is cleaved by cellular machinery into siRNA.

Small interfering RNA (siRNA): Synthetic or naturally-produced small double stranded RNAs (dsRNAs) that can induce gene-specific inhibition of expression in invertebrate and vertebrate species through the RNAi pathway. siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. The double stranded RNAs can be formed from complementary single stranded RNAs (ssRNAs) or from a single stranded RNA that forms a hairpin or from expression from a DNA vector (e.g., shRNA). siRNAs are also referred to as "small inhibitory RNAs."

Small molecule inhibitor: A molecule, typically with a molecular weight less than 1000, or in some embodiments, less than about 500 Daltons, wherein the molecule is capable of inhibiting, to some measurable extent, an activity of some target molecule.

Subject: Living multi-cellular vertebrate organisms, a category that includes both human and non-human mammals. This term encompasses both known and unknown individuals, such that there is no requirement that a person working with a sample from a subject know who the subject is, or even from where the sample was acquired.

Subject susceptible to a disease or condition: A subject capable of, prone to, or predisposed to developing a disease or condition. It is understood that a subject already having or showing symptoms of a disease or condition is considered "susceptible" since they have already developed it.

Target sequence: A portion of single-stranded DNA (ssDNA), dsDNA, or RNA that, upon hybridization to a therapeutically effective oligonucleotide or oligonucleotide analog (e.g., a morpholino), results in the inhibition of expression of a gene, such as an essential autophagy. Either an antisense or a sense molecule can be used to target a portion of dsDNA, as both will interfere with the expression of that portion of the dsDNA. The antisense molecule can bind to the plus strand, and the sense molecule can bind to the minus strand. Thus, target sequences can be ssDNA, dsDNA, and RNA.

Therapeutically effective amount/dose: A quantity of compound/agent sufficient to achieve a desired effect in a subject being treated or a system to which the compound/agent is applied/administered.

An effective amount of a compound may be administered in a single dose, or in several doses, for example daily (or at other intervals), during a course of treatment. However, the effective amount will be influenced by the compound applied, the subject being treated, the severity and type of the affliction, the manner of administration of the compound, and other factors that will be recognized by one of ordinary skill in the art. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces the desired effect(s).

Under conditions sufficient for: A phrase used to describe any environment or set of conditions that permits the desired activity or outcome.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below.

All publications, patent applications, patents, and other references mentioned herein are incorporated by reference in their entirety. All GenBank Accession numbers are herein incorporated by reference as they appeared in the database on Sep. 4, 2009. In case of conflict, the present specification, including explanations of terms, will control. In addition, the materials, methods, and examples are illustrative only and not intended to be limiting.

III. Overview of Several Embodiments

Disclosed herein is a method of treating a subject with a lysosomal storage disorder, which method comprises selecting a subject with a lysosomal storage disorder and administering to the subject a therapeutically effective amount of an agent that inhibits autophagy. In certain embodiments, the method further comprises selecting a subject undergoing ERT treatment for a lysosomal storage disorder.

In some embodiments, autophagy is inhibited in a subject by treating a subject with a therapeutically effective amount of an agent that decreases expression of an essential autophagy gene in a subject. For instance, in some embodiments, a subject is treated with a therapeutically effective amount of a morpholino oligonucleotide that reduces expression of the protein encoded by the Atg5 gene. In other embodiments, autophagy is inhibited by treating a subject with a therapeutically effective amount of an agent that inhibits class III PI3 kinase activity.

The agent that inhibits autophagy will comprise, in various embodiments, an oligonucleotide comprising at least about 15 contiguous bases and that hybridizes to the mRNA of an essential autophagy gene under high stringency conditions; a morpholino oligonucleotide comprising at least about 15 contiguous bases and that hybridizes to the mRNA of an essential autophagy gene under high stringency conditions; an shRNA comprising at least about 15 contiguous bases and that hybridizes to the mRNA of an essential autophagy gene under high stringency conditions; an agent that binds to an essential autophagy gene; an agent that decreases the expression of a protein encoded by an essential autophagy gene; an agent that decreases the expression of Atg5, Atg6, Atg7, Atg9, Atg12 or Atg16 protein or a combination of two or more of Atg5, Atg6, Atg7, Atg9, Atg12 or Atg16 protein; an agent that enhances the proteolysis of a protein encoded by an essential autophagy gene; and agent that enhances the proteolysis of Atg5, Atg6, Atg7, Atg9, Atg12 or Atg16 or a combination of two or more of Atg5, Atg6, Atg7, Atg9, Atg12 or Atg16; an agent that inhibits the activity of a class III PI3 kinase; or a mixture of two or more thereof. For instance, in some examples the agent that inhibits autophagy comprises SEQ ID NO: 15 or SEQ ID NO: 16. Optionally, an agent as used in the provided method may be modified by addition of a detectable label.

In various embodiments, the agent is administered orally, subcutaneously, intramuscularly, intravenously, intraperitoneally, transdermally, intranasally, or rectally. In some embodiments the agent is administered intramuscularly to skeletal muscle.

In specific examples, the agent is an oligonucleotide comprising at least about 15 contiguous bases and that hybridizes to the mRNA of Atg5 under stringent or high stringency conditions. In some embodiments, the oligonucleotide is 15-30 nucleotides in length, such as 15, 16, 17, 18, 19, 20, 21, 22, 23, 24, 25, 26, 27, 28, 29 or 30 nucleotides in length. In some embodiments, the oligonucleotide is at least 80%, at least 85%, at least 90%, at least 95%, at least 99% or 100% complementary to the Atg5 mRNA. Such oligonucleotides will, in some embodiments, be a morpholino, for instance a morpholino that comprises the sequence shown in SEQ ID NO: 21. In some embodiments such oligonucleotides are shRNA molecules encoded by plasmid DNA.

In specific examples, the agent is an oligonucleotide comprising at least about 15 contiguous bases and that hybridizes to the mRNA of Atg7 under stringent or high stringency conditions. In some embodiments, the oligonucleotide is 15-30 nucleotides in length, such as 15, 16, 17, 18, 19, 20, 21, 22, 23, 24, 25, 26, 27, 28, 29 or 30 nucleotides in length. In some embodiments, the oligonucleotide is at least 80%, at least 85%, at least 90%, at least 95%, at least 99% or 100% complementary to the Atg7 mRNA. Such oligonucleotides will, in some embodiments, be a morpholino oligonucleotide. In some embodiments such oligonucleotides are shRNA molecules encoded by plasmid DNA.

Unexpectedly, autophagy was suppressed in adult but not in young ΔAtg7-GAA-DKO mice. Thus, there is provided herein a mouse model in which autophagy is suppressed later in life. This double (Atg7 and GAA) knockout model may closely mimic and can be used to study what might be achieved by pharmacological suppression of autophagy in the clinical setting.

Further provided herein is a Pompe mouse model in which an autophagosomal marker (LC3) is tagged with a fluorescent protein (GFP) to monitor autophagy. These mice (GFP-LC3-GAA−/− mice) can be used, for example, to monitor autophagy in vivo to facilitate the development of pharmaceuticals that block autophagy.

Also provided is the use of an agent that inhibits autophagy in the preparation of a medicament for the treatment of a lysosomal storage disorder. In some embodiments, the lysosomal storage disorder is Pompe disease. In some embodiments, the medicament is for intramuscular administration. In particular examples, the lysosomal storage disorder is Pompe disease and the autophagy inhibitor inhibits autophagy in skeletal muscle. In some embodiments, the agent comprises a detectable label.

In some embodiments, the agent that inhibits autophagy comprises: an oligonucleotide comprising at least 15 bases and that hybridizes under high stringency conditions to an mRNA encoding an essential autophagy gene; a morpholino oligonucleotide comprising at least 15 bases and that hybridizes under high stringency conditions to an mRNA encoding an essential autophagy gene; an shRNA comprising at least 15 bases and that hybridizes under high stringency conditions to an mRNA encoding an essential autophagy gene; an agent that decreases expression of an essential autophagy gene; an agent that inhibits an activity of an essential autophagy gene; an agent that inhibits activity of class III PI3 kinase; or a mixture or combination of two or more thereof. In some embodiments, the essential autophagy gene is Atg5 or Atg7. In some embodiments, the shRNA is expressed from a plasmid. In particular examples, the shRNA comprises the sequence shown in SEQ ID NO: 16. In some embodiments, the oligonucleotide, morpholino oligonucleotide or shRNA is at least 80%, at least 85%, at least 90%, at least 95% or at least 99% complementary to the mRNA encoding an essential autophagy gene.

In some embodiments, the medicament is used in combination with enzyme replacement therapy (ERT) for the treatment of the lysosomal storage disorder.

IV. Lysosomal Storage Disorders and Conventional Treatments Therefor

Lysosomal storage disorders are a type of disease involving partial or complete deficiency of a lysosomal hydrolase. This deficiency results in incomplete lysosomal digestion of substrates specific to the hydrolase. Over time, the accumulation of undigested substrate can lead to various abnormalities, including progressive and severe neuro- and muscular-degeneration (see Settembre et al., *Human Mol. Genet.*, 17:119-129, 2008; Fukuda et al., *Curr. Neurol. Neurosci. Rep.*, 7:71-77 2007).

The deficiency in the lysosomal protein usually results in harmful accumulation of a metabolite. For example, in Hurler, Hunter's (Mucopolysaccharidosis II), Morquio's, and Sanfilippo's syndromes, there is an accumulation of mucopolysaccharides; in Tay-Sachs, Gaucher, Krabbe, Niemann-Pick, and Fabry syndromes, there is an accumulation of sphingolipids; and in fucosidosis and mannosidosis, there is an accumulation of fucose-containing sphingolipids and glycoprotein fragments, and of mannose-containing oligosaccharides, respectively.

Enzyme replacement therapy (ERT) as treatment for lysosomal storage diseases (LSDs) was suggested as long ago as 1966 by De Duve and Wattiaux. However, it took >35 years to demonstrate the safety and effectiveness of ERT for a lysosomal storage disorder (type 1 Gaucher disease) (Charrow, *Expert Opin. Biol. Ther.*, 9:121-31, 2009). The principles elaborated in the development of the treatment of Gaucher disease were subsequently applied to the development of ERT of other LSDs. The safety and effectiveness of ERT for Fabry disease (Zarate and Hopkin, *Lancet*, 18:1427-1435, 2008), mucopolysaccharidoses (MPS) I, MPS II and MPS VI (Clarke, *Expert Rev. Mol. Med.*, 10:e1, 2008), as well as for Pompe's disease (van der Beek, *Acta Neurol. Belg.*, 106:82-86, 2006) have been demonstrated in well designed clinical trials, and the treatments are now commercially available (see e.g., Rohrbach and Clarke, *Drugs*, 67:2697-2716, 2007 and Burrow et al., *Curr. Opin. Pediatr.*, 19:628-625, 2007 for review). However, some manifestations of the LSD will not respond to ERT treatment. Additionally, the long-term effectiveness of most of the treatments has not yet been established.

Pompe disease (a.k.a. Glycogenosis type II (GSDII)) is a type of lysosomal storage disorder caused by partial or complete deficiency of lysosomal acid α-glucosidase (GAA). GAA is responsible for the breakdown of glycogen within lysosomes, and enzyme deficiency results in accumulation of glycogen, primarily in skeletal and cardiac muscle. The disease has been separated into two broad categories: infantile onset and late-onset. Patients with the infantile form generally die within the first year of life due to cardiorespiratory failure. The late-onset form presents any time after infancy with generally no cardiac involvement but progressive skeletal muscle myopathy, leading to eventual respiratory failure. It is estimated that 1 in 40,000 individuals have some form of Pompe disease. For a review, see Fukuda et al., *Curr. Neurol. Neurosci. Rep.*, 7:71-77 2007.

ERT treatment of Pompe disease involves intravenous injections of a recombinant GAA (rhGAA) precursor containing mannose-6-phosphate (M6P) groups. Genzyme Corporation sells the commercially available replacement enzyme under the trade name Myozyme® (injectable alglucosidase alfa) and Lumizyme®. The M6P groups bind to cation-independent mannose-6-phosphate receptor (CI-MPR) on the cell surface. The CI-MPR/rhGAA complex internalizes from the cell surface in transport vesicles that fuse with endosomes. In the acidic pH of late endosomes, the rhGAA dissociates from CI-MPR and is transported to the lysosomes, where it rescues the GAA deficiency. ERT for Pompe disease is reviewed, for instance, by Fukuda et al. (*Curr. Neurol. Neurosci. Rep.*, 7:71-77, 2007).

ERT for Pompe disease is effective for glycogen clearance in cardiac muscle, but less effective for glycogen clearance from skeletal muscle (Raben et al., *Acta Myologica*, 26:45-48, 2007). Similarly, in genetically engineered mice that lack expression of GAA (a mouse model of Pompe disease), ERT is effective in clearing gylcogen from type I muscle fibers, but not type II muscle fibers, which predominate in skeletal muscle (Raben et al., *Molecular Therapy*, 11:48-56, 2005).

Fabry disease is an X-linked, hereditary, lysosomal storage disease caused by deficiency of the enzyme alpha-galactosidase A, which results in the accumulation of the neutral glycosphingolipid globotriaosylceramide (Gb3) in the walls of small blood vessels, nerves, dorsal root ganglia, renal glomerular and tubular epithelial cells, and cardiomyocytes. It is a complex, multisystem disorder that is characterized clinically by chronic pain and acroparesthesia, gastrointestinal disturbances, characteristic skin lesions (angiokeratomata), progressive renal impairment, cardiomyopathy, and stroke. Enzyme replacement therapy with intravenous infusions of recombinant human alpha-galactosidase A consistently decreases Gb3 levels in plasma and clears lysosomal inclusions from vascular endothelial cells. The effects of ERT on other tissues are not as obvious, suggesting that treatment must be initiated early in the course of the disease to be optimally effective or that some complications of the disease are not responsive to enzymes delivered intravenously (see Clarke, *Ann. Intern Med.*, 20:425-433, 2007 and Desnick, *Ann. Intern. Med.*, 138:338-346, 2003 for review).

Gaucher disease is an inherited disorder caused by deficient activity of the enzyme glucocerebrosidase, found mainly in lysosomes. This results in an accumulation of glucocerebroside in the lysosomes of macrophages, predominantly in the reticuloendothelial system. Consequences of this abnormal storage include visceral problems such as hepatomegaly, splenomegaly, anaemia and thrombocytopenia causing fatigue, discomfort, infections, bleeding and bruising; bone problems such as pain (acute or chronic) and bone crises, and avascular necrosis; and other problems such as lung disease, impaired growth and delayed puberty. The severity of symptoms and rate of progression vary considerably from patient to patient and range from asymptomatic to severe with early death. Gaucher disease is classified into three subtypes by clinical features. Type I can present at any age and has predominantly visceral symptoms without neurological effects. Type II causes severe progressive brain disease and death occurs in infancy. Type III presents in childhood and has neurological and visceral symptoms. See Connock et al., *Health Technology Assessment*, 10: iii-136, 2004; and Beutler, *PLoS Med.*, 1:e21, 2004.

Imiglucerase (available commercially as Cerezyme™ from Genzyme Corporation) is a recombinant enzyme modified to contain mannose to enhance its uptake into cells and delivery to the lysosomes. It is given intravenously to replace the defective enzyme and is licensed for use in symptomatic type I disease and to treat the visceral symptoms of type III disease. Intravenous Cerezyme® cannot cross the blood-brain barrier and is not effective for neurological manifestations.

Hurler syndrome, also known as mucopolysaccharidosis type I (MPS I), Hurler disease or gargoylism, is a genetic disorder that results in the buildup of mucopolysaccharides due to a deficiency of alpha-L iduronidase, an enzyme responsible for the degradation of mucopolysaccharides in lysosomes (Tolar and Orchard, *Biologics.*, 2:743-751, 2008). Without this enzyme, a buildup of heparan sulfate and dermatan sulfate occurs in the body. Symptoms appear during childhood and early death can occur due to organ damage. MPS I is divided into three subtypes based on severity of symptoms. All three types result from an absence of, or insufficient levels of, the enzyme α-L-iduronidase. MPS I H or Hurler syndrome is the most severe of the MPS I subtypes.

The other two types are MPS I S or Scheie syndrome and MPS I H-S or Hurler-Scheie syndrome. Recombinant alpha-L-iduronidase (IDUA) is used for ERT for MPS I and reduces IDUA substrate accumulation in MPS I Subjects (Tolar and Orchard, *Biologics.*, 2:743-751, 2008).

Hunter Syndrome (Mucopolysaccharidosis II) is a mucopolysaccharidosis (MPS) that is one of a family of inherited disorders of glycosaminoglycan (GAG) catabolism (Neufeld et al., *The Metabolic and Molecular Bases of Inherited Disease*. New York, N.Y.: McGraw-Hill; 3421-3452, 2001). Hunter syndrome is a rare, X-linked disorder. Each MPS is caused by a deficiency in the activity of the distinct lysosomal enzymes required for the stepwise degradation of the GAGs dermatan sulfate, heparan sulfate, keratan sulfate, and chondroitin sulfate (Neufeld et al., *The Metabolic and Molecular Bases of Inherited Disease*. New York, N.Y.: McGraw-Hill; 3421-3452, 2001). In affected patients, undegraded or partially degraded GAG accumulates within lysosomes and is excreted in excess in the urine (Dorfman et al., *Proc Natl Acad Sci USA,* 43:443-4462, 1957). It is the accumulation, or storage, of GAG within lysosomes that contributes to the signs and symptoms of these disorders. MPS is chronic and progressive. The biochemical cause of Hunter syndrome is a deficiency in the activity of the lysosomal enzyme, iduronate-2-sulfatase (I2S), which catalyzes the removal of the sulfate group at the 2 position of L-iduronic acid in dermatan sulfate and heparin sulfate (Bach et al., *Proc. Natl. Acad. Sci. USA.,* 70:2134-2213, 1973; Neufeld et al., *The Metabolic and Molecular Bases of Inherited Disease*. New York, N.Y.: McGraw-Hill; 3421-3452, 2001).

Idursulfase (Elaprase, Shire Human Genetic Therapies, Inc, Cambridge, Mass.) is a recombinant human I2S produced in a human cell line that is approved in the United States and the European Union for the treatment of Hunter syndrome. A Randomized, placebo-controlled, double-blind clinical trial shows a clinical benefit in patients treated with idursulfase compared with patients treated with placebo. Patients treated with idursulfase demonstrate a statistically significant improvement rate compared with placebo. In addition, urine GAG excretion and liver and spleen volumes were significantly reduced from baseline by both idursulfase dosing regimens. Idursulfase was generally well tolerated, and the majority of treatment-emergent adverse events were consistent with the natural history of untreated Hunter syndrome. On the basis of the larger clinical response in the weekly group compared with the EOW group, idursulfase was approved for the treatment of MPS II in both the United States and European Union at a dose of 0.5 mg/kg weekly (see Muenzer et al., *Genet. Med.,* 8:465-473, 2006).

Mucopolysaccharidosis IV (MPS IV; a.k.a. Morquio syndrome), is an autosomal recessive lysosomal storage disorder involving accumulation of keratan sulfate (Tomatsu et al., *Hum. Mol. Genet.,* 17:815-824, 2007). Two forms are recognized: Type A is a deficiency of the enzyme N-acetylgalactosamine-6-sulfate sulfatase; Type B is a deficiency of the enzyme beta-galactosidase. Clinical features are similar in both types but appear milder in Type B. Onset is between ages 1 and 3. Neurological complications include spinal nerve and nerve root compression resulting from extreme, progressive skeletal changes, particularly in the ribs and chest; conductive and/or neurosensitive loss of hearing and clouded corneas. Intelligence is normal unless hydrocephalus develops and is not treated. Physical growth slows and often stops between the ages of 4-8. Skeletal abnormalities include a bell-shaped chest, a flattening or curvature of the spine, shortened long bones, and dysplasia of the hips, knees, ankles, and wrists. ERT with recombinant N-acetylgalactosamine-6-sulfate sulfatase has been used to treat a mouse model of MPSIV that lacks expression of N-acetylgalactosamine-6-sulfate sulfatase (Tomatsu et al., *Hum. Mol. Genet.,* 17:815-824, 2007).

V. Treating Lysosomal Storage Disorders by Inhibiting Autophagy

Autophagy, a major pathway for delivery of proteins and organelles to lysosomes, has been implicated in many cellular and developmental processes and in several human diseases, including lysosomal storage disorders. Disclosed herein is the surprising discovery that inhibition of autophagy is useful as a treatment for lysosomal storage disorders and to enhance conventional treatment of lysosomal storage disorders, including particularly ERT for lysosomal storage disorders. Thus, inhibition of autophagy by reducing the expression of an essential autophagy gene, or by inhibiting the activity of a protein encoded by an essential autophagy gene, can be used for treating a subject with a lysosomal storage disorder and for enhancing conventional treatment of a lysosomal storage disorder, including ERT for the lysosomal storage disorder.

Inhibition of autophagy in a subject can be accomplished in a variety of ways, for example as described herein. Non-limiting examples include the use of a plasmid encoding a shRNA directed to an essential autophagy gene or the use of a compound that inhibits the activity of class III PI3K.

Inhibition of autophagy is contemplated herein for the treatment of Pompe disease, as well as for other lysosomal storage disorders, including for instance GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease, Neuronal Ceroid Lipofuscinoses (CLN6 disease, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pycnodysostosis, Sandhoff disease, Schindler disease, Salla disease/Sialic Acid Storage Disease, Tay-Sachs/GM2 gangliosidosis, or Wolman disease.

Pompe disease, a lysosomal storage disorder caused by deficiency of acid alpha-glucosidase (GAA), can be treated using the methods described herein. Treatment of a subject with Pompe disease can be accomplished by selecting such a subject and inhibiting autophagy in that subject—for instance by applying an inhibitor of an essential autophagy gene, such as an inhibitor of expression of the gene or an inhibitor of an activity of the encoded gene product. In addition, inhibition of autophagy can be used in conjunction with and to enhance conventional ERT treatment for Pompe disease. The conventional treatment for Pompe disease is ERT with recombinant GAA (Myozyme®, Genzyme Corp.), which clears glycogen effectively in the heart, but substantially less so in skeletal muscle. Thus, for instance, treatment of a subject with Pompe disease can be accomplished by selecting a subject undergoing ERT for Pompe disease and inhibiting autophagy in that subject. In either case (that is, whether or not the subject is undergoing ERT), the autophagy can optionally be inhibited only in certain tissues—such as for instance substantially only in the skeletal muscles of the subject.

Described herein are results demonstrating that inhibition of autophagy is useful in treatment of Pompe disease. In various embodiments, an essential autophagy gene (either Atg5 or Atg7) was knocked out in the skeletal muscle of either a mouse model of Pompe disease (the Pompe mouse, in which GAA is knocked out) or wild type (see Example 1). It was surprisingly found that suppression of autophagy alone resulted in diminished glycogen load in Pompe mice. Following ERT, however, the skeletal muscle glycogen was reduced to normal or near normal levels. This successful clearance of lysosomal glycogen has never been observed in Pompe mice with genetically intact autophagy. Furthermore, following ERT, these glycogen-free lysosomes became functionally competent, as evidenced by a dramatic reduction in the level of ubiquitinated proteins.

Agents that inhibit autophagy and thereby treat lysosomal storage diseases can be identified using any one of a number of screening methods known in the art. For example, antisense compounds (such as antisense oligonucleotides, morpholino oligonucleotides, siRNA or shRNAs), small molecules or other compounds can be screened for their capacity to inhibit expression of an essential autophagy gene. To test a candidate compound for its effect on autophagy (as well as Pompe disease) in vivo, the compound can be administered to a GFP-LC3-GAA-/- mouse. These mice, the development of which is described herein, are transgenic mice deficient for GAA and in which an autophagosomal marker (LC3) is tagged with a fluorescent protein (GFP) to monitor autophagy. These mice can be used to monitor autophagy in vivo to facilitate the screening and development of pharmaceuticals that block autophagy.

VI. Genetic Systems for Inhibiting Autophagy

Autophagy, a major pathway for delivery of proteins and organelles to lysosomes, has been implicated in many cellular and developmental processes and in several human diseases, including lysosomal storage disorders. Expression of several gene products is required for autophagy in a cell, including the products of the Atg5, Atg6, Atg7, Atg9, Atg12 and Atg16 genes. Additionally, the activity of many other proteins is required for efficient autophagy in a cell, including the activity of class III PI3K. Thus, one method of inhibiting autophagy is to genetically knockout at least one essential autophagy gene) for instance, Atg5 or Atg7). Cells or organisms containing suck knockouts are useful for instance as model systems for studying lysosomal storage disorders and treatments thereof. In certain example systems, an essential autophagy gene is knocked out only in certain tissues or regions or developmental stages of a subject. For instance, the knockout in some instances is a conditional knockout; example systems for conditionally knocking out genes (particularly essential genes) are known in the art.

An organism carrying a genetic knockout of an essential autophagy gene can be cross bred to another organism (of the same species) carrying a genetic knockout of another gene, such as a gene encoding a lysosomal hydrolase. Thus, in one embodiment an organism (such as a mouse or a primate) in which an essential autophagy gene is knocked out is crossed to another organism (of the same species) that comprises a GAA knockout. In some examples, the essential autophagy gene that is knocked out is Atg7 and the lysosomal hydrolase that is knocked out is GAA; such a system is described in Example 1. A double knockout of an essential autophagy gene and a lysosomal hydrolase can include a conditional knockout of the essential autophagy gene, a conditional knockout of the lysosomal hydrolase encoding gene, or conditional knockouts of both genes. A double knockout of both an essential autophagy gene and a gene encoding a lysosomal hydrolase is useful for studying treatment of lysosomal storage disorders; a representative example of such a system is provided herein.

An organism carrying a genetic knockout of an essential autophagy gene also can be crossbred to another organism of the same species harboring a genetic knockout of a gene encoding a lysosomal hydrolase, for example, alpha-galactosidase A, imiglucerase, alpha-L-iduronidase, idursulfase, N-acetylgalactosamine-6-sulfate sulfatase.

A knockout organism, harboring a knocked out copy of an essential autophagy gene, also can be crossbred to an organism with a genetic knockout of any gene the disruption of which results in a lysosomal storage disorder. Thus there can be combined in a single organism (e.g., by crossbreeding) a double knockout having at least one null essential autophagy gene and a null gene, the disruption of which results in GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome, Morquio Type A/MPS WA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease, Neuronal Ceroid Lipofuscinoses (CLN6 disease, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pycnodysostosis, Sandhoff disease, Schindler disease, Salla disease/Sialic Acid Storage Disease, Tay-Sachs/GM2 gangliosidosis, or Wolman disease.

Methods and techniques for generating knockout, knockin, double knockout and conditional knockout animals, as well as methods of cross-breeding animals are known to those of skill in the art. See, e.g., Nagy et al., Manipulating the Mouse Embryo: A Laboratory Manual, Cold Spring Harbor Laboratory Press; 3rd edition, 2002; and Tymms and Kola (eds), Gene Knockout Protocols, Humana Press; 1st edition, 2001. A mutant knockout animal (e.g., mouse) from which a target gene is functionally deleted can be made by removing all or some of the coding regions of the target gene (e.g., an essential autophagy gene or a gene the disruption of which results in a lysosomal storage disorder) from embryonic stem cells. Methods of creating deletion mutations by using a targeting vector have been described (e.g., Thomas and Capecch, *Cell* 51:503-512, 1987).

For example, to inhibit autophagy only in fast muscle fibers, a critical autophagic gene, such as Atg5, Atg6, Atg7, Atg9, Atg12 or Atg16 can be specifically inactivated in fast muscle by Cre lox-mediated recombination, wherein Cre expression is controlled by the Myosin light chain 1F genomic locus, restricted to fast muscle fibers, and activated from embryonic day ten. Such a knockout can be cross-bred to a knockout of a lysosomal hydrolase, for example, GAA, to generate a double knockout.

In addition to knock-out systems, it is also beneficial to generate "knock-ins" that have lost expression of the wild-type protein but have gained expression of a different, usually mutant form of the same protein. Those of ordinary skill in the relevant art know methods of producing knock-in organisms. See, for instance, Rane et al. (*Mol. Cell Biol.*, 22: 644-656, 2002); Sotillo et al. (*EMBO J.*, 20: 6637-6647, 2001); Luo et al. (*Oncogene*, 20: 320-328, 2001); Tomasson et al. (*Blood*, 93: 1707-1714, 1999); Voncken et al. (, 86: 4603-4611, 1995); Andrae et al. (*Mech. Dev.*, 107: 181-185, 2001); Reinertsen et al. (*Gene Expr.*, 6: 301-314, 1997); Huang et al. (*Mol. Med.*, 5: 129-137, 1999); Reichert et al. (*Blood*, 97: 1399-1403, 2001); and Huettner et al. (*Nat. Genet.*, 24: 57-60, 2000), by way of example.

VII. Gene Suppression for Inhibiting Autophagy

As illustrated herein, a therapeutically effective system for treating a subject having a lysosomal storage disorder involves suppressing expression of at least one gene involved in autophagy, and preferably an essential autophagy gene. This section describes representative methods for reducing or suppressing expression of a protein encoded by an (essential) autophagy gene, and thereby treating a lysosomal storage disorder (such as Pompe disease).

Although the mechanism by which antisense molecules interfere with gene expression may not be fully understood, it is believed that antisense molecules (or fragments thereof) bind to the endogenous mRNA molecules and thereby inhibit translation of the endogenous mRNA or result in its degradation. A reduction of protein expression in a cell may be obtained by introducing into cells an antisense construct based on the Atg5, Atg6, Atg7, Atg9, Atg12, Atg16, or any other essential autophagy gene encoding sequence, including the human (or other mammalian) Atg5 cDNA, Atg6 cDNA, Atg7 cDNA, Atg9 cDNA, Atg12 cDNA, Atg16 cDNA, or any other essential autophagy cDNA or gene sequence or flanking regions thereof. For antisense suppression, a nucleotide sequence from an Atg5- or Atg7-encoding sequence, for example all or a portion of the Atg5 or Atg7 cDNA or gene, is arranged in reverse orientation relative to the promoter sequence in the transformation vector. One of ordinary skill in the art will understand how other aspects of the vector may be chosen.

The introduced antisense sequence need not be the full length of the cDNA or gene, or reverse complement thereof, and need not be exactly homologous to the equivalent sequence found in the cell type to be transformed. Generally, however, where the introduced sequence is of shorter length, a higher degree of homology to the native target sequence will be needed for effective antisense suppression. The introduced antisense sequence in the vector may be at least 15 or at least 20 nucleotides in length, and improved antisense suppression will typically be observed as the length of the antisense sequence increases. The length of the antisense sequence in the vector advantageously may be greater than about 30 nucleotides, or greater than about 100 nucleotides. For suppression of the Atg5, Atg6, Atg7, Atg9, Atg12 or Atg16 gene itself, transcription of an antisense construct results in the production of RNA molecules that are the reverse complement of mRNA molecules transcribed from the endogenous Atg5, Atg6, Atg7, Atg9, Atg12 or Atg16 gene in the cell.

In some embodiments, the antisense compound is a DNA or "DNA-like" oligonucleotide. Such antisense oligonucleotides trigger degradation of a target mRNA by RNAse H, which recognizes DNA:RNA hybrids.

Suppression of an endogenous protein encoded by an essential autophagy gene can also be achieved using ribozymes. Ribozymes are synthetic molecules that possess highly specific endoribonuclease activity. The production and use of ribozymes are disclosed in U.S. Pat. No. 4,987,071 and U.S. Pat. No. 5,543,508. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Suppression can also be achieved using RNA interference, using known and previously disclosed methods. RNA interference (RNAi) is the pathway by which short interfering RNA (siRNA) or shRNA are used to inactivate the expression of target genes (for review see Hannon and Rossi, Nature, 431:371-378, 2004; Tomari and Zamore, *Genes Dev.*, 19:517-529, 2005). shRNA is a single stranded sequence of RNA that makes a tight hairpin turn and can be used to silence gene expression via RNA interference (RNAi). The shRNA hairpin structure is cleaved by the cellular machinery into siRNA. Several models have been put forward to explain RNAi, in particular the mechanisms by which the cleavage derived small dsRNAs or siRNAs interact with the target mRNA and thus facilitate its degradation (Hamilton et al., *Science* 286, 950, 1999; Zamore et al., *Cell* 101, 25, 2000; Hammond et al., *Nature* 404, 293, 2000; Yang et al., *Curr. Biol.* 10, 1191, 2000; Elbashir et al., *Genes Dev.* 15, 188, 2001; *Bass Cell* 101, 235, 2000).

In some embodiments, shRNA or siRNA molecules are expressed from a plasmid vector. For instance the Linearized pGeneClip™ vector (Promega, Corp., Madison, Wis.) is a commercially available system for such expression. This vector uses the U1 promoter to drive shRNA expression and the CMV promoter to drive GFP gene expression. GFP expression allows identification of cells that express this vector. In some elements the nucleic acid encoding a siRNA is inserted into a cassette, where it is operably linked to a promoter. Preferably, the promoter is capable of driving expression of the shRNA or siRNA in cells of the desired target cell/tissue. The selection of appropriate promoters can readily be accomplished. In some embodiments, the promoter is a high expression promoter, for example the 763-base-pair cytomegalovirus (CMV) promoter, the Rous sarcoma virus (RSV) promoter (Davis et al., *Hum. Gene. Ther.* 4:151-159, 1993), or the MMT promoter. By way of example, the promoter can be the U6 promoter, or the U1 promoter.

Other elements that enhance expression also can be included, such as an enhancer or a system that results in high levels of expression, such as a tat gene or tar element. This cassette is inserted into a vector, for example, a plasmid vector such as pUC118, pBR322, or other known plasmid vector, that includes, for example, an *E. coli* origin of replication. See, Sambrook, et al., *Molecular Cloning: A Laboratory Manual*, Cold Spring Harbor Laboratory Press (1989). The plasmid vector may also include a selectable marker such as the β-lactamase gene for ampicillin resistance, provided that the marker polypeptide does not adversely affect the metabolism of the organism being treated. The cassette also can be bound to a nucleic acid binding moiety in a synthetic delivery system, such as the system disclosed in PCT publication WO 95/22618.

It has been proposed that the cleavage derived small dsRNAs or siRNAs act as a guide for the enzymatic complex required for the sequence specific cleavage of the target mRNA. Evidence for this includes cleavage of the target mRNA at regular intervals of ~21-23 nucleotides in the region corresponding to the input dsRNA (Zamore et al., *Cell* 101, 25, 2000), with the exact cleavage sites corresponding to the middle of sequences covered by individual 21- or 22-nucleotide small dsRNAS or siRNAs (Elbashir et al., *Genes Dev.* 15, 188, 2001). Although mammals and lower organisms appear to share dsRNA-triggered responses that involve a related intermediate (small dsRNAs), it is likely that there will be differences as well as similarities in the underlying mechanism. dsRNAs can be formed from RNA oligomers produced synthetically (for technical details see material from the companies Xeragon and Dharmacon, both available on the internet). Small dsRNAs and siRNAs can also be manufactured using standard methods of in vitro RNA production. In addition, the Silencer™ siRNA Construction kit (and components thereof) available from Ambion (Catalog #1620; Austin, Tex.), which employs a T7 promoter and other well known genetic engineering techniques to produce dsRNAs. Double stranded RNA triggers could also be expressed from DNA based vector systems. Programs for siRNA design are known to those of skill in the art and include some, but not all, of the necessary processes required for morpholino design (Henschel, *Nucleic Acids Res.*, 32:W113-W120, 2004; Dudek and Picard, *Nucleic Acids Res.*, 32:W121-W123, 2004; Naito, *Nucleic Acids Res.*, 32:W124-W129, 2004; Yuan et al., *Nucleic Acids Res.*, 32:W130-W134, 2004). Strategies for the design and construction of shRNA expression vectors are also known to those of skill in the art (McIntyre and Fanning, *BMC Biotechnol.*, 6:1, 2006).

The nucleic acids and nucleic acid analogs that are used to suppress an endogenous protein encoded by an essential autophagy gene may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term nucleic acid molecule also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Although particular exemplary sequences are disclosed herein for use as agents for the inhibition of autophagy, one of skill in the art will appreciate that the present methods also encompass sequence alterations of the disclosed agents, as well as other sequences that target autophagy genes, and that yield the same results as described herein. Representative sequence alterations can include, but are not limited to, deletions, base modifications, mutations, labeling, and insertions. Other sequences include other autophagy-involved sequences (e.g., other Atg genes), for instance shRNA or other antisense-type nucleic acid molecules that target any of Atg5, Atg6, Atg7, Atg9, Atg12, Atg16, or any other essential autophagy gene(s).

Suppression of protein expression (and therefor inhibition of autophagy) may also be achieved through agents that enhance proteolysis of a protein encoded by an essential autophagy gene. In other particular examples, the suppression of expression of a protein encoded by an essential autophagy gene involves an agent that enhances the removal of that protein from the cell surface or decreases the transcription, mRNA processing, or translation of that protein.

Also contemplated herein are therapeutic compounds that comprise modified oligonucleotide backbones, for instance modified oligonucleotides that do not include a phosphorus atom but instead have a backbone formed by short chain alkyl or cycloalkyl internucleoside linkages, mixed heteroatom and alkyl or cycloalkyl internucleoside linkages, or one or more short chain heteroatomic or heterocyclic internucleoside linkages. Particularly contemplated are oligonucleotides having morpholino linkages (which is formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for instance, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

In particular embodiments, inhibition of expression autophagy gene(s) (such as an essential autophagy gene) is accomplished using one or more morpholino oligonucleotides. A reduction of protein expression in a cell may be obtained by introducing into the cell a morpholino oligonucleotide based on the Atg5, Atg6, Atg7, Atg9, Atg12, Atg16, or any other essential autophagy gene encoding sequence, including the human (or other mammalian) Atg5 cDNA, Atg6 cDNA, Atg7 cDNA, Atg9 cDNA, Atg12 cDNA, Atg16 cDNA, or any other essential autophagy cDNA or gene sequence or flanking regions thereof. Herein described morpholino-based discoveries and therapeutics find immediate application in the management and treatment of lysosomal storage disorders, for instance, Pompe disease. By way of example, a morpholino can be delivered systemically or in a tissue- or cell-targeted manner. Morpholinos can also be incorporated into (or onto) an implanted device for sustained local release, for instance.

Morpholinos are synthetic molecules which are the product of a redesign of natural nucleic acid structure (Summerton and Weller, *Nucleic Acid Drug Development*, 7:87-95, 1997). Usually about 25 bases in length, they bind to complementary sequences of RNA by standard nucleic acid base-pairing. Structurally, the difference between morpholinos and DNA is that while morpholinos have standard nucleic acid bases, those bases are bound to morpholine rings instead of deoxyribose rings and linked through phosphorodiamidate groups instead of phosphates (Summerton and Weller, *Nucleic Acid Drug Development*, 7:87-95, 1997). The entire backbone of a morpholino is made from these modified subunits. Morpholinos are most commonly used as single-stranded oligonucleotides, though heteroduplexes of a morpholino strand and a complementary DNA strand may be used in combination with cationic cytosolic delivery reagents (Morcos, *Genesis*, 30:94-102, 2001). Morpholinos do not degrade their target RNA molecules, unlike many antisense structural types (e.g. phosphorothioates, siRNA, etc.). Instead, morpholinos act by "steric blocking", binding to a target sequence within a RNA and simply getting in the way of molecules which might otherwise interact with the RNA (Summerton, *Biochimica et Biophysica Acta*, 1489:141-58, 1999). See also U.S. Pat. No. 5,506,337 (which describes a morpholino-subunit combinatorial library and related methods).

The effect morpholinos have on the expression of a target sequence is determined by the position targeted within a nucleotide sequence. Morpholinos targeting the 5'-untranslated regions (5'-UTRs) in proximity to the translational initiation site (TIS) disrupt ribosomal complex formation and inhibit protein translation of mRNA, while morpholinos targeting pre-mRNA splice sites can induce alternative splicing events (Gebski et al., *Mol. Genet.*, 12:1801-1811, 2003; Ekker and Larson, *Genesis*, 30:89-93, 2001; Draper et al., *Genesis*, 30:154-156, 2001).

Programs for siRNA design include some, but not all, of the processes involved in morpholino design. See, for instance, Henschel, *Nucleic Acids Res.*, 32:W113-W120, 2004; Dudek and Picard, *Nucleic Acids Res.*, 32:W121-W123, 2004; Naito, *Nucleic Acids Res.*, 32:W124-W129, 2004; and Yuan et al., *Nucleic Acids Res.*, 32:W130-W134, 2004. Both siRNA and morpholino design require computation of biochemical properties of short oligonucleotides, including base composition and homogeneous nucleotide run calculations. However, siRNA does not require a detailed analysis of oligonucleotide binding position relative to target nucleotide sequence features.

Multiple programs for morpholino-specific design are available and known to one of skill in the art and provide the user with a range of potential oligonucleotide designs suitable for use in a variety of biological applications, including use as inhibitors of mRNA translation or for the alteration of pre-mRNA splicing (Klee et al., *Nucleic Acids Res.*, 33: W506-511, 2005). Such programs include, for example, AMOD (Klee et al., *Nucleic Acids Res.*, 33: W506-511, 2005) and the design services offered by Gene-Tools, LLC (Philomath, Oreg.). Morpholino oligonucleotide synthesis services are available commercially; for example, from Gene-Tools, LLC. (Philomath, Oreg.).

For a morpholino to be effective, it is delivered past the cell membrane into the cytosol of a cell. Once in the cytosol, morpholinos freely diffuse between the cytosol and nucleus. Different methods are used for delivery into embryos, into cultured cells or into adult animals. A microinjection apparatus is usually used for delivery into an embryo, with injections most commonly performed at the single-cell or few-cell stage; an alternative method for embryonic delivery is electroporation, which can deliver oligonucleotides into tissues of later embryonic stages (Cerda et al., *Methods*, 39:207-11, 2006). Common techniques for delivery into cultured cells include the Endo-Porter peptide (which causes the morpholino to be released from endosomes; Summerton, *Ann. N.Y. Acad. Sci.*, 1058:62-75, 2005), the Special Delivery system (using a morpholino-DNA heteroduplex and an ethoxylated polyethylenimine delivery reagent; Morcos, *Genesis*, 30:94-102, 2001), Electroporation (Jubin, *Methods Mol. Med.*, 106:309-22, 2004) or scrape loading (Partridge et al., *Antisense Nucleic Acid Drug Dev.*, 6:169-75, 1996). In some embodiments, unmodified morpholino oligonucleotides are delivered into adult tissues according to procedures known to those of skill in the art (Fletcher et al., *J. Gene. Med.*, 8:207-16, 2006; Kipshidze et al., *Am. Coll. Cardiol.*, 39:1686-91, 2002).

Though they permeate through intercellular spaces in tissues effectively, unconjugated morpholinos have limited distribution into the cytosol and nuclear spaces within healthy tissues following intravenous administration. Systemic delivery into many cells in adult organisms can be accomplished by using covalent conjugates of morpholino oligonucleotides with cell penetrating peptides (Abes et al., *J. Control Release*, 116:304-13, 2006; Burrer et al., *J. Virol.*, 81: 5637-48, 2007), which have been used in vivo for effective oligonucleotide delivery (Deas et al., *Antimicrob. Agents Chemother.*, 51:2470, 2007; Amantana et al., *Bioconjug. Chem.*, 18:1325, 2007). An octa-guanidinium dendrimer attached to the end of a morpholino can also be used to deliver the modified oligonucleotide (called a Vivo-Morpholino) from the blood to the cytosol (Li and Morcos, *Bioconjug. Chem.*, 19:1464-70, 2008; Morcos et al., *BioTechniques* 45:616-26, 2008). Delivery-enabled morpholinos, such as peptide conjugates and Vivo-Morpholinos, show promise as therapeutics (Moulton and Jiang, *Molecules*, 14:1304-23, 2009).

VIII. Compounds for Inhibition of Autophagy

Also provided herein are methods of inhibiting autophagy using a chemical inhibitor, for instance a therapeutic molecule that reduces or suppresses (directly or indirectly) the activity of a protein required for autophagy or for the formation of autosomes. Any chemical inhibitor of autophagy may be useful. In certain embodiments, a chemical inhibitor that inhibits sequestration of cytosolic protein (and other content) into autophagosomes is used.

By way of example, in some specific methods the chemical inhibitor is an inhibitor of PI3K; for example an inhibitor of class III PI3K. One such inhibitor is 3-Methyladenine (3-MA) Inhibition of class III PI3 kinase activity using 3-MA inhibits autophagy and has been used to inhibit autophagy in tissue culture (see Seglen and Gordon, *Proc. Natl. Acad. Sci. U.S.A.*, 79:1889-1892, 1982 and Hamacher-Brady et al., *J. Biol. Chem.*, 281: 29776-29787, 2006), though prior to this disclosure it was not used in vivo or in a therapeutic setting. 3-MA is available commercially (Sigma Catalog Number M9281). Other contemplated inhibitors of PI3K are also available commercially, including LY294002 (Cell Signalling Cat. No. 9901) and Wortmannin.

Other inhibitors of autophagy include sequestration inhibitors (for example, cycloheximide), microtubule poisons (for example, vinblastine), lysosomal enzyme inhibitors (for example, E64d or leupeptin), and lysosomal pH elevators (for example, Bafilomycin A1 or chloroquine). Bafilomycin is another contemplated inhibitor of autophagy; this molecule is a proton pump inhibitor that inhibits fusion between autophagosomes and lysosomes (see, e.g., Yamamoto et al., *Cell Struct. Funct.* 23:33-42, 1998). Small molecule inhibitors of the proteins of the autophagy apparatus are also useful for inhibiting autophagy. Lithium and trehalose also may be useful, though in certain circumstances they enhance autophagy.

It will be appreciated that chemical inhibitor(s) of autophagy can be administered systemically or locally, and may optionally be targeted to specific cell/tissue/organ(s), for instance by inclusion with or binding to targeting moieties.

IX. Spatially- and/or Temporally-Limited Inhibition of Autophagy

In various embodiments, autophagy is inhibited locally, while in others it is inhibited systemically. For example, autophagy inhibition can be limited to certain regions or tissues of a subject. The choice of tissue(s) or region(s) or organ(s) to direct autophagy inhibition towards is influenced by the subject, the disease being treated, the compound(s)/agent(s) being administered, and so forth.

For example, in a subject with Pompe disease, such as one undergoing ERT for Pompe disease, it is particularly desirable to inhibit autophagy in skeletal muscle. Thus, it is understood that inhibition may be limited to a particular tissue or particular tissues in the methods described herein. For example, in some embodiments autophagy is inhibited in skeletal muscle. In other embodiments, autophagy is specifically not inhibited in neurons.

Targeted inhibition of autophagy can be accomplished by a variety of means known to those of skill in the art for targeting agents to specific cells/tissues/organs. Any method that results in the contact of an autophagy inhibitor with a desired tissue can be used to target that autophagy inhibitor to the target tissue. For example, an autophagy inhibiting compound (e.g., a small molecule inhibitor, oligonucleotide, morpholino, shRNA or plasmid encoding a shRNA) can be directly injected into a region or tissue of a subject; for example skeletal muscle. Following injection, delivery of the autophagy inhibitor can be enhanced by electroporation (Schertzer, *Mol. Ther.*, 13:795-803, 2006).

For example, targeted inhibition of autophagy can be accomplished through direct injection of a plasmid encoding a shRNA directed to an essential autophagy gene (for example, Atg5 or Atg7) in to a particular tissue, for example, skeletal muscle.

Alternatively, targeted inhibition of autophagy can be accomplished by directly injecting an inhibitor of class III PI3K activity into a region or tissue of a subject; for example, skeletal muscle. In some instances, the PI3K inhibitor is an inhibitor of class III PI3K. In some embodiments, injection of a class III PI3K inhibitor occurs in skeletal muscle.

Similarly, it is beneficial in certain circumstances to inhibit autophagy only at certain times (that is, temporally limited autophagy inhibition). For instance, it may be beneficial to inhibit autophagy in a subject with a lysosomal storage disease only at certain stages of the disease, or only when the subject is of a certain age or age range (e.g., infant, child, young adult, adult, etc.). Optionally, spatial and temporal limitations may be applied together, for instances such that inhibition of autophagy is only induced in a subject that is adult and only in skeletal muscles.

X. Pharmaceutical Compositions

The therapeutic compounds (e.g., siRNAs, shRNAs or plasmids encoding them, morpholinos, small molecule inhibitors, inhibitors of class III PI3K, and so forth) described herein may be formulated in a variety of ways depending on the location and type of disease to be treated or prevented in the subject. Pharmaceutical compositions are thus provided for both local use at or near an affected area and for systemic use (in which the agent is administered in a manner that is widely disseminated via the cardiovascular system). This disclosure includes within its scope pharmaceutical compositions including antisense molecules, morpholino oligonucleotides, and class III PI3K inhibitors, or combinations thereof, that are formulated for use in human or veterinary medicine. For example, the provided pharmaceutical compositions may include compositions comprising plasmids encoding shRNA, siRNA, or morpholino oligonucleotides useful to inhibit expression of Atg5, Atg6, Atg7, Atg9, Atg12 or Atg16. Alternatively, the pharmaceutical compositions may contain small molecule inhibitors of class III PI3K. While the autophagy inhibitors typically will be used to treat human subjects, they may also be used to treat similar or identical diseases in other vertebrates, such other primates, dogs, cats, horses, and cows.

Pharmaceutical compositions that include at least one shRNA or oligonucleotide encoding an shRNA or morpholino or other autophagy inhibitor or therapeutic compound as described herein as an active ingredient, or that include a mixture of two or more thereof, with or without additional agent(s) as active ingredients, may be formulated with an appropriate solid or liquid carrier, depending upon the particular mode of administration chosen. Additional active ingredients include, for example, lysosomal hydrolase compositions useful for enzyme replacement therapy for a lysosomal storage disorder. For example, a pharmaceutical composition may comprise recombinant human GAA modified to comprise mannose-6-phosphate. Alternatively, a pharmaceutical composition may comprise recombinant or purified alpha-L-iduronidase, iduronate-2-sulfatase or N-acetylgalactosamine-6-sulfate sulfatase. A pharmaceutical composition may comprise any of the enzymes deficient in a lysosomal storage disorder selected from GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease, Neuronal Ceroid Lipofuscinoses (CLN6 disease, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pycnodysostosis, Sandhoff disease, Schindler disease, Salla disease/Sialic Acid Storage Disease, Tay-Sachs/GM2 gangliosidosis, or Wolman disease.

The dosage form of the pharmaceutical composition will be influenced by the mode of administration chosen. For instance, in addition to injectable fluids, inhalational, topical, opthalmic, peritoneal, and oral formulations can be employed. Inhalational preparations can include aerosols, particulates, and the like. In general, the goal for particle size for inhalation is about 1 µm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the compounds for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the compounds can be, for example, mixed with a liquid delivery agent for administration locally. The agents used therapeutically (such as shRNA or oligonucleotide encoding an shRNA or morpholino or other inhibitor or therapeutic compound as described herein) are readily soluble or suspendable in water and saline, and as such these would be useful for delivery since water or saline do not cause adverse biological tissue effects. This allows sufficiently high doses to be administered locally or systemically, without secondary toxicity from the delivery vehicle.

Pharmaceutical compositions that comprise at least one therapeutic agent as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, therapeutic agent(s) can be formulated generally by mixing them at the desired degree of purity, in a unit dosage injectable form (solution, suspension, or emulsion), with a pharmaceutically acceptable carrier, for instance, one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the therapeutic agent(s) each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise at least one therapeutic agent, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

Optionally, the pharmaceutical compositions may be used with a microdelivery vehicle such as cationic liposomes and adenoviral vectors (for a review of the procedures for liposome preparation, targeting and delivery of contents, see Mannino and Gould-Fogerite, *BioTechniques*, 6:682, 1988; Feigner and Holm, *Bethesda Res. Lab. Focus*, 11(2):21, 1989; and Maurer, *Bethesda Res. Lab. Focus*, 11(2):25, 1989). Replication-defective recombinant adenoviral vectors can be produced in accordance with known techniques (see Quantin, et al., *Proc. Natl. Acad. Sci. USA*, 89:2581-2584, 1992; Stratford-Perricadet, et al., *J. Clin. Invest.*, 90:626-630, 1992; and Rosenfeld, et al., *Cell*, 68:143-155, 1992).

Preparations for administration can be suitably formulated to give controlled release of the therapeutic agent(s) (e.g., siRNAs, shRNAs or plasmids encoding them, morpholinos, small molecule inhibitors of class III PI3K and so forth). For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See, for example, U.S. Pat. No. 5,700,486.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic peptide as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-

342, 1994; Tice & Tabibi, *Treatise on Controlled Drug Delivery*, A. Kydonieus, ed., Marcel Dekker, Inc. New York, N.Y., pp. 315-339, 1992).

Also contemplated is the use of nanoparticles as delivery agents, which can be targeted to specific cells, tissues or organ for instance by incorporation on their surface ligands of receptors specific in their expression to the targeted cells, tissues or organs. The targeting entity can be the same or different than the therapeutically active agent carried by the nanoparticle. Further, distribution of nanoparticles to certain tissues spaces (e.g. the blood versus the central nervous system protected by the blood-brain barrier) can be determined by altering the size of the nanoparticles thereby allowing or preventing their transit of such barriers between tissue compartments.

Polymers can be used for controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of lipid-capsulated compounds (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188, 837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514, 670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

XI. Methods of Treatment/Use in a Clinical Setting

With the provision herein of the discovery that inhibiting autophagy results in therapeutic benefits in a subject with a lysosomal storage disorder, for instance Pompe disease, clinical use of autophagy inhibition for such diseases is now enabled. Generally, the method involves selecting a subject with a lysosomal storage disorder and inhibiting autophagy in that subject, thereby treating the lysosomal storage disorder. Various ways of selecting a subject with a lysosomal storage disorder are disclosed, including selecting a subject with Pompe disease, Fabry disease or Hunter syndrome. Methods of selecting a subject with a lysosomal storage disorder will be apparent to one of skill in the art.

This section also describes the administration of an agent that inhibits autophagy to a subject. For example, administration of plasmid encoding shRNA directed to an essential autophagy gene is disclosed. Administration of small molecule compounds that inhibit class III PI3K inhibitors is disclosed. The skilled artisan will recognize appropriate administration procedures.

Selecting a Subject with a Lysosomal Storage Disorder

Techniques for identifying a subject with a lysosomal storage disorder (that is, diagnosing the disorder) are known to those of skill in the art. Preliminary diagnosis can include an evaluation of a subject's symptoms. Clinical diagnosis can include analysis of lysosomal hydrolase activity in a sample from a subject, including a blood sample, such as a dried blood sample (see U.S. Pat. No. 7,378,231 and U.S. Pat. No. 7,563,591, for example). In some instances, clinical diagnosis comprises genetic evaluation of a subject, for instance detection of a recognized or known genetic aberration that result in the lysosomal storage disorder. Example disorders and representative (but non-limiting) diagnostic methods are provided below.

Pompe disease is an autosomal recessive disorder of glycogen metabolism that is characterized by a deficiency of the lysosomal acid α-glucosidase. Early diagnosis before the onset of irreversible pathology is thought to be critical for maximum efficacy of current and proposed therapies (Umapathysivam et al., *Clin. Chem.*, 47:1378-1383, 2001). The clinical diagnosis of Pompe disease is confirmed by the virtual absence, in infantile onset, or marked reduction, in juvenile and adult onset, of acid α-glucosidase activity in leukocytes (Taniguchi et al., *Clin. Chim. Acta.*, 89:293-299, 1978; Dreyfus et al., *Pediatr. Res.*, 14:342-344, 1980), muscle biopsies (Ninomiya et al., *J. Neurol. Sci.*, 66:129-139, 1984; Ausems et al., *Neurology*, 52:851-853, 1999), cultured fibroblasts (Shin et al., *Clin. Chim. Acta.*, 148:9-19, 1985) and the measurement of acid α-glucosidase activity in dried-blood spots (Umapathysivam et al., *Clin. Chem.*, 47:1378-1383, 2001; Chien et al., *Pediatrics*, 122:e39-45, 2008). Where a family history is known, prenatal diagnosis can be made by determining the acid α-glucosidase activity in cultured amniotic cells and/or in chorionic villus biopsies (Park et al., *Prenat. Diagn.*, 12:169-173, 1992) and also by mutation analysis (Grubisic et al., *Clin. Genet.*, 30:298-301, 1986; Kleijer et al., *Pediatr. Res.*, 38:103-106, 1995).

Fabry disease can be diagnosed reliably in males by markedly deficient or absent α-Gal A activity in plasma or peripheral leukocytes by using commercially available 4-methylumbelliferyl-α-d-galactoside as substrate (Desnick et al., *J. Lab. Clin. Med.*, 81:157-71, 1973). To inhibit cross-reactivity with α-galactosidase B, the α-Gal A assay mixture must include 500 mmol of N-acetylgalactosamine per L (Mayes et al., *Clin. Chim. Acta.*, 112:247-51, 1981). Normal enzyme values differ depending on the enzyme source, substrate concentrations, and assay variables. Carrier detection with the α-Gal A assay is not reliable because some obligate heterozygotes have normal α-Gal A activity. Thus, all women at risk for carrying the disease gene should have molecular studies to detect the family's mutation. Fabry disease can be diagnosed prenatally by demonstration of an XY karyotype and deficient α-Gal A activity in cultured amniocytes or chorionic villi (Brady, *Science*, 172:174-5, 1971). If the family's α-Gal A mutation is known, molecular studies can replace or confirm the enzymatic diagnosis.

Hunter Syndrome is a mucopolysaccharidosis (MPS) that is one of a family of inherited disorders of glycosaminoglycan (GAG) catabolism (Neufeld et al., *The Metabolic and Molecular Bases of Inherited Disease*. New York, N.Y.: McGraw-Hill; 3421-3452, 2001). Each MPS is caused by a deficiency in the activity of the distinct lysosomal enzymes required for the stepwise degradation of the GAGs dermatan sulfate, heparan sulfate, keratan sulfate, and chondroitin sulfate (Neufeld et al., *The Metabolic and Molecular Bases of Inherited Disease*. New York, N.Y.: McGraw-Hill; 3421-3452, 2001). In affected patients, undegraded or partially degraded GAG accumulates within lysosomes and is excreted in excess in the urine (Dorfman et al., *Proc Natl Acad Sci USA*, 43:443-4462, 1957). It is the accumulation, or storage, of GAG within lysosomes that contributes to the signs and symptoms of these disorders. MPS is chronic and progressive. A newborn infant may appear normal, and yet, within a few years progress into a physically abnormal and mentally impaired individual. MPS is rare and occurs in people of all ethnicities, with an estimated prevalence of between 3.4 and 4.5 per 100 000 births (Martin et al., Pediatrics, 121:e377-386, 2008). The biochemical cause of Hunter syndrome is a deficiency in the activity of the lysosomal enzyme, iduronate-2-sulfatase (I2S), 10 which catalyzes the removal of the sulfate group at the 2 position of L-iduronic acid in dermatan sulfate and heparan sulfate (Bach et al., *Proc. Natl. Acad. Sci. USA.*, 70:2134-2213, 1973; Neufeld et al., *The Metabolic and Molecular Bases of Inherited Disease*. New York, N.Y.: McGraw-Hill; 3421-3452, 2001).

Few if any signs and symptoms of Hunter syndrome will be present at birth and will only begin to emerge after several years. The initial suspicion of Hunter syndrome is often based on facial features and is made by the physician/health care provider during an examination for other issues. Analysis of urine GAG levels can be used to confirm the suspicion of MPS. As in almost all cases of MPS, the total urinary GAG level is increased. The presence of excess dermatan sulfate and heparan sulfate in urine is evidence that MPS I, MPS II, or MPS VII is present (Martin et al., *Pediatrics*, 121:e377-386, 2008; Neufeld et al., *The Metabolic and Molecular Bases of Inherited Disease*. New York, N.Y.: McGraw-Hill; 3421-3452, 2001); however, it is not diagnostic of Hunter syndrome, so additional tests must be performed. A negative urine GAG test does not necessarily rule out a diagnosis of Hunter syndrome, because false-negative results can occur as a result of a lack of sensitivity of the testing method.

I2S is present in all cells (except mature red blood cells); therefore, enzyme activity can be measured in a variety of cells and body fluids. Assays based on cultured fibroblasts, leukocytes, plasma, or serum are commonly used; the choice depends on the preference of the testing facility. Methods that are based on the analysis of dried blood spots are known to those of skill in the art and may be used primarily for screening purposes (Dean et al., *Clin. Chem.*, 52:643-649, 2006; Civallero et al., *Clin. Chim. Acta.*, 372:98-102, 2006). Absent or low I2S activity in males is diagnostic of Hunter syndrome, provided that another sulfatase is measured and it has normal activity, which would rule out multiple sulfatase deficiency. Absolute enzyme activity cannot be used to predict the severity of the phenotype. Enzyme activity cannot be used to identify female carriers because, although on average I2S activity in female carriers is ~50% of that seen in nonaffected individuals, considerable overlap exists (Lin et al., *Clin. Chim. Acta.*, 369:29-3431, 2006). Mutation analysis is necessary to confirm carrier status in females.

Mutation analysis may be used to confirm Hunter syndrome in males. Gene analysis is the only secure way to identify female carriers and could be used for prenatal diagnosis, increasing the importance of being able to identify the mutation in every family. Mutations that result in complete absence of the enzyme or its activity are commonly associated with Hunter syndrome with neurologic involvement.

Prenatal diagnosis: Enzyme activity assays may be conducted on cells that are cultured from amniotic fluid or in chorionic villus biopsy tissue or fetal blood (Keulemans et al., *Prenat. Diagn.*, 22:1016-1021, 2002; Archer et al., *Prenat. Diagn.*, 4:195-200, 1984; Pannone et al., *Prenat. Diagn.*, 6:207-210, 1986; Cooper et al., *Prenat. Diagn.*, 11:731-735, 1991). In addition, prenatal diagnosis can be performed by using molecular analysis if the family specific mutation is known (Bunge et al., *Prenat. Diagn.* 14:777-780, 1994; Grosso et al., *Biochem. Mol. Biol. Int.*, 35:1261-1267, 1995).

Differential Diagnosis Analysis of urinary GAG composition may be used to discriminate among the different MPS disorders (Neufeld et al., *The Metabolic and Molecular Bases of Inherited Disease*. New York, N.Y.: McGraw-Hill; 3421-3452, 2001; Martin et al., *Pediatrics*, 121:e377-386, 2008). However, it cannot distinguish between MPS I and MPS II, and it cannot be used to discriminate between subtypes of individual MPSs.

Administration to a Subject

Suitable administration format and regimens are within the ordinary skill of medical practitioner, and are beneficially tailored to fit the disease, subject or situation individually. Representative examples are provided herein, but are not intended to be limiting.

Various pharmaceutically acceptable carriers and their formulation are described in standard formulation treatises, for example, *Remington's Pharmaceutical Sciences* by E. W. Martin. See also Wang and Hanson, *J. Parenteral Sci. Technol.*, Technical Report No. 10, Supp. 42: 2S, 1988.

The dosage form of the pharmaceutical composition will be influenced by the mode of administration chosen. For instance, in addition to injectable fluids, inhalational, topical, opthalmic, peritoneal, and oral formulations can be employed. Inhalational preparations can include aerosols, particulates, and the like. In general, the goal for particle size for inhalation is about 1 µm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The therapeutically effective amount of therapeutic agent, such as siRNAs, shRNAs or plasmids encoding shRNA, morpholinos, small molecule inhibitors of class III PI3K, and so forth or other inhibitor or therapeutic compound as described herein will be dependent on the particular compound utilized, the subject being treated, the severity and type of the affliction, and the manner of administration. The exact dose is readily determined by one of skill in the art based on the potency of the specific compound, the age, weight, sex and physiological condition of the subject. Representative dosages are provided herein.

The specific form of the therapeutic agents and their manner of administration depends in part upon the particular tissue to be treated. The compounds or pharmaceutical compositions containing them can be administered intramuscularly, for example, or via other forms of administration known to one of skill in the art, as appropriate.

The amount of agent to be delivered, as well as the dosing schedule necessary to provide the desired inhibition of autophagy effects, will also be influenced by the bioavailability of the specific compound selected (and/or an active metabolite thereof), the type and extent of radiation exposure or radiation dosage schedule, and other factors that will be apparent to those of skill in the art.

Therapeutically effective dosages of plasmid encoding shRNA directed to an essential autophagy gene will be a function of the particular plasmid, the particular essential autophagy gene, the target tissue, the subject, and his or her clinical condition. Effective amounts of plasmid encoding a shRNA directed to an essential autophagy gene are generally in the range of between about 1 and 4000 µg, or about 1000 and 2000 µg, or between about 2000 and 4000 µg. For example, as described in Example 2, 80 µg of plasmid DNA encoding shRNA directed to Atg5 can be injected into muscle at a concentration of (2 μg/p1) in saline solution. Plasmid DNA can be injected into skeletal muscle, for instance tibialis anterior (TA) muscle. Following injection, electroporation can be used to enhance delivery of the plasmid DNA to muscle cells (Schertzer et al., *Mol. Ther.*, 13:795-803, 2006). Electroporation of the plasmids into the muscles can be done by placing electrodes at a right angle to the longitudinal axis of the muscle and a train of short currents delivered: three transcutaneous pulses (each 20 ms in duration) across the muscle at a voltage of 75-100V. The polarity is then reversed and three more pulses delivered (Schertzer et al., *Mol. Ther.*, 13:795-803, 2006).

Exact dosage amounts of plasmid DNA encoding shRNA directed to an essential autophagy gene will vary by the size and other characteristics of the subject being treated, the duration of the treatment, the mode of administration, the transfection rate and gene suppression efficiency and the gene to be suppressed. Doses for systemic administration of plasmid DNA encoding shRNA directed to an essential autophagy gene in mammalian species can readily be determined using standard pharmacokinetic and/or pharmacodynamic methods.

The effective dose of a nucleic acid will be a function of the particular expressed protein, the target tissue, the subject, and his or her clinical condition. Effective amounts of DNA are between about 1 and 4000 μg, or about 1000 and 2000 μg, or between about 2000 and 4000 μg. In certain situations, it is desirable to use nucleic acids encoding both a shRNA and a protein (for example, GFP) or two or more different proteins in order to optimize the therapeutic outcome. In order to facilitate administration, the nucleic acid may be formulated with a pharmaceutically acceptable carrier. Examples of suitable carriers include, but are not limited to, saline, albumin, dextrose and sterile water.

Therapeutically effective dosages of morpholino oligonucleotides are generally in the range of 0.1-1000 μM, or 1-100 μM, or 1-10 μM, for instance. Alternatively, dosages may be in the range of about 100 nM to 1500 nM, for instance about 200 nM, about 300 nM, about 400 nM, about 500 nM, about 750 nM, about 1000 nM, about 1200 nM, about 1300 nM, or about 1400 nM. Exact dosage amounts will vary by the size and other characteristics of the subject being treated, the duration of the treatment, the mode of administration, and so forth. Doses for systemic administration of the morpholino in other species can readily be determined using standard pharmacokinetic and/or pharmacodynamic methods. Morpholino oligonucleotides have been administered to a subject both locally and systemically (see, e.g., Wheeler et al., *Science*, 325:336-339, 2009; Alter et al., *Nature Med.* 12:175-177, 2006;).

Therapeutically effective dosages of small molecule inhibitors of PI3K will depend on the particular inhibitor and the administration method selected. Therapeutically effective dosages of 3-Methyladenine are generally in the range of 0.01% to 10% or 0.1% to 10% or 5% to 10% intraperitoneal $LD_{50}$ dose (280 mg/kg) into TA muscle. 3-Methyladenine is available commercially from Sigma (Cat. No. M9281).

The therapeutic agents may be administered directly as part of a surgical or other medical procedure, or by a treating physician. Drug quality product (e.g., siRNAs, shRNAs or plasmids encoding them, morpholinos, small molecule inhibitors of class III PI3K, and so forth or other inhibitor of autophagy) can be diluted for instance in sterile saline and given by injection using sterile 1 cc syringes and small bore needles (25 gauge and less) to a subject having a lysosomal storage disorder, or a subject optionally undergoing ERT.

Active compounds (e.g., siRNAs, shRNAs or plasmids encoding them, morpholinos, small molecule inhibitors of class III PI3K and so forth) are also suitably administered by sustained-release systems. Examples of sustained-release formulations include suitable polymeric materials (such as, for example, semi-permeable polymer matrices in the form of shaped articles, for example, films, or mirocapsules), suitable hydrophobic materials (for example as an emulsion in an acceptable oil) or ion exchange resins, and sparingly soluble derivatives (such as, for example, a sparingly soluble salt). Sustained-release compounds may be administered by intravascular, intravenous, intra-arterial, intramuscular, subcutaneous, intra-pericardial, or intra-coronary injection. Administration can also be oral, rectal, parenteral, intracisternal, intravaginal, intraperitoneal, topical (as by powders, ointments, gels, drops or transdermal patch), buccal, or as an oral or nasal spray.

In some embodiments, therapeutic agent(s) are delivered by way of a pump (see Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution may also be employed. The key factor in selecting an appropriate dose is the result obtained, as measured by decreases in autophagy, or by other criteria for measuring control or prevention of disease, as are deemed appropriate by the practitioner. Other controlled release systems are discussed in the review by Langer (*Science* 249: 1527-1533, 1990).

In another aspect of the disclosure, therapeutic agent(s) are delivered by way of an implanted pump, described, for example, in U.S. Pat. No. 6,436,091; U.S. Pat. No. 5,939,380; and U.S. Pat. No. 5,993,414 Implantable drug infusion devices are used to provide subjects with a constant and long term dosage or infusion of a drug or any other therapeutic agent. Essentially, such device may be categorized as either active or passive.

The implanted pump can be completely implanted under the skin of a subject, thereby negating the need for a percutaneous catheter. These implanted pumps can provide the patient with therapeutic agent(s) at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

The therapeutic agents may also be delivered passively and in sustained fashion as part of and incorporated into implantable devices, such as vascular stents which can be placed directly into diseased blood vessels through several standard approaches, including direct surgical insertion or percutaneously with angiographic control.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump the drug out from the reservoir, and a catheter port to transport the pumped out drug from the reservoir via the pump to a patient's anatomy. Such devices also typically include a battery to power the pump, as well as an electronic module to control the flow rate of the pump. The Medtronic SynchroMed™ pump further includes an antenna to permit the remote programming of the pump.

Passive drug infusion devices, in contrast, do not feature a pump, but rather rely upon a pressurized drug reservoir to deliver the drug. Thus, such devices tend to be both smaller as well as cheaper as compared to active devices. An example of such a device includes the Medtronic IsoMed™. This device delivers the drug into the patient through the force provided by a pressurized reservoir applied across a flow control unit.

Also provided are autoinjectors comprising a pharmaceutical composition consisting of agent that inhibits autophagy (such as a peptide or antibody, or morpholino or other nucleic acid molecule, as described herein) and a suitable excipient. Suitable excipients, for example, are composed of water, propylene glycol, ethyl alcohol, sodium benzoate and benzoic acid as buffers, and benzyl alcohol as preservative; or of mannitol, human serum albumin, sodium acetate, acetic acid, sodium hydroxide, and water for injections. Other exemplary compositions for parenteral administration include solutions or suspensions that may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

In one embodiment, the autoinjector contains a sterile solution packaged within a syringe-like device that delivers its entire 1 ml to 5 ml contents automatically upon activation. Each milliliter contains 100 µg, or in some embodiments 200 µg, of autophagy inhibiting agent (e.g., 3-MA, a morpholino, or a plasmid encoding an shRNA directed to an essential autophagy gene) with an excipient, such as an excipient comprising propylene glycol, ethyl alcohol, sodium benzoate and benzoic acid as buffers, and benzyl alcohol as preservative.

Additional information regarding possible modes and methods for administration is found throughout this document.

XII. Combination Therapy, and Enhancement of ERT

Also provided is a method of treating a subject having a lysosomal storage disorder wherein the subject is undergoing ERT. Generally, the method involves selecting a subject with a lysosomal storage disorder and inhibiting autophagy in that subject, thereby treating the lysosomal storage disorder. Various ways of selecting a subject with a lysosomal storage disorder wherein the subject is undergoing ERT are disclosed, including selecting a subject with Pompe disease undergoing ERT. Generally, selecting a subject with a lysosomal storage disorder undergoing ERT will be apparent to one of skill in the art. For instance, consultation with the physician overseeing the ERT, or a review of the subject's medical chart, would normally be sufficient.

In some instances, it may be beneficial to coordinate administration of the agent that inhibits autophagy to a subject with administration of ERT to the subject. For example, administration of plasmid encoding shRNA directed to an essential autophagy gene in combination with ERT for Pompe disease is disclosed. Administration of small molecule compounds that inhibit class III PI3K inhibitors in combination with ERT for Pompe disease is disclosed. The skilled artisan will recognize appropriate administration procedures, though non-limiting examples are provided herein.

Selecting a Subject Undergoing ERT for a Lysosomal Storage Disorder

ERT for a subject with a lysosomal storage disorder comprises therapeutic administration of replacement enzyme to the subject. Thus, selecting a subject undergoing ERT for a lysosomal storage disorder comprises identifying a subject receiving therapeutic administration of a replacement enzyme for the treatment of a lysosomal storage disorder (e.g., by reference to the subject's medical charts, consultation with a physician, and so forth). It will also be appreciated that one could identify a subject who would benefit from being treated with ERT, then initiate treatment of that subject with both ERT and an autophagy inhibitor—thus, for combination therapy the subject need not already be undergoing ERT.

Enzyme replacement therapy (ERT) is used to treat several lysosomal storage disorders, including Gauchers's disease, Fabry disease, mucopolysaccharidoses (MPS) I, MPS II, MPS VI and Pompe's disease. In Pompe disease, ERT involves intravenous injections of a recombinant GAA (rhGAA) precursor protein, which is internalized into cells where it rescues the GAA deficiency. In Fabry disease, ERT involves intravenous infusions of recombinant human alpha-galactosidase A. In Gaucher disease, ERT involves administration of recombinant human Imiglucerase (available commercially as Cerezyme™ from Genzyme Corporation). In Hurler Syndrome, ERT involves administration of recombinant human alpha-L-iduronidase (Tolar and Orchard, *Biologics.*, 2:743-751, 2008). In Hunter Syndrome (Mucopolysaccharidosis II), ERT involves administration of recombinant human Idursulfase (available commercially as Elaprase™, Shire Human Genetic Therapies, Inc, Cambridge, Mass.). In Morquio syndrome (Mucopolysaccharidosis IV), ERT involves administration of recombinant N-acetylgalactosamine-6-sulfate sulfatase (Tomatsu et al., *Hum. Mol. Genet.*, 17:815-824, 2007).

In examples of the described method, selecting a subject with a lysosomal storage disorder wherein the subject is undergoing ERT for the lysosomal storage disorder comprises selecting a subject with GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome, Morquio Type A/MPS WA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease, Neuronal Ceroid Lipofuscinoses (CLN6 disease, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis), Pompe disease/Glycogen storage disease type II, Pycnodysostosis, Sandhoff disease, Schindler disease, Salla disease/Sialic Acid Storage Disease, Tay-Sachs/GM2 gangliosidosis, or Wolman disease. For instance, one embodiment of the method comprises selecting a subject undergoing ERT treatment for Pompe disease.

Procedures for identification of a subject with a lysosomal storage disorder wherein the subject is undergoing ERT for the lysosomal storage disorder are generally readily apparent to one of skill in the art. For example, identification of a subject with a lysosomal storage disorder wherein the subject is undergoing ERT (or who might benefit from being treated by ERT) may comprise identification of a subject with a lysosomal storage disorder as described herein. Identification of a subject with a lysosomal storage disorder wherein the subject is undergoing ERT may also comprise identification of a subject undergoing ERT; for example identification of a subject receiving therapeutic administration of recombinant GAA, alpha-galactosidase A, imiglucerase, alpha-L-iduronidase or N-acetylgalactosamine-6-sulfate sulfatase.

Administration to a Subject

ERT for a lysosomal storage disorder comprises administration of a therapeutically effective amount of a replacement lysosomal enzyme. One of skill in the art will be aware of an appropriate dosage of administration (see U.S. Pat. No. 7,351,410). While dosages may vary depending on the disease, the enzyme and format being administered, and the patient, the enzyme is generally administered to the patient in amounts of from about 0.1 to about 1000 milligrams per 50 kg of patient per month, preferably from about 1 to about 500 milligrams per 50 kg of patient per month. One of skill in the art will also be aware of an appropriate means of administration (see U.S. Pat. No. 7,351,410, the disclosure of which is incorporated herein in its entirety). The replacement enzyme is preferably highly phosphorylated. The replacement enzyme preferably contains mannose-6-phosphate. Within each lysosomal storage disorder, the severity and the age at which the disorder presents may be a function of the amount of residual lysosomal enzyme that exists in the subject having the disorder. Thus, treating lysosomal storage disorders with ERT includes providing a replacement lysosomal hydrolase at any or all stages of disease progression.

For example, the replacement enzyme can be administered in the form of a pharmaceutical composition containing the enzyme and any pharmaceutically acceptable carriers or by means of a delivery system such as a liposome or a controlled release pharmaceutical composition or any other acceptable system disclosed herein. The enzyme required for ERT or the composition can be administered by any standard technique compatible with enzymes or their compositions. For example, the enzyme or composition can be administered parenterally, transdermally, or transmucosally, e.g., orally or nasally. Preferably, the enzyme or composition is administered by intravenous injection.

In Pompe disease, ERT can involve intravenous injections of human recombinant GAA precursor protein that is heavily phosphorylated (sold commercially as Myozyme® and Lumizyme®, by Genzyme Corp, Cambridge, Mass.) which is internalized into cells where it rescues the GAA deficiency. Methods of treating a subject with Pompe disease are known to those of skill in the art (see, for example, U.S. Pat. No. 6,066,626, U.S. Pat. No. 6,537,785; U.S. Pat. No. 7,351,410; Sun et al., *Am J. Hum. Genet.*, 81:1042-1049, 2007; Merk et al., *Eur J. Neurol.*, 16:247-7, 2009; Strothotte et al., *J. Neurol.*, Epub Aug. 1, 2009). In Fabry disease, ERT involves intravenous infusions of recombinant human alpha-galactosidase A. In Gaucher disease, ERT involves administration of recombinant human Imiglucerase (available commercially as Cerezyme™ from Genzyme Corporation). In Hurler Syndrome, ERT involves administration of recombinant human alpha-L-iduronidase (Tolar and Orchard, *Biologics.*, 2:743-751, 2008). In Hunter Syndrome (Mucopolysaccharidosis II), ERT involves administration of recombinant human Idursulfase (available commercially as Elaprase™, Shire Human Genetic Therapies, Inc, Cambridge, Mass.). In Morquio syndrome (Mucopolysaccharidosis IV), ERT involves administration of recombinant N-acetylgalactosamine-6-sulfate sulfatase (Tomatsu et al., *Hum. Mol. Genet.*, 17:815-824, 2007).

Coordination of administration of an agent that inhibits an essential autophagy gene with ERT for a subject with a lysosomal storage disorder can be accomplished in a variety of ways. For example, the agent can be administered before, during or after ERT treatment. An agent that inhibits autophagy can be administered before, during or after a replacement enzyme is administered during the course of ERT treatment. An agent that inhibits autophagy and the replacement enzyme administered during ERT can be administered as a single composition.

For example, in a subject receiving intravenous injection of Myozyme® as a treatment for Pompe disease, an agent that inhibits autophagy can be administered in the same injection as Myozyme®, or in a different injection. For example, Myozyme® can be injected intravenously and the agent that inhibits autophagy can be injected into muscle. Alternatively, Myozyme® can be injected intravenously and a plasmid that encodes a shRNA directed to the Atg5, Atg6, Atg7, Atg9, Atg12, Atg16 or any other essential autophagy gene, is injected into muscle. Following injection of a plasmid that encodes a shRNA directed to the Atg5, Atg6, Atg7, Atg9, Atg12, Atg16 or any other essential autophagy gene into muscle, electroporation can be administered to enhance delivery of the plasmid DNA to muscle.

In other examples, in a subject receiving intravenous injection of Myozyme® as a treatment for Pompe disease, an agent that inhibits PI3K can be administered in the same injection as Myozyme®, or in a different injection. For example, Myozyme® can be injected intravenously and the agent that inhibits PI3K can be injected into muscle. In some examples, in a subject receiving intravenous injection of Myozyme® as a treatment for Pompe disease, 3-Methyladenine is administered in the same injection as Myozyme®, or in a different injection; for example, 3-Methlyadenin can be injected into muscle and Myozyme® injected intravenously. In other examples, both Myozyme® and an agent that inhibits autophagy, for example a plasmid encoding a shRNA directed to an essential autophagy gene or an agent that inhibits PI3K activity, are injected into muscle.

A suitable administration format may best be determined by a medical practitioner for each subject and situation individually. Various pharmaceutically acceptable carriers and their formulation are described in standard formulation treatises, for example, *Remington's Pharmaceutical Sciences* by E. W. Martin. See also Wang and Hanson, *J. Parenteral Sci. Technol.*, Technical Report No. 10, Supp. 42: 2S, 1988. The dosage form of the pharmaceutical composition will be influenced by the mode of administration chosen.

The therapeutically effective amount of therapeutic agent that inhibits autophagy, such as a siRNAs, shRNAs or plasmids encoding them, morpholinos, small molecule inhibitors of class III PI3K, and so forth or other inhibitor or therapeutic compound as described herein will be dependent on the particular compound utilized, the subject being treated, the severity and type of the affliction, the manner of administration and the method and mode of ERT treatment that the inhibitor of autophagy is combined with. The exact dose is readily determined by one of skill in the art based on the potency of the specific compound, the age, weight, sex and physiological condition of the subject and the impact that other treatment an individual may be undergoing will effect treatment with an agent that inhibits autophagy, as well as the teachings herein.

The following examples are provided to illustrate certain particular features and/or embodiments. These examples should not be construed to limit the invention to the particular features or embodiments described.

EXAMPLES

Example 1

Disabling Autophagy Genetically in a Mouse Model of Pompe Disease

The example describes experiments on genetically altered mice wherein autophagy is suppressed by knocking out either Atg5 or Atg7, two critical autophagic genes, in the skeletal muscle of mice lacking expression of GAA (a mouse model of Pompe disease). Suppression of autophagy alone resulted in a diminished glycogen load in these double knockout mice. Following ERT, the skeletal muscle glycogen was reduced to normal or near normal levels.

Materials and General Information

The following primary antibodies were used for immunostaining of fixed fibers: rabbit anti-LC3B (microtubule-associated protein 1 light chain 3) (Sigma, St. Louis, Mo.); rat anti-LAMP-1 (lysosomal-associated membrane protein 1) (BD Pharmingen, San Diego, Calif.); mouse anti-mono- and poly-ubiquitinated conjugates (clone FK2) (BIOMOL International, L.P., Philadelphia, Pa.); mouse monoclonal anti-alpha tubulin (Sigma); mouse monoclonal anti-GAPDH antibody (Abcam, Cambridge, Mass.) served as a loading control. Alexa Fluor-conjugated antibodies (Molecular Probes, Eugene, Oreg.) were used as secondary antibodies.

Animal care and experiments were conducted in accordance with the National Institutes of Health Guide for the Care and Use of Laboratory Animals. Data in text and figures are given as mean±S.E. The student's t test was used for comparisons between the groups. Differences were considered significant at $p<0.05$.

Generation of Muscle-Specific Autophagy-Deficient GAA-/- Mice: MLCcre:Atg7F/F:GAA-/-

Atg7-conditional knockout mice ($Atg7^{flox/flox}$) (Komatsu et al., *J. Cell Biol.*, 169:425-434, 2005) were crossed to a skeletal muscle specific Cre line to generate muscle-specific autophagy-deficient mice (MLCcre: Atg7F/F: wt). The Cre line has been generated by a knock-in of the Cre recombinase gene into the myosin light chain if (MLC) locus (Bothe et al., *Genesis,* 26:165-166, 2000). MLCcre mice show Cre expression throughout development starting from E9.5, thus enabling a selective ablation of the Atg7 gene in the developing muscle. Cre expression in this line is restricted to fast skeletal muscle fibers.

The need for tissue-specific suppression of autophagy is justified by the fact that mice with a global deletion of autophagic genes (Atg5 or Atg7) die soon after birth (Kuma et al., *Nature,* 432:1032-1036, 2004; Komatsu et al., *J. Cell Biol.,* 169, 425-434, 2005). The following steps were used to generate muscle-specific autophagy-deficient GAA-/- mice (MLCcre:Atg7F/F:GAA-/-): (1) $Atg7^{flox/flox}$ mice were crossed with GAA-/- mice (Raben et al., *J. Biol. Chem.,* 273:19086-19092, 1998) to produce Atg7F/F:GAA-/- mice; (2) MLCcre mice were crossed with GAA-/- mice to produce MLCcre:GAA-/- mice; (3) Atg7F/F:GAA-/- were then crossed with MLCcre:GAA-/- mice to produce MLCcre:Atg7F:GAA-/- mice; (4) MLCcre:Atg7F:GAA-/- mice were then intercrossed by brother/sister mating to produce MLCcre:Atg7F/F:GAA-/- animals.

In addition, MLCcre:GAA-/- mice were made to serve as the most adequate control for experiments using the MLCcre: Atg7F/F:GAA-/- mice. In the GAA-/- mice, the GAA gene, which is disrupted by a neo cassette in exon 6, also contains two loxP sites in introns 5 and 6. Therefore, the expression of Cre recombinase would remove exon 6 and the neo from the GAA gene. Removal of exon 6 from the GAA gene results in a complete inactivation of the gene. See Raben et al., *J. Biol. Chem.,* 273:19086-92, 1998; and Raben et al., *Neuromuscular disorders,* 10; 283-291, 2000. The clinical signs of muscle disease were monitored in approximately 100 mice.

Genotyping

Genomic DNA was isolated from tail clips using the iPrep™ ChargeSwitch® gDNA tissue Kit (Invitrogen, Carlsbad, Calif.) or the QuickGene DNA tissue kit (FUJIFILM, Tokyo, Japan) according to the manufacturers' instructions. The Atg7 wild type, $Atg7^{flox/+}$, and $Atg7^{flox/flox}$ alleles were detected with the primer pair (5' tggctgctacttctgcaatgatgt 3' (SEQ ID NO: 19) and 5' gaatattctaattcaaccagatctaggt 3' (SEQ ID NO: 20)) that amplifies ~1.5 kb fragment from the wt allele and ~0.5 kb fragment from the floxed allele. The presence of Cre recombinase is indicated by a 400 bp PCR product made with the primer pair: Cre sense/antisense: 5' ccggtgaacgtg-caaaacagcctcta 3' (SEQ ID NO: 21) and 5' cttccagggcgc-gagtggatagc 3' (SEQ ID NO: 22). The GAA wild type, GAA+/-, and GAA-/- alleles were detected as described in Raben et al. (*J. Biol. Chem.,* 273:19086-19092, 1998).

Isolation of Fixed Single Muscle Fibers and Immunofluorescence Microscopy

White gastrocnemius, soleus, and psoas muscles were removed immediately after sacrifice and pinned to Sylgaard-coated dishes for fixation with 2% paraformaldehyde in 0.1M phosphate buffer for 1 h, followed by fixation in methanol (–20° C.) for 6 min. Single fibers were obtained by manual teasing. Fibers were placed in a 24-well plate in Blocking Reagent (Vector Laboratories, Burlingame, Calif.) for 1 h. The fibers were then permeabilized, incubated with primary antibody overnight at 4° C., washed, incubated with secondary antibody for 2 h, washed again, and mounted in Vectashield (Vector Laboratories, Burlingame, Calif.) on a glass slide. The fibers were analyzed using a Zeiss 510 META confocal microscope. The white part of gastrocnemius and psoas muscles in mice are a good source of glycolytic fast-twitch type II fibers (referred to as fast fibers), whereas soleus muscle is a good source of oxidative slow-twitch type I fibers (referred to as slow fibers). At least three animals from each genotype were used to obtain single muscle fibers for immunostaining. For each immunostaining and for confocal analysis, at least 20 fibers were isolated from each of the three muscle groups.

Western Blot of Muscle Tissues

Whole muscle tissues were homogenized in RIPA buffer (PBS, 1% NP40, 0.5% Sodium deoxycholate, 0.1% SDS) containing a protease inhibitor cocktail tablet (Roche Diagnostics, Mannheim, Germany). Samples were centrifuged for 30 min at 13,000 rpm at 4° C. Alternatively, detergent-soluble and -insoluble fractions from muscle tissues were obtained as previously described (Hara et al. 2006). Briefly, muscle tissues were homogenized in ice-cold 0.25 M sucrose buffer (50 mM Tris-HCl pH 7.4, 1 mM EDTA; ~350 µl/100 mg tissue) with protease inhibitors. Homogenates were centrifuged at a low speed for 10 mM at 4° C., and the supernatants were lysed with an equal volume of cold sucrose buffer with 1% Triton X-100. Lysates were then centrifuged at 13,000 g for 15 mM at 4° C. to collect fractions soluble in 0.5% Triton-X-100; the pellets (Triton-X-100-insoluble fractions) were resuspended in 1% SDS in PBS.

Protein concentrations of the supernatants of the total lysates or soluble fractions were measured using Bio-Rad Protein Assay (Bio-Rad Laboratories, Inc., Hercules, Calif.). Equal amounts of protein were run on SDS-PAGE gels (Invitrogen) followed by electro-transfer onto nitrocellulose membranes (Invitrogen). Membranes were blocked in 1:1 PBS and Odyssey Blocking Buffer (LI-COR Biosciences, Lincoln, Nebr.), incubated with primary antibodies overnight at 4° C., washed, incubated with the secondary antibodies, and washed again. Blots were scanned on an infrared imager (LI-COR Biosciences, Lincoln, Nebr.).

The following primary antibodies were used for Western blots and immunostaining of fixed fibers: rabbit anti-LC3B (microtubule-associated protein 1 light chain 3) (Sigma, L7543); rat anti-mouse LAMP-1 (Lysosomal-Associated Membrane Protein 1) (BD Pharmingen, 553792); rabbit polyclonal anti-Atg7 (Cell Signaling Technology, 2631); mouse anti-poly-ubiquitinated conjugates (FK2) (BIOMOL International, PW8810); goat polyclonal anti-BECN1 (Beclin-1) (Cell Signaling Technology, 3738); rabbit monoclonal anti-GSK-3β (Cell Signaling Technology, 9315); rabbit monoclonal anti-phospho-GSK-3β (Ser9) (Cell Signaling Technology, 9323); rabbit monoclonal anti-glycogen synthase (Cell Signaling Technology, 3886), and rabbit polyclonal anti-phospho-glycogen synthase (Ser641) (Cell Signaling Technology, 3891); rabbit polyclonal anti-eIF4EBP1 (Abcam, ab2606) and anti-phospho-4E-BP1 (Cell Signaling Technology, 9459); guinea pig polyclonal anti-P62 (ProGen, GP62-N); rabbit polyclonal anti-HA-probe (Santa Cruz Biotechnology, sc-805); mouse monoclonal anti-vinculin (Sigma, V 9131) and mouse monoclonal anti-GAPDH antibody (Abcam, ab9484) served as loading controls. Alexa Fluor-conjugated antibodies (Molecular Probes, A21057, A21076, A21096) were used as secondary antibodies.

Quantitative Real-Time PCR

Total RNA was extracted from gastrocnemius muscle using TRIzol™ reagent (Gibco-BRL, 15596-026) according to standard procedures. The RNA cleanup protocol from the Qiagen RNeasy™ Mini Kit (Qiagen Sciences, 74104) was used to eliminate short transcripts. Five µg total RNA was used for cDNA synthesis using the High Capacity cDNA Archive Kit from Applied Biosystems (4368814). The cDNA was then diluted 1:5 and 1 µL of the diluted cDNA was used to perform real-time PCR in 20 µL reactions in 96-well optical plates according to the manufacturer's instructions. SYBR® Green Mouse Foxo3 primer set (SABiosciens, (Mm. 338613)) was use for the analysis. Mouse β-actin was used as an endogenous control.

Glycogen Measurement and Light Microscopy

Glycogen concentration in skeletal muscle was evaluated by measuring the amount of glucose released after treatment of tissue extracts with *Aspergillus niger* amyloglucosidase as described (Kikuchi et al., *J. Clin. Invest.*, 101:827-833, 1998), except that the enzymatic digestion was carried out at 55° C. rather than 37° C. (Kikuchi et al., *J. Clin. Invest.*, 101:827-833, 1998). Tissues were fixed in 3% glutaraldehyde (EM grade, Electron Microscopy sciences, Hatfield, Pa.) in 0.2M Sodium Cacodylate buffer for 4 h at 4° C., washed in 0.1M Sodium Cacodylate buffer, and stored at 4° C. in the same buffer. Samples were then imbedded in paraffin, sectioned, and stained with periodic acid-Schiff (PAS) by standard methods.

Enzyme Replacement Therapy

Two and a half month-old GAA−/−, MLCcre: Atg7F/F: GAA−/−, and HSAcre: Atg5F/F: GAA−/− mice received three intravenous injections of recombinant human α-glucosidase (rhGAA; Myozyme®, Genzyme Corporation, Framingham, Mass.) at a dose of 100 mg/kg every other week. To diminish a hypersensitivity reaction, diphenhydramine hydrochloride was injected intraperitoneally at a dose of 5 mg/kg 15 minutes before the second and third injections of rhGAA. The mice were sacrificed 7 days after the last injection. Twelve GAA−/−, 11 HSAcre: Atg5F/F: GAA−/−, and 9 MLCcre: Atg7F/F: GAA−/− were treated with rhGAA.

Plasmids, C2C12 Cell Cultures and Transfection

The EcoRI/XhoI fragment containing HA (hemagglutinin)-tagged GSK-3β S$^9$A was released from the pcDNA3 plasmid (Addgene plasmid #14754). This fragment was then cloned into the EcoRI/SalI sites of the pHan-Puro retroviral expression vector. GSK-3β S$^9$A is a glycogen synthase kinase in which serine 9 of human GSK-3β is mutated to alanine. When expressed, the mutant kinase is constitutively active (ca). The pHan-Puro-GFP vector was used as a control. Culturing and transfection of C2C12 myoblasts and myotubes were done according to the standard procedures with some modifications. Viral supernatants were obtained by transfection of Phoenix cells (Orbigen, RVC-10002) with the retroviral expression vectors (pHan-Puro or pHan-Puro containing constitutively active GSK-3β S9A) using the calcium phosphate method. C2C12 mouse myoblasts were grown in DMEM supplemented with 20% fetal bovine serum (Atlanta Biologicals, S11550), 0.5% chick embryo extract (Sera Laboratories International Ltd, CE-650-T), and 1% penicillin-streptomycin-glutamine (Invitrogen, 10378-016). The cells were seeded into 6-well plates ($3\times10^4$ cells/well) and infected with the filtered viral supernatant containing 8 µg/ml Polybrene (Sigma, H9268-5G). The plates were centrifuged at 3700 rpm at room temperature for 1.5 hours, placed at 37° C. overnight, and then selected in the presence of 2 µg/ml of puromycin (Invitrogen, A1113803). For differentiation of C2C12 cells into myotubes, the cells were grown to near confluence, and the culture medium was changed to DMEM containing 1% penicillin-streptomycin-glutamine and 5% horse serum (HyClone Laboratories, SH30074.03).

For starvation, the cells (myoblasts or myotubes) were incubated in Krebs-Ringer solution at 37° C. for 4 hours. Alternatively, cells were treated with 400 nM bafilomycin ((Sigma, 131793) in DMEM containing serum and supplements to inhibit autophagosome-lysosome fusion; Yamamoto et al., *Cell Struct Funct* 23(1):33-42, 1998). For Western analysis the cells were lysed in RIPA buffer with inhibitors. For immunostaining, the cells were fixed with 2% paraformaldehyde (Electron Microscopy Sciences, 15710) in 0.1M phosphate buffer for 1 hour. After several washes with PBS, myoblasts were incubated with blocking reagent (MOM kit; Vector Laboratories, BMK-2202) for 1 hour at room temperature; the cells were then incubated with primary antibodies overnight at 4° C., washed with PBS, incubated with secondary antibody for 2 hours, and washed again with PBS before examination by confocal microscopy (Zeiss LSM 510).

Force Measurements

Force measurements on the EDL (extensor digitorum longus) muscles were conducted as described (Brooks and Faulkner, *J Physiol* 404:71-82, 1988). Force measurements on single fibers isolated from psoas muscle were done as described (Xu et al., *J Appl Physiol* 108(5):1383-1388, 2010). The overall muscle strength was evaluated by grip strength measurements using a grip strength meter (Columbus Instruments, 1027 MPB); the data were normalized by body weight and expressed as KGF/kg as described (Spurney et al., *Muscle Nerve* 39(5):591-602, 2009).

Results and Discussion

The generation of a muscle-specific Atg5-deficient GAA−/− mouse (HSAcre: Atg5F/F: GAA−/−) was previously reported (Raben et al., *Hum. Mol. Genet.*, 17:3897-3908, 2008). In these mice the Cre gene is expressed in both fast and slow fibers under the control of human skeletal α-actin promoter (HSAcre). Since these mice are clinically more affected than the GAA−/− mice, another model in which suppression of autophagy was limited to type II fast-twitch muscle was generated. Suppression of autophagy in fast muscle seemed a particularly attractive approach because fast but not slow muscles showed a failure of autophagy, and because this failure of autophagy was associated with the resistance of these fibers to enzyme replacement therapy (ERT) (Raben et al., *Mol. Ther.*, 11:48-56, 2005, Fukuda et al. *Mol. Ther.*, 14:831-9, 2006). In this new model (MLCcre: Atg7F/F: GAA−/−), another critical autophagic gene, Atg7, is excised in fast muscle by the Cre recombinase driven by the myosin light chain if (MLC) promoter.

Figure 1B:
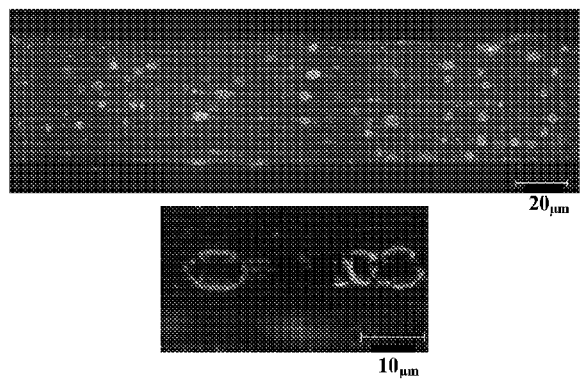
Figure 1C:
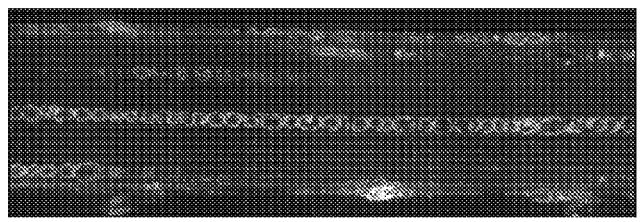
Figure 2A:
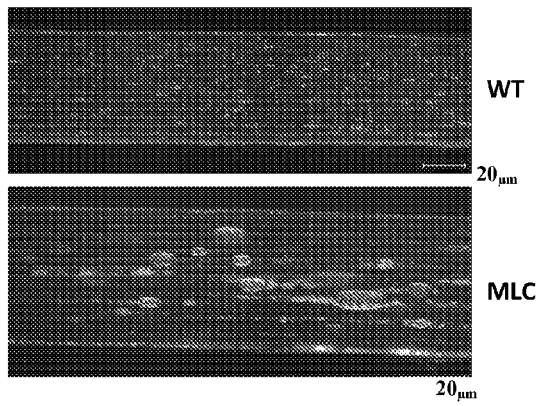
FIGS. 2A and 2B: Accumulation of ubiquitinated (Ub) proteins in fast muscle from MLCcre:Atg7F/F:GAA−/− mice.
Figure 2B:

As expected, autophagy was suppressed in fast (gastrocnemius) but not slow (soleus) muscles in the MLCcre: Atg7F/F: GAA−/− mice, as shown by the absence of LC3II, a highly specific marker for autophagic vesicles, called autophagosomes (FIG. 1A). Expansion of lysosomes, a hallmark of Pompe disease, persists in muscle fibers from MLCcre: Atg7F/F: GAA−/− mice. The size of the lysosomes varies: the majority of the fibers have relatively small lysosomes, however, occasionally one can see fibers with unusually large (up to 7-10 μm) lysosomes (FIG. 1B). In addition, clusters of lysosomes can be seen in the core of many fibers (FIG. 1C). A prominent feature of MLCcre: Atg7F/F: GAA−/− mice is that they show age-dependent accumulation of ubiquitinated proteins in their skeletal muscles, suggesting a functional impairment of the lysosomes (FIGS. 2A and B). The characteristics described above are similar to those seen in the previously described HSAcre: Atg5F/F: GAA−/− mice.

Unexpectedly, autophagy was suppressed only in adult but not in young MLCcre: Atg7F/F: GAA−/− mice, as shown by the presence of LC3II (FIG. 3A) in fast muscle from one-month old mice. Thus, the GAA−/− mouse is a model in which autophagy is suppressed later in life and would thus be a useful model in which to observe the effects of autophagy suppression (e.g., through therapeutic intervention) in established disease.

Another finding is that in fast muscles, the MLCcre: Atg7F/F: GAA−/− accumulate less glycogen compared to the HSAcre: Atg5F/F: GAA−/− strain, in which the glycogen load is already lower than in the GAA−/− by 30% (Table 1). The level of glycogen in MLCcre: Atg7F/F: GAA−/− was lower than in the GAA−/− by 57%, suggesting that autophagy plays a critical role in the delivery of lysosomal glycogen. Clinically, the MLCcre: Atg7F/F: GAA−/− mice are less affected than the HSAcre: Atg5F/F: GAA−/−, and they appear to be no worse than the GAA−/−, if not better.

TABLE 1

Glycogen levels in fast muscles of GAA −/−, MLCcre: Atg7F/F: GAA−/−, and HSAcre: Atg5F/F: GAA−/−.

|  |  | μg glucose/hr/ mg protein | % glycogen/ hr | *% Reduction |
|---|---|---|---|---|
| GAA−/− n = 60 | Gastroc/Quad | 73.9 ± 23.7 | 5.22 ± 1.90 |  |

TABLE 1-continued

Glycogen levels in fast muscles of GAA −/−, MLCcre: Atg7F/F: GAA−/−, and HSAcre: Atg5F/F: GAA−/−.

|  |  | μg glucose/hr/ mg protein | % glycogen/ hr | *% Reduction |
|---|---|---|---|---|
| MLCcre: Atg7F/F: GAA−/− n = 34 | Gastroc/Quad | 29.9 ± 16.6 p = 1.3E−14 | 2.25 ± 1.32 p = 1E−13 | 57-60 |
| HSAcre: Atg5F/F: GAA−/− n = 67 | Gastroc/Quad | 46.5 ± 17.0 p = 3E−11 **p = 9E−6 | 3.66 ± 1.75 p = 1E−5 **p = 5E−5 | 30-37 |

*The % glycogen reduction in autophagy deficient strains is calculated based on the measurement of glycogen as a percent per wet weight.
**The difference between the two autophagy deficient strains.

Figure 5:
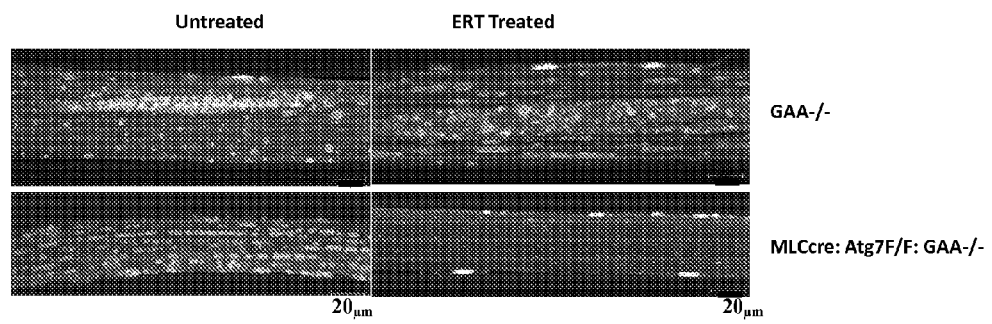
FIG. 5: Reversal of muscle pathology in the ERT-treated MLCcre:Atg7F/F:GAA−/− mice Immunostaining of single fast (psoas) fibers from untreated and ERT-treated GAA−/− and MLCcre:Atg7F/F:GAA−/− mice for LAMP-1 (lysosomal marker) and autophagosomal marker (LC3). Top panel: Autophagic buildup is clearly seen in myofibers from untreated GAA−/− mice, and this buildup persists in ERT-treated GAA−/− mice. The lysosomes after ERT are even larger than those in the untreated fiber, showing the variability in the lysosomal size. Even taking into consideration the variability in lysosomal size, the ERT appears very ineffective in GAA−/− myofibers. Bottom panel: As expected autophagic buildup is not present in myofibers from MLCcre:Atg7F/F:GAA−/− mice. Expanded lysosomes, which are clearly seen in untreated myofibers, reduce in size and appear normal. Bar=20 µm.

Considering the low glycogen load in MLCcre: Atg7F/F: GAA−/− mice and the lack of additional clinical manifestations when compared to GAA−/−, these mice were good candidates for enzyme replacement therapy (ERT). Injection of the recombinant enzyme in these mice resulted in a dramatic reduction in the glycogen level approaching wild type levels (Table 2). This glycogen clearance was also demonstrated by PAS staining of muscle biopsies (shown in black and white in FIG. 4) and by immunostaining of isolated single fibers for autophagosomal and lysosomal markers (FIG. 5). In contrast, GAA−/− mice with genetically intact autophagy cleared glycogen poorly.

TABLE 2

The Effect of ERT on Glycogen Levels (μg glucose/hr/mg protein) in GAA−/−, MLCcre: Atg7F/F: GAA−/, and HSAcre: Atg5F/F: GAA−/−.

| Genotype | Tissue | Untreated | Treated | *Excess Glycogen | Treated vs. Untreated GAA −/− % Reduction |
|---|---|---|---|---|---|
| GAA−/− | Gastroc | 71.9 ± 22.7 (n = 29) | 52.5 ± 22.7 (n = 14) | 48.1 | 27 |
|  | Quad | 75.7 ± 24.8 (n = 31) | 54.5 ± 29.6 (n = 12) | 50.1 | 28 |
|  | Heart | 197.4 ± 41.7 (n = 13) | 0.6 ± 1.2 (n = 12) | 0 | 100 |
| MLCcre: Atg7F/F: GAA−/− | Gastroc | 25.0 ± 13.4 (n = 18) | 8.6 ± 8.9 (n = 9) | 4.2 | 88 |
|  | Quad | 35.0 ± 18.4 (n = 17) | 13.7 ± 10 (n = 9) | 9.3 | 82 |
|  | Heart | 199.2 ± 79.1 (n = 13) | 0.2 ± 0.4 (n = 9) | 0 | 100 |
| HSAcre: Atg5F/F: GAA−/− | Gastroc | 42.6 ± 18.9 (n = 33) | 4.1 ± 4.9 (n = 11) | 0 | 94 |
|  | Quad | 50.4 ± 14.1 (n = 34) | 5.0 ± 4.9 (n = 11) | 0.6 | 94 |
|  | Heart | 148.4 ± 34.5 (n = 14) | 0.0 ± 0.0 (n = 11) | 0 | 100 |

*The excess glycogen is calculated by subtracting the wild type levels from the values in treated animals. The wild type levels in gastroc and quad combined are 4.4 ± 4.6 μg glucose/mg protein.

Figure 6:
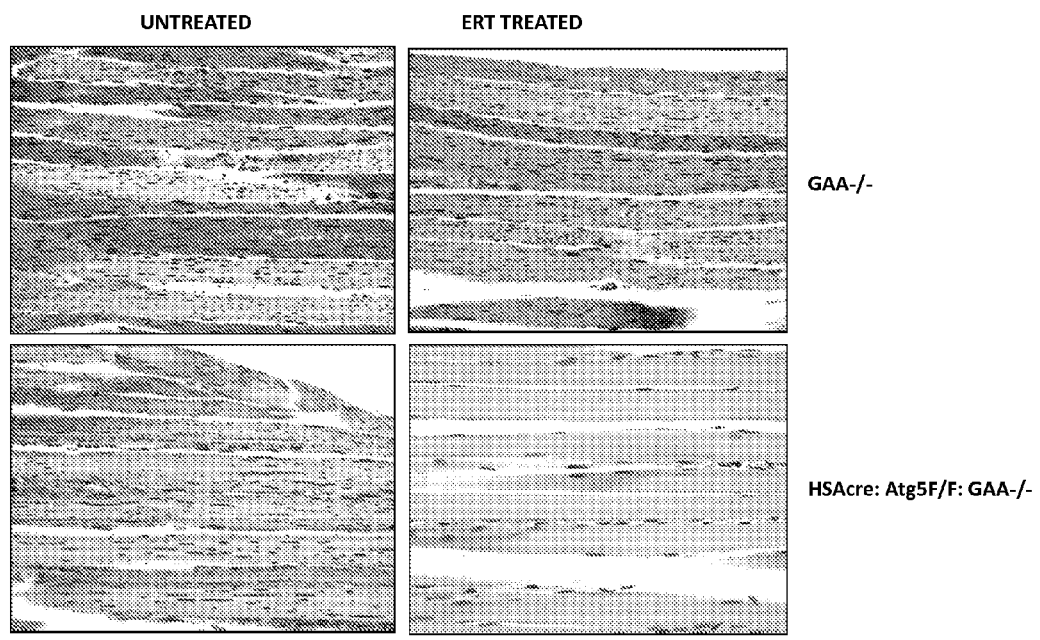
FIG. 6: Suppression of autophagy in HSAcre:Atg5F/F:GAA−/− permits fully effective enzyme replacement therapy. PAS-stained sections of fast (gastrocnemius) muscle from 4 month-old untreated and ERT-treated GAA−/− and HSAcre:Atg5F/F: GAA−/− mice shows a near complete glycogen clearance in HSAcre:Atg5F/F:GAA−/−, but not in GAA−/− mice. PAS-positive material (small dots) represents glycogen.
Figure 7:
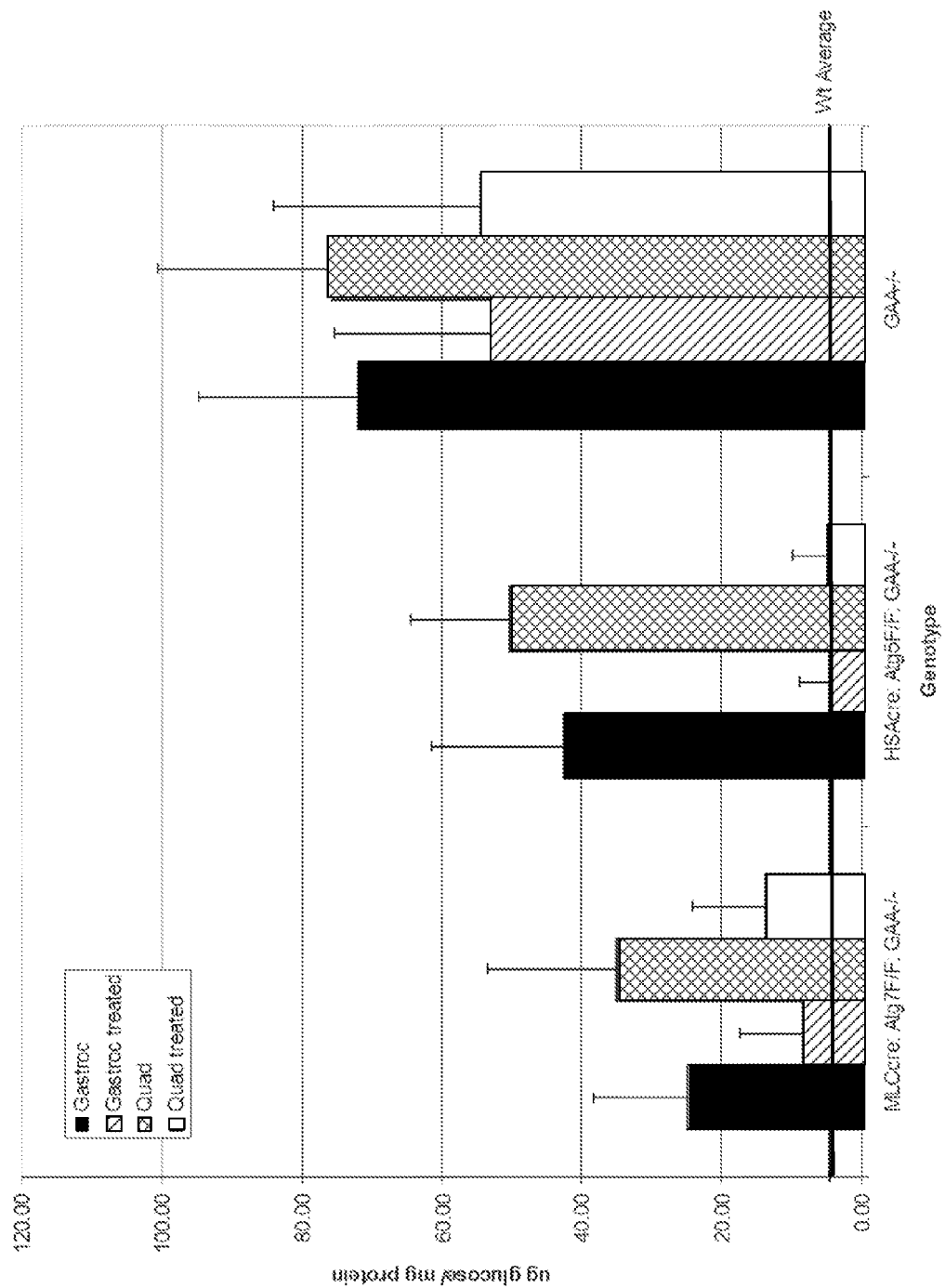
FIG. 7: Effect of ERT on glycogen levels in GAA−/− and in autophagy-deficient GAA−/− strains. Both MLCcre:Atg7F/F:GAA−/− and HSAcre:Atg5F/F:GAA−/− mice contain less glycogen in their fast muscles (gastrocnemius and quadriceps) compared to the levels of glycogen in GAA−/− mice. Both autophagy-deficient GAA−/− strains respond to ERT much better compared to the autophagy-competent GAA−/−, as shown by the reduction of glycogen levels to normal or near normal levels.

As mentioned above, the non-ERT treated MLCcre: Atg7F/F: GAA−/− mice had a much lower glycogen level in skeletal muscle compared to the GAA−/−. To determine if this low initial glycogen load accounted for the dramatic effect of ERT and to address this issue, the same ERT regimen in the HSAcre: Atg5F/F: GAA−/− strain with higher initial glycogen levels was used. As shown in Table 2, complete removal of the accumulated glycogen was observed in these mice, and the results were confirmed by PAS staining of muscle biopsies (FIG. 6). Thus, a combination of suppression of autophagy and ERT resulted in a normalization of the glycogen level irrespective of the initial amount (FIG. 7), suggesting that the removal of autophagic buildup is a major factor that causes this therapy to be so effective.

Figure 8A:
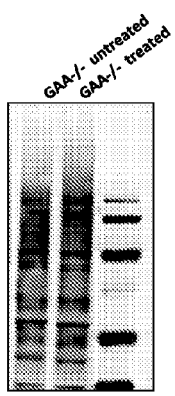
FIG. 8: Effect of ERT on the level of ubiquitinated (Ub) proteins in GAA−/− and HSAcre:Atg5F/F:GAA−/− mice. A. Total lysates from fast (gastrocnemius) muscle of untreated and ERT-treated GAA−/− mice were analyzed by immunoblotting with anti-ubiquitin (FK2) antibody. No difference in the amount of the Ub-proteins is observed in the two samples. B. Muscle lysates (prepared as detergent (Triton X-100)-soluble and non-soluble fractions) from fast (gastrocnemius) muscle of untreated and ERT-treated mice of the indicated genotypes, were analyzed by immunoblotting with anti-ubiquitin (FK2) antibody. A significant drop in the amount of Ub-proteins is observed in both soluble and non-soluble fractions from the ERT-treated compared to untreated HSAcre:Atg5F/F:GAA−/− mice. The level of Ub-proteins in treated mice is similar to those seen in autophagy-deficient mice on a wild type background, but still higher than in the wild type. This is consistent with previous data showing that constitutive autophagy is partially responsible for the removal of Ub-proteins.
Figure 8B:
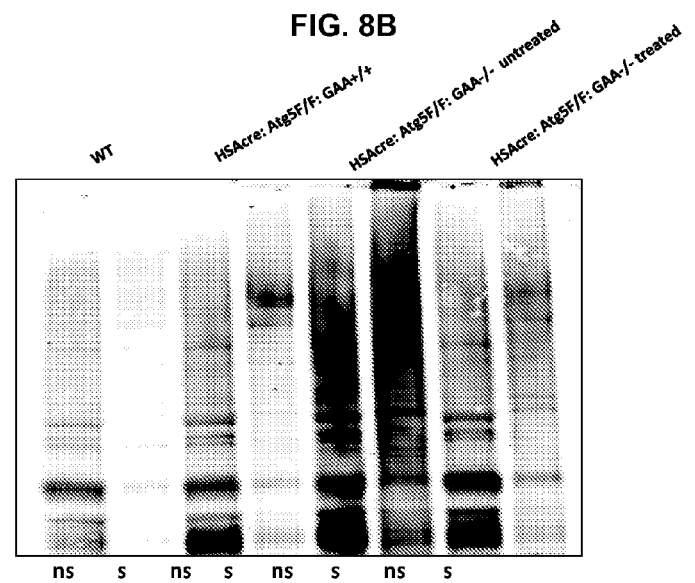
Figure 9:
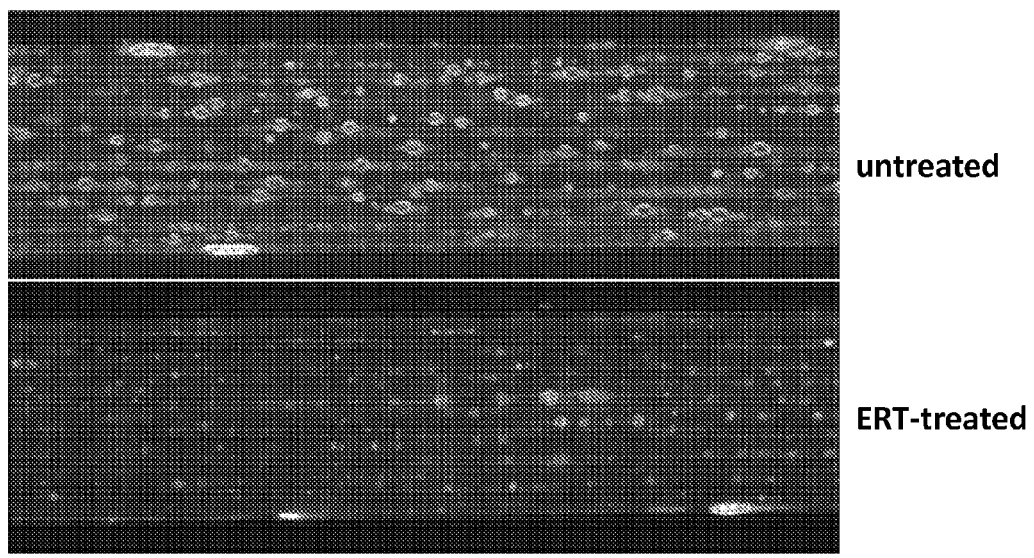
FIG. 9: Effect of ERT on the level of ubiquitinated (Ub) proteins in HSAcre:Atg5F/F:GAA−/− mice. Singe fast (psoas) myofibers were immunostained for lysosomal marker (LAMP-1) and a marker for Ub-proteins (FK2). The Ub-proteins are clearly observed in untreated, but not in ERT-treated myofibers from the autophagy-deficient GAA−/− mice.

The level of ubiquitinated-proteins in gastrocnemius muscles of ERT-treated GAA−/− and autophagy-deficient GAA−/− strains was examined. No reduction of ubiquitinated-proteins is observed in ERT-treated GAA−/− mice (FIG. 8A). In contrast, ERT-treatment in autophagy-deficient GAA−/− strains resulted in a significant decrease in the amount of ubiquitinated-proteins in both soluble and non-soluble fractions (shown for HSAcre: Atg5F/F: GAA−/− in FIG. 8B). This reduction was also shown by immunostaining of isolated muscle fibers with antibodies against ubiquitinated-proteins (FIG. 9). These data strongly suggest that the lysosomal function in treated autophagy-deficient GAA−/− mice is largely restored.

It should be noted that even the most successful reversal of lysosomal pathology in ERT-treated autophagy-deficient GAA−/− mice leaves these animals autophagy-deficient in skeletal muscle. Observational data (up to 18 months) shows that skeletal muscle-specific suppression of autophagy in the wild type mice does not result in major abnormalities as shown by apparent strength, mobility, weight, and lifespan. Thus, the suppression of autophagy in skeletal muscle greatly facilitates the effect of ERT resulting in an outcome which has never been observed in Pompe mice with genetically intact autophagy.

Possible Triggers of Autophagy in Fast Muscle of GAA−/− Mice

It has previously been demonstrated that autophagy is up-regulated in Pompe muscle (Raben et al., *Hum Mol Genet* 17(24):3897-3908, 2008). Two additional pieces of information supporting the up-regulation of autophagy are disclosed herein: Beclin-1, a protein known to be activated during autophagy induction (Cao and Klionsky, *Cell Res* 17(10): 839-849, 2007), and the Atg7 protein are increased in GAA−/− fast muscle.

Unraveling the mechanisms of autophagic disturbance in skeletal muscle under pathological conditions is challenging, particularly because skeletal muscle is a peculiar tissue in terms of how it responds to the classic inducers of autophagy—starvation and an mTOR inhibitor, rapamycin. Unlike cardiac muscle, WT fast muscle showed no appreciable increase in the amount of LC3-II following 24 or 48 hours of starvation. This outcome was unexpected because it had been previously shown that starvation did result in conversion of LC3-I to LC3-II in muscle (Mizushima et al., *Mol Biol Cell* 15(3):1101-1111, 2004). The discrepancy may be attributed to the differences in the kind of muscles used (the studies described herein consistently used only the white part of the gastrocnemius muscle), the genetic background, and the age of the animals. For starvation experiments, 4-5 month old animals were routinely used; in young, ~1 month old mice, a mild response to starvation was observed, but the results were inconsistent.

Rapamycin also does not induce autophagy in WT skeletal muscle as shown by the inventors and others (Mammucari et al., *Cell Metab* 6(6):458-471, 2007). Similar to the effect of rapamycin in the WT muscle, no increase in LC3-II was detected in muscle from GAA−/− mice although mTOR activity was suppressed by the drug as evidenced by a decrease in the amount of the hyper-phosphorylated (γ) 4E-BP1. Furthermore, the mTOR regulation of protein synthesis in GAA−/− muscle is atypical. mTOR regulates protein synthesis through the phosphorylation and inactivation of 4E-BP1, a repressor of mRNA translation (Hay and Sonenberg, *Genes Dev* 18(16):1926-1945, 2004). In the GAA−/− muscle there is a significant increase in both hypo-(α and β) and hyper-phosphorylated (γ) forms of 4E-BP1.

The role of FOXO transcription factors, known to be involved in the induction of autophagy (Mammucari et al., *Cell Metab* 6(6):458-471, 2007), is also not clear in GAA−/− muscle. The inventors have previously shown that FOXO1 was not up-regulated in fast muscles of GAA−/− mice (Raben et al., *Hum Mol Genet* 17(24):3897-3908, 2008). It is demonstrated herein by real-time PCR that FOXO3 is in fact down-regulated (~1.5 fold) in fast muscles of GAA−/− mice (n=5).

Although starvation does not appear to induce autophagy in WT muscle, in GAA−/− muscle, an increase in LC3-II upon starvation was observed. This sensitivity to starvation of fast muscle in the GAA−/− mice may be one of the factors contributing to the increase in autophagy in this disease.

Considering the lack of clarity concerning the classical triggers of autophagy in GAA−/− muscle, a recently appreciated regulator of autophagy, glycogen synthase kinase 3β (GSK-3β), a protein long known to be involved in glycogen metabolism, was studied. A significant decrease in phosphorylation (activation) of GSK-3β was observed in skeletal muscle in both young and old GAA−/− mice, leading to an increase in phosphorylation (inactivation) of glycogen synthase (GS). The inactivation of glycogen synthase may reflect a homeostatic adjustment in muscle cells to reduce the cytoplasmic glycogen burden, but it appears to come at a price— the induction of autophagy by activation of GSK-3β, with deleterious effects on Pompe skeletal muscle.

To investigate whether or not GSK-3β can induce autophagy in muscle cells, a constitutively active GSK-3β$^{S9A}$ was expressed in C2C12 cells. Indeed, immunostaining and Western analysis for LC3 showed an induction of autophagy in both C2C12 myoblasts and myotubes. Furthermore, a similar induction of autophagy was observed in GAA−/− derived primary myoblasts (Takikita et al., *Mol Genet Metab* 96(4): 208-217, 2009) as demonstrated by a two-fold increase of LC3-II/α-tubulin ratio in the cells expressing GSK-3β$^{S9A}$ as compared to those expressing the vector alone. Consistent with the data in whole muscle, mTOR signaling does not appear to regulate autophagy in C2C12 myotubes, as shown by the absence of changes in the levels of phosphorylated 4E-BP1 in the cells expressing GSK-3β$^{S9A}$.

Thus, a homeostatic attempt to down-regulate the synthesis of glycogen may contribute to the up-regulation of autophagy in this glycogen storage disorder.

Example 2

Inhibiting Autophagy Using Plasmid Encoding shRNA

This example describes a representative method for delivery of a plasmid encoding shRNA directed to Atg5, an essential autophagy gene, into tissue culture cells and into skeletal muscle. For delivery into muscle, the plasmid was injected locally, followed by electroporation.

Methods

The vector backbone (Promega, Madison, Wis.) contains the U1 promoter driving shRNA expression and the CMV promoter driving GFP gene expression. cDNA sequence (SEQ ID NO: 15) encoding an shRNA sequence targeting Atg5 was inserted into the plasmid. This sequence is designed to knock-down the expression of the mouse Atg5 gene. cDNA sequence (SEQ ID NO: 17) encoding a control shRNA sequence was inserted into the plasmid. The control plasmid does not target any known gene.

Atg5-specific or control shRNA plasmid was transfected into a cell line derived from mouse mammary tissue to test suppression of Atg5 expression by shRNA. The plasmids also encode GFP, which is used as a marker of transfection efficiency. As indicated by GFP expression 48 hours post transfection, transfection efficiency was ~70% (FIG. 10).

The Atg5-specific or control shRNA plasmids were introduced into the TA muscles of adult mice to test shRNA-induced suppression of Atg5 expression in a subject. The animals were under general anesthesia before surgery. An incision was made to expose the TA muscle. TA muscles were pre-treated by injecting 30 μl (0.5 U/μl) of hyaluronidase. Two hours later, the shRNA-containing plasmids (40 μl, at 2 μg/μl) in saline solution were injected via a sterile 30G needle. Following injection, electroporation was used to enhance delivery into muscle cells (using methods essentially as described by Schertzer et al., *Mol. Ther.*, 13:795-803, 2006). Platinum electrodes were placed at a right angle to the longitudinal axis of the muscle and a train of short currents were delivered: three transcutaneous pulses (each 20 ms in duration) across the TA muscle at a voltage of 75-100V. The polarity was then reversed and three more pulses were delivered. After the procedure, the skin was sutured with surgical staples.

Results shRNA interference is a promising tool for therapeutic gene silencing, including gene silencing of an essential autophagy gene in order to inhibit autophagy and thereby treat a lysosomal storage disorder.

Figure 10:
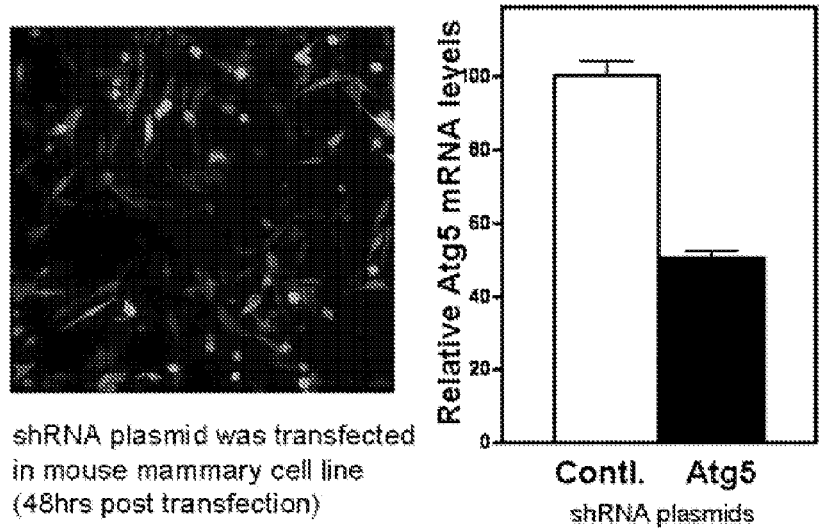
FIG. 10: Suppression of Atg5 gene expression by Atg5-specific shRNA. Atg5-specific or control shRNA plasmid was transfected into a cell line derived from mouse mammary tissue. The plasmids also encode GFP, which is used as a marker of transfection efficiency. As indicated by GFP expression 48 hours post transfection, transfection efficiency was ~70%. In the Atg5-specific shRNA plasmid transfected cells, Atg5 mRNA levels were suppressed ~50% compared to that of cells transfected with control plasmid.
Figure 11:
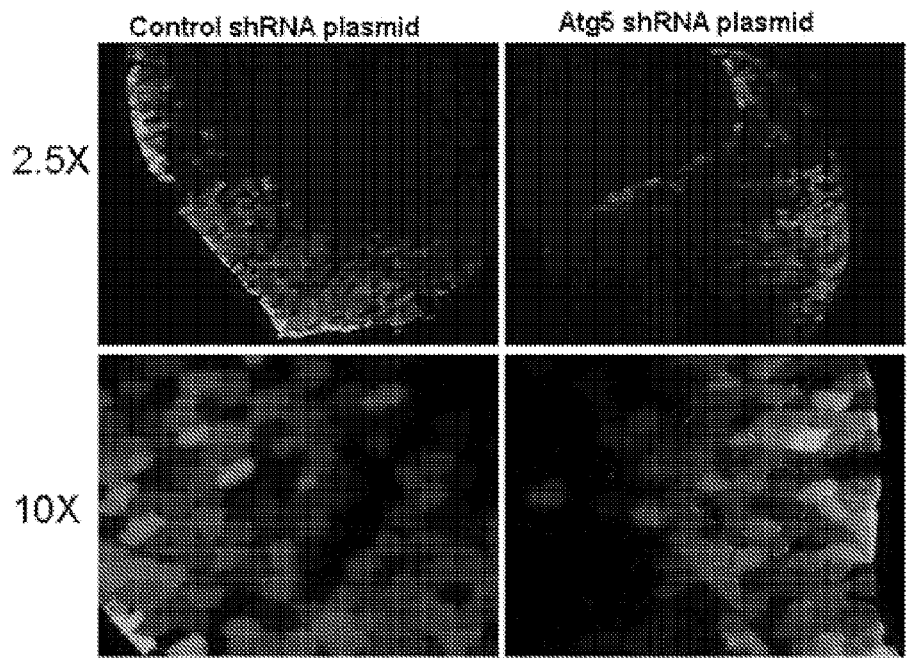
FIG. 11: Expression of shRNA plasmids in tibialis anterior (TA) Muscle. TA muscle was injected with control plasmid or plasmid encoding shRNA directed to Atg5, followed by electroporation. The plasmids also encode GFP, which is used as a marker for cells expressing the plasmid. Cross-section images (2.5× (upper) or 10× (below)) of TA muscle seven days post-shRNA plasmid or control plasmid delivery are shown. Both Atg5 specific (right) and control (left) plasmids were expressed as indicated by the GFP marker.

In the Atg5-specific shRNA plasmid transfected cells, Atg5 mRNA levels were suppressed ~50% compared to that of cells transfected with control plasmid (FIG. 10). A key limit of its application to muscle is the delivery of the plasmid DNA. Electroporation with contact electrodes was used to deliver Atg5 specific and control plasmids into TA muscles. Using this procedure, the plasmid DNA was delivered to TA muscle and plasmid expression was confirmed by detecting expression of GFP in the muscle to which the plasmid was delivered (FIG. 11). The plasmids have been transfected into a substantial number of muscle fibers, which offers promising for therapeutic application. Co-expression of GFP from the same backbone of shRNA plasmids allows localizing the transfected fibers which is essential to further examine the gene silencing and therapeutic effect accurately.

The results of this study demonstrated that the Atg5 shRNA plasmids were expressed constitutively for at least three weeks, in up to 20% of fibers in electroporated muscles, as indicated by GFP marker co-expressed from the shRNA plasmid vector. However, an inflammatory reaction was observed in the GFP-positive area. As a result, it was difficult to determine the effects of Atg5 gene silencing on autophagy and pathology of Pompe muscle.

Example 3

Injection of 3-methyladenine (3-MA) into the Muscle of a Subject

This example describes delivery of 3-Methyladenine, a class III PI3K inhibitor that inhibits autophagy, into muscle.

3-MA is widely used to inhibit autophagy in tissue cultured cells. However, despite its widespread use in vitro for over 20 years (Rubinsztein et al., *Nature Rev. Drug Disc.*, 6:304, 2007), a description of its use in animals could not be identified. Additionally, no FDA approved drug is available for autophagosome formation inhibition. Thus, this example discloses experiments to discover the effects in muscles injected locally.

3-MA is available commercially (e.g., from Sigma; Cat. No. M9281). 3-MA was dissolved in saline and injected at a dose equivalent to 0.3% to 6% ip $LD_{50}$ dose into TA muscle; the ip $LD_{50}$ dose for 3-MA is 280 mg/kg (Sigma MSDS). These dosages were tolerated well by mice, in that no toxicity was observed.

Next, a series of doses of 3-MA was administered to TA muscles by intramuscular injection to examine the histology of treated muscles. 3-MA had very mild toxicity at doses below 40 μl of 5 mg/ml per TA, as indicated by fibers with centralized nuclei. However, fiber injury was more apparent if a higher dose of 3-MA (e.g. 40 μl of 10 mg/ml 3-MA per TA) was applied.

3-MA was administered using the highest possible safety dose (40 l of 5 mg/ml per TA) determined from the above-described study. Two injections (six days apart) were given into TA muscle. Two to three days after the second injection, the treated muscles were harvested to examine the histology, the level of autophagy marker LC3, and the glycogen content. The results suggested that this regimen did not inhibit autophagy effectively in the injected muscle.

Example 4

Treatment of Pompe Disease in a Subject

This example describes a non-limiting method of treating a subject with a lysosomal storage disorder by selecting a subject with a lysosomal storage disorder (for example, Pompe disease) and administering to the subject a therapeutically effective amount of an agent that inhibits autophagy. A suitable subject for treatment is one having a lysosomal storage disorder (for example, Pompe disease).

A therapeutically effective amount of an agent that inhibits autophagy is then administered to the subject, for instance by administering to the subject a therapeutically effective amount of a plasmid encoding an shRNA directed to an essential autophagy gene (for example, Atg5 or Atg7), or by administering to the subject a therapeutically effective amount of a morpholino oligonucleotide that reduces expression of an essential autophagy gene (for example Atg5 or Atg7), or by administering to a subject a therapeutically effective amount of a compound that inhibits the activity of PI3K (for example, 3-Methyladenine). The agent can be administered locally or systemically. The compound may be given once, or repeatedly over a time period, for instance once or twice daily, every other day, weekly, or more or less often.

Optionally (but beneficially), the health or disease state of the subject (particularly with regard to the lysosomal storage disorder) is monitored over time to determine or monitor the effectiveness of the treatment; treatment can then be adjusted as necessary. Treatment is considered successful where disease symptoms are measurably reduced, for instance as indicated by clearance of glycogen or ubiquitinated proteins as described herein for Pompe disease. Representative methods for detecting such outcomes are provided herein.

Example 5

Enhancement of ERT Treatment of Pompe Disease in a Subject

This example describes a representative method for treating a subject with a lysosomal storage disorder by selecting a subject with a lysosomal storage disorder wherein the subject is undergoing ERT (for example, but not limited to, ERT for Pompe disease) and administering to the subject a therapeutically effective amount of an agent that inhibits autophagy.

A suitable subject for treatment is one having a lysosomal storage (for example, Pompe disease), wherein the subject is undergoing ERT for the lysosomal storage disorder (for example, treatment of Pompe disease with Myozyme®). ERT for a subject with a lysosomal storage disorder comprises therapeutic administration of replacement enzyme to the subject, and is well recognized by those of skill in the art.

Coordination of administration of an agent that inhibits an essential autophagy gene with ERT for a subject with a lysosomal storage disorder can be accomplished in a variety of ways. For example, the autophagy inhibiting agent can be administered before, during or after ERT treatment, or before, during or after a course of ERT treatment. In some embodiments, the agent(s) that inhibit autophagy and the replacement enzyme used for ERT are administered as a single composition.

For example, in a subject receiving intravenous injection of Myozyme® as a treatment for Pompe disease, an agent that inhibits autophagy is administered in the same injection as Myozyme®, or in a different injection. For example, Myozyme® is injected intravenously and the agent that inhibits autophagy is injected into muscle (though not necessarily simultaneously). Alternatively, Myozyme® is injected intravenously and a plasmid that encodes a shRNA directed to the Atg5, Atg6, Atg7, Atg9, Atg12, Atg16 or any other essential autophagy gene, is injected into muscle or is injected intravenously (again, not necessarily simultaneously). Alternatively, in a subject receiving intravenous injection of Myozyme® as a treatment for Pompe disease, an agent that inhibits PI3K (for example, 3-Methyladenine) can be administered in the same injection as Myozyme®, or in a different injection (at the same or a different time. For example, Myozyme® can be injected intravenously and 3-Methyadenine can be injected into muscle (not necessarily simultaneously).

Example 6

Pompe Mouse Model for Monitoring Autophagy

To monitor autophagy in vivo in Pompe mice and to facilitate the development of pharmaceuticals that block autophagy, a Pompe mouse strain in which autophagosomes are labeled with green fluorescent protein (GFP) was developed.

GFP-LC3-wt transgenic mice express a fluorescent autophagosomal marker, LC3. The development of these mice is described by Mizushima et al. (*Mol. Biol. Cell* 15(3): 1101-1111, 2004). GFP-LC3-wt mice were crossed to GAA−/− mice (Pompe mouse model). The progeny of these crosses were then intercrossed to generate GFP-LC3-GAA−/− mice. Genotyping was performed by PCR analysis of tail DNA. Pilot experiments with live anesthetized GFP-LC3-GAA−/− mice demonstrated the extent of autophagy in Pompe mice and showed the feasibility of in vivo imaging to monitor autophagic activity.

In view of the many possible embodiments to which the principles of this invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

The invention claimed is:

1. A method of treating Pompe disease in a subject undergoing enzyme replacement therapy (ERT) for Pompe disease, comprising:
   administering to the subject a therapeutically effective amount of an antisense compound that inhibits expression of essential autophagy gene Atg5 or essential autophagy gene Atg7,
   thereby treating Pompe disease in the subject.

2. The method of claim 1, wherein the antisense compound is administered intramuscularly.

3. The method of claim 1, wherein the antisense compound inhibits expression of essential autophagy gene Atg5 or essential autophagy gene Atg7 in skeletal muscle.

4. The method of claim 1, wherein the administering comprises administering to the subject a therapeutically effective amount of:
   (a) an oligonucleotide comprising at least 15 bases that hybridizes under high stringency conditions to an mRNA encoding essential autophagy gene Atg5 or essential autophagy gene Atg7;
   (b) a morpholino oligonucleotide comprising at least 15 bases that hybridizes under high stringency conditions to an mRNA encoding essential autophagy gene Atg5 or essential autophagy gene Atg7;
   (c) an shRNA comprising at least 15 bases that hybridizes under high stringency conditions to an mRNA encoding essential autophagy gene Atg5 or essential autophagy gene Atg7; or
   a mixture or combination of two or more of a, b, or c.

5. The method of claim 1, wherein the antisense compound inhibits expression of essential autophagy gene Atg5.

6. The method of claim 4, wherein the shRNA is expressed from a plasmid.

7. The method of claim 4, wherein the shRNA comprises the sequence set forth as SEQ ID NO: 16.

8. The method of claim 4, wherein the oligonucleotide, morpholino oligonucleotide or shRNA is at least 80%, at least 85%, at least 90%, at least 95% or at least 99% complementary to the mRNA encoding the essential autophagy gene.

9. The method of claim 1, wherein the antisense compound comprises a detectable label.

10. The method of claim 4, wherein the antisense compound comprises an oligonucleotide comprising at least 15 bases that hybridizes under high stringency conditions to an mRNA encoding Atg5 or Atg7.

11. The method of claim 4, wherein the antisense compound comprises a morpholino oligonucleotide comprising at least 15 bases that hybridizes under high stringency conditions to Atg5 or Atg7.

12. The method of claim 1, wherein the antisense compound comprises an shRNA comprising at least 15 bases that hybridizes under high stringency conditions to an mRNA encoding Atg5 or Atg7.

13. The method of claim 12, wherein the shRNA comprises the sequence set forth as SEQ ID NO: 16.

14. The method of claim 1, wherein the essential autophagy gene is Atg7.

15. A method of treating Pompe disease in a subject undergoing enzyme replacement therapy (ERT) therefor, comprising:

administering to the subject a therapeutically effective amount of a morpholino oligonucleotide that:
(1) comprises at least 15 bases that hybridize under high stringency conditions to an mRNA encoding essential autophagy gene Atg5 and thereby inhibits expression of essential autophagy gene Atg5; or
(2) comprises at least 15 bases that hybridize under high stringency conditions to an mRNA encoding essential autophagy gene Atg7 and thereby inhibits expression of essential autophagy gene Atg7; and
is conjugated to a cell-penetrating peptide,
thereby treating Pome disease in the subject.

16. The method of claim 15, wherein the morpholino oligonucleotide inhibits expression of the essential autophagy gene Atg5 or essential autophagy gene Atg7 in skeletal muscle.

* * * * *